United States Patent
Moon et al.

(10) Patent No.: US 10,629,824 B2
(45) Date of Patent: Apr. 21, 2020

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Doo-Hyeon Moon, Gyeonggi-do (KR); Yeon-Gun Lee, Gyeonggi-do (KR)

(73) Assignee: Rohm and Haas Electronic Materials Korea Ltd, Seoul (KR)

( * ) Notice: Subject to any disclaimer, the term of this patent is extended or adjusted under 35 U.S.C. 154(b) by 0 days.

(21) Appl. No.: 16/462,988

(22) PCT Filed: Dec. 12, 2017

(86) PCT No.: PCT/KR2017/014518
§ 371 (c)(1),
(2) Date: May 22, 2019

(87) PCT Pub. No.: WO2018/110930
PCT Pub. Date: Jun. 21, 2018

(65) Prior Publication Data
US 2019/0296249 A1   Sep. 26, 2019

(30) Foreign Application Priority Data

Dec. 14, 2016 (KR) .................. 10-2016-0170489
Dec. 7, 2017 (KR) .................. 10-2017-0167161

(51) Int. Cl.
*C07D 487/04* (2006.01)
*C07D 487/06* (2006.01)
*H01L 51/00* (2006.01)
*C09K 11/06* (2006.01)
*H01L 51/50* (2006.01)

(52) U.S. Cl.
CPC ........ *H01L 51/0072* (2013.01); *C07D 487/06* (2013.01); *C09K 11/06* (2013.01); *H01L 51/0067* (2013.01); *C09K 2211/1018* (2013.01); *H01L 51/5012* (2013.01); *H01L 51/5072* (2013.01)

(58) Field of Classification Search
CPC .......................... C07D 487/04; C07D 487/06
See application file for complete search history.

(56) References Cited

U.S. PATENT DOCUMENTS

| 9,502,667 | B2 | 11/2016 | Saito et al. |
| 9,997,724 | B2 | 6/2018 | Kim et al. |
| 2016/0163998 | A1 | 6/2016 | Saito et al. |
| 2018/0033975 | A1 | 2/2018 | Kim et al. |
| 2018/0331301 | A1 | 11/2018 | Parham et al. |

FOREIGN PATENT DOCUMENTS

| WO | 2016080791 A1 | 5/2016 |
| WO | 2016105165 A2 | 6/2016 |

*Primary Examiner* — Emily A Bernhardt
(74) *Attorney, Agent, or Firm* — S. Matthew Cairns

(57) ABSTRACT

The present disclosure relates to an organic electroluminescent compound and an organic electroluminescent device comprising the same. The organic electroluminescent compound of the present disclosure has a high glass transition temperature that can be used in a deposition process. In addition, an organic electroluminescent device having low driving voltage, a high luminous efficiency and/or long lifespan characteristic can be provided with the use of the organic electroluminescent compound according to the present disclosure.

9 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic EL device (OLED) changes electric energy into light by applying electricity to an organic electroluminescent material, and commonly comprises an anode, a cathode, and an organic layer formed between the two electrodes. The organic layer of the organic EL device may comprise a hole injection layer, a hole transport layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, an electron blocking material, a light-emitting material, an electron buffer material, a hole blocking material, an electron transport material, an electron injection material, etc., depending on their functions. In the organic EL device, holes from the anode and electrons from the cathode are injected into a light-emitting layer by the application of electric voltage, and excitons having high energy are produced by the recombination of the holes and electrons. The organic light-emitting compound moves into an excited state by the energy and emits light from an energy when the organic light-emitting compound returns to the ground state from the excited state.

In an organic electroluminescent device, research is continuing to improve the performance of an organic electroluminescent device by using a material suitable as a material used for each layer.

An electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as Alq$_3$ are excellent in transporting electrons, and thus have been conventionally used as an electron transport material. However, Alq$_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Further, the electron buffer layer is a layer for solving the problem of a change in luminance caused by the change of a current characteristic of the device when exposed to a high temperature during a process of producing a panel. In order to obtain a similar current characteristic and a stability against high temperature exposure compared to a device without an electron buffering layer, the characteristic of the compound comprised in the electron buffer layer is important.

Meanwhile, an organic electroluminescent material can form layers by deposition, the deposition process commonly being performed at a high temperature above 130° C. Thus, an organic electroluminescent compound capable of withstanding heat at high temperatures is required.

Japanese Patent Laid-Open No. 2014-160813 A discloses a compound in which a pyrrole, a plurality of benzene rings, and a 7-membered ring are fused, as a compound for a host material of an organic electroluminescent device. However, the aforementioned document does not specifically disclose a compound in which an imidazole, a plurality of benzene rings, and a 7-membered ring are fused. Furthermore, it does not disclose specific examples using such a compound as electron buffer materials and electron transport materials.

DISCLOSURE OF THE INVENTION

Problems to be Solved

The objective of the present disclosure is to provide an organic electroluminescent compound which is effective for producing an organic electroluminescent device having good driving voltage, luminous efficiency and/or lifespan characteristic while having a high glass transition temperature (Tg), which can be used in a common deposition process.

Solution to Problems

As a result of intensive studies to solve the technical problem above, the present inventors found the aforementioned objective can be achieved by the organic electroluminescent compound represented by the following formula 1, and completed the present invention.

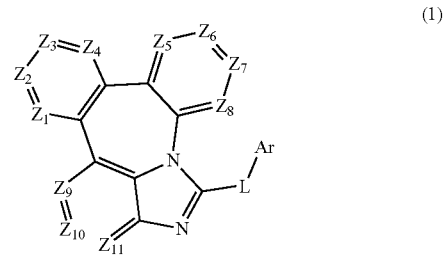

(1)

wherein formula 1, $Z_1$ to $Z_{11}$ each independently represent $CR_1$ or N;

$R_1$ represents hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur;

L represents a single bond, a substituted or unsubstituted (C6-C30)arylene, or a substituted or unsubstituted (5- to 30-membered)heteroarylene;

Ar represents hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)ar(C1-C30)alkyl, —N($R_{11}$)($R_{12}$), —Si($R_{13}$)($R_{14}$)($R_{15}$), —S($R_{16}$), —O($R_{17}$), cyano, nitro or hydroxy;

$R_{11}$ to $R_{17}$ each independently represent hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur;

the heteroaryl(ene) contains at least one heteroatom selected from B, N, O, S, Si, and P.

Effects of the Invention

The organic electroluminescent compound according to the present disclosure has a high glass transition temperature that can be used in a deposition process. In addition, an organic electroluminescent device having low driving voltage, high luminous efficiency and/or long lifespan characteristic can be provided with the use of the organic electroluminescent compound of the present disclosure.

EMBODIMENTS OF THE INVENTION

Hereinafter, the present disclosure will be described in detail. However, the following description is intended to explain the invention, and is not meant in any way to restrict the scope of the invention.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material.

An organic electroluminescent compound of the present disclosure comprises at least one compound represented by formula 1. The compound of formula 1 may be comprised in at least one layer, which consist of the organic electroluminescent device; and may be in the electron buffer layer and/or the electron transport layer, but not limited thereto; may be included as an electron buffer material when included in the electron buffer layer and may be included as an electron transport material when included in the electron transport layer.

The compound represented by formula 1 will be described in more detail as follows.

In formula 1, $Z_1$ to $Z_{11}$ each independently represent $CR_1$ or N. According to one embodiment of the present disclosure, $Z_1$ may be N, and $Z_2$ to $Z_{11}$ may all be $CR_1$. According to another embodiment of the present disclosure, $Z_4$ may be N, and $Z_1$ to $Z_3$ and $Z_5$ to $Z_{11}$ may all be $CR_1$.

$R_1$ may be hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur, preferably, hydrogen, or may be linked to an adjacent substituent to form a substituted or unsubstituted, (C5-C10) mono- or polycyclic, alicyclic or aromatic ring, or a combination of alicyclic and aromatic rings, whose carbon atom may be replaced with at least one heteroatom selected from nitrogen, oxygen, and sulfur, more preferably, hydrogen, or may be linked to an adjacent substituent to form a benzene ring or benzofuran ring.

L may be a single bond, a substituted or unsubstituted (C6-C30)arylene, or a substituted or unsubstituted (5- to 30-membered)heteroarylene, preferably a single bond, or a substituted or unsubstituted (C6-C20)arylene, more preferably a single bond, or a (C1-C6)alkyl-substituted or unsubstituted (C6-C20)arylene. Specifically, according to one embodiment of the present disclosure, L may be a single bond, phenylene, biphenylene, terphenylene or dimethylfluorenylene.

Ar may be hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)ar(C1-C30)alkyl, —N($R_{11}$)($R_{12}$), —Si($R_{13}$)($R_{14}$)($R_{15}$), —S($R_{16}$), —O($R_{17}$), cyano, nitro or hydroxyl, preferably, a substituted or unsubstituted (C6-C25)aryl, a substituted or unsubstituted (5- to 20-membered)heteroaryl, or —N($R_{11}$)($R_{12}$), more preferably, an unsubstituted (C6-C20)aryl, at least one (C6-C12)aryl-substituted or unsubstituted (5- to 20-membered)heteroaryl, or —N($R_{11}$)($R_{12}$). According to one embodiment of the present disclosure, when Ar is substituted or unsubstituted (5- to 30-membered)heteroaryl, the heteroaryl may contain at least one nitrogen atom. Specifically, according to one embodiment of the present disclosure, Ar may be fluoranthenyl; triphenylenyl; pyridyl substituted with phenyl or naphthyl; pyrimidinyl substituted with phenyl, naphthyl and/or biphenyl; triazinyl substituted with phenyl, naphthyl and/or biphenyl; quinolyl; phenyl-, naphthyl- or biphenyl-substituted or unsubstituted isoquinolyl; quinazolinyl substituted with phenyl, naphthyl or biphenyl; quinoxalinyl substituted with phenyl, naphthyl or biphenyl; naphthyridinyl substituted with phenyl; benzoquinazolinyl substituted with phenyl; benzoquinoxalinyl substituted with phenyl; or dibenzoquinoxalinyl substituted with phenyl.

$R_{11}$ to $R_{17}$ may be each independently hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur. Preferably, $R_{11}$ and $R_{12}$ may be each independently a substituted or unsubstituted (C6-C20)aryl, more preferably may be each independently (C1-C6)alkyl- or (C6-C12)aryl-substituted or unsubstituted (C6-C20)aryl. Specifically, according to one embodiment of the present disclosure, $R_{11}$ and $R_{12}$ may be each independently phenyl, biphenyl, naphthylphenyl or dimethylfluorenyl.

According to one embodiment of the present disclosure, wherein formula 1, $Z_1$ to $Z_{11}$ may be each independently $CR_1$ or N; $R_1$ may be hydrogen, or may be linked to an adjacent substituent to form a (C5-C10) mono- or polycyclic, alicyclic or aromatic ring, or a combination of alicyclic and aromatic rings, whose carbon atom may be replaced with at least one heteroatom selected from nitrogen, oxygen, and sulfur; L may be a single bond, or a substituted or unsubstituted (C6-C20)arylene; Ar may be a substituted or unsubstituted (C6-C25)aryl, a substituted or unsubstituted (5- to 25-membered)heteroaryl, or —$N(R_{11})(R_{12})$.

According to another embodiment of the present disclosure, wherein formula 1, $Z_1$ to $Z_{11}$ may be each independently $CR_1$ or N; $R_1$ may be hydrogen, or may be linked to an adjacent substituent to form a benzene ring or a benzofuran ring; L may be a single bond, or a (C1-C6)alkyl-substituted or unsubstituted (C6-C20)arylene; Ar may be an unsubstituted (C6-C20)aryl, at least one (C6-C12)aryl-substituted or unsubstituted (5- to 20-membered)heteroaryl, or —$N(R_{11})(R_{12})$.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having 3 to 7 ring backbone atoms, preferably 5 to 7 ring backbone atoms and at least one heteroatom selected from the group consisting of B, N, O, S, Si, and P, preferably O, S, and N, and includes tetrahydrofuran, pyrrolidine, thiolan, tetrahydropyran, etc. "(C6-C30)aryl(ene)" is a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18. The aryl includes those having a spiro structure, and includes phenyl, biphenyl, terphenyl, naphthyl, binaphthyl, phenylnaphthyl, naphthylphenyl, phenyl terphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(5- to 30-membered)heteroaryl(ene)" is an aryl group having at least one heteroatom selected from the group consisting of B, N, O, S, Si, and P, and 5 to 30 ring backbone atoms; having preferably 1 to 4 heteroatoms, and may be a monocyclic ring, or a fused ring condensed with at least one benzene ring; may be partially saturated; may be one formed by linking at least one heteroaryl or aryl group to a heteroaryl group via a single bond(s); may comprise those having a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. "Halogen" includes F, Cl, Br, and I.

In addition, "substituted" in the expression "substituted or unsubstituted" means that a hydrogen atom in a certain functional group is replaced with another atom or another functional group, i.e. a substituent. The substituents of the substituted (C1-C30)alkyl, the substituted (C6-C30)aryl (ene), the substituted (5- to 30-membered)heteroaryl(ene), the substituted (3- to 7-membered)heterocycloalkyl, the substituted (C3-C30)cycloalkyl, the substituted (C6-C30)ar (C1-C30)alkyl, and the substituted (C3-C30) mono- or polycyclic, alicyclic or aromatic ring, or the combination thereof, in $R_1$, L, Ar, and $R_{11}$ to $R_{17}$, are each independently at least one selected from the group consisting of deuterium; halogen; cyano; carboxyl; nitro; hydroxy; (C1-C30)alkyl; halo (C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered) heterocycloalkyl; (C6-C30)aryloxy; (C6-C30)arylthio; a (C6-C30)aryl-substituted or unsubstituted (5- to 30-membered)heteroaryl; a (5- to 30-membered)heteroaryl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; a mono- or di-(C1-C30)alkylamino; a (C1-C30)alky-substituted or unsubstituted mono- or di-(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl, preferably, at least one selected from the group consisting of (C1-C6)alkyl or (C6-C20)aryl, specifically, methyl, phenyl, naphthyl or biphenyl.

The compound represented by formula 1 may be illustrated by the following compounds, but is not limited thereto:

C-1
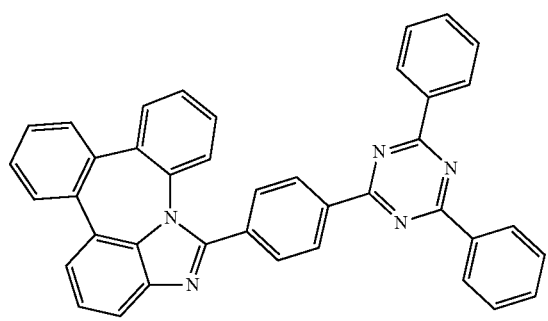
C-2
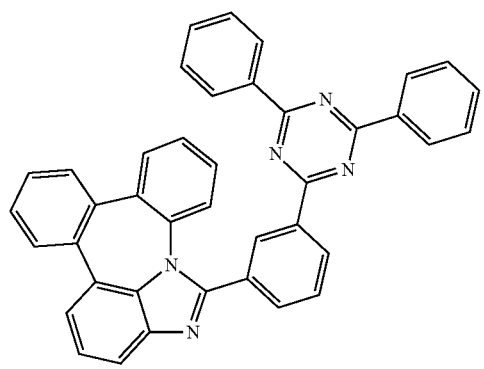
C-3
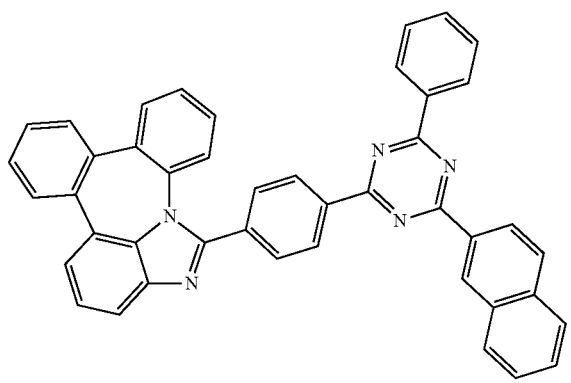
C-4
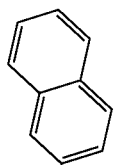
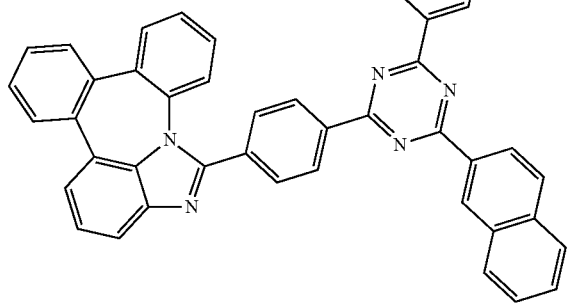
C-5
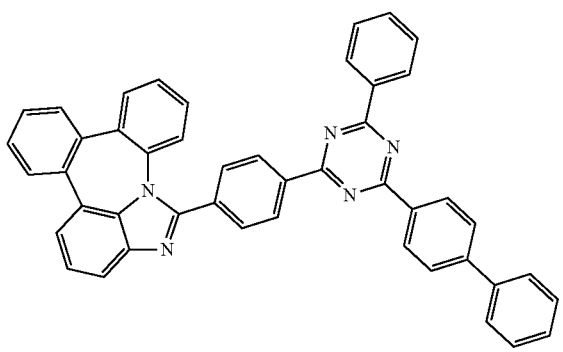
C-6
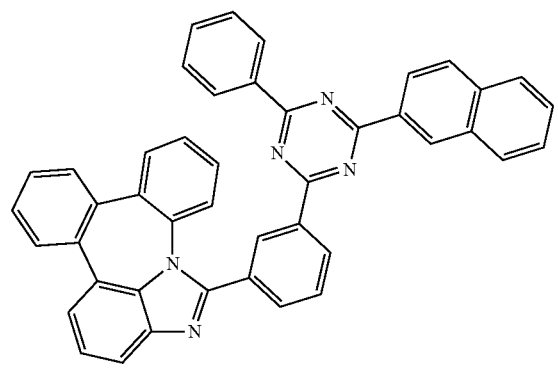
C-7
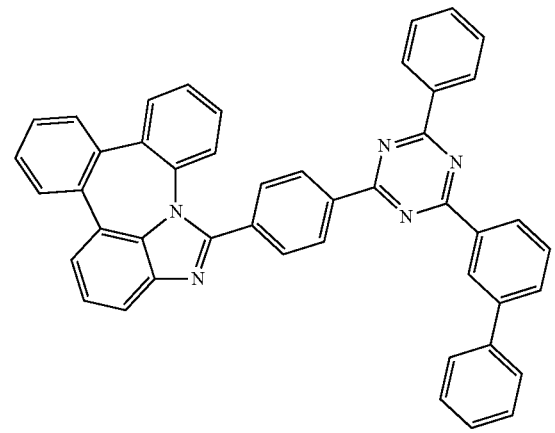
C-8
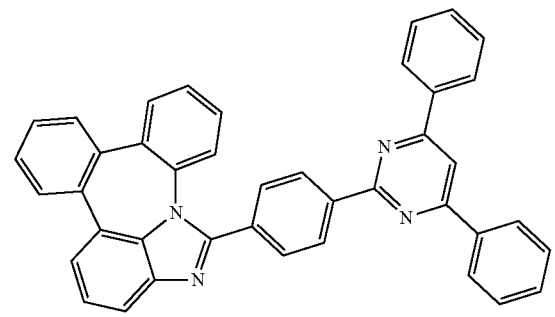

C-9
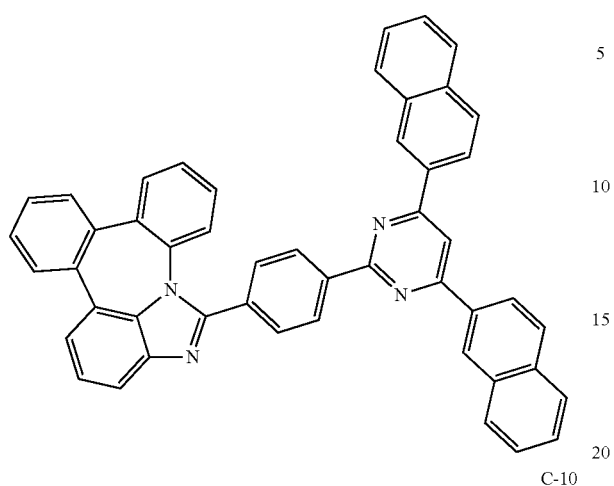
C-13
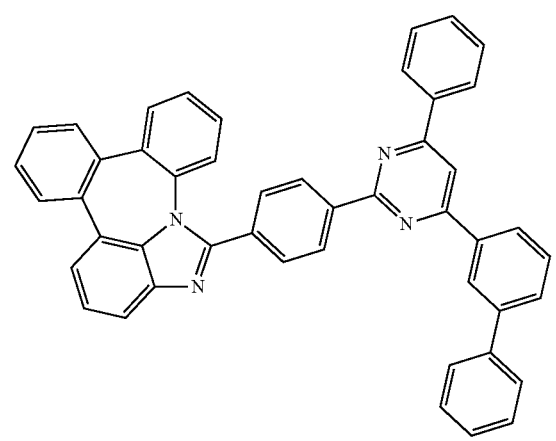
C-10
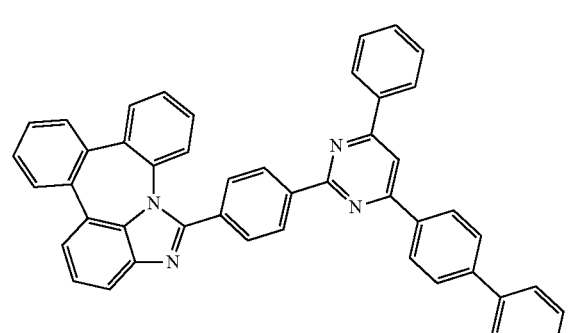
C-14
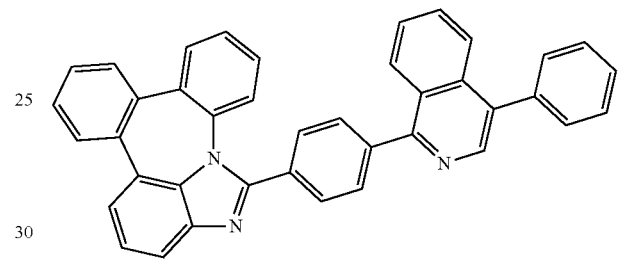
C-11
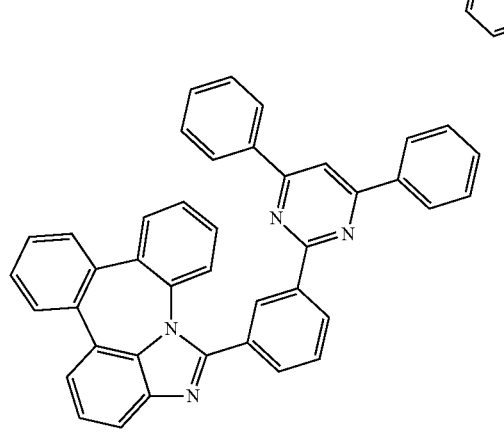
C-15
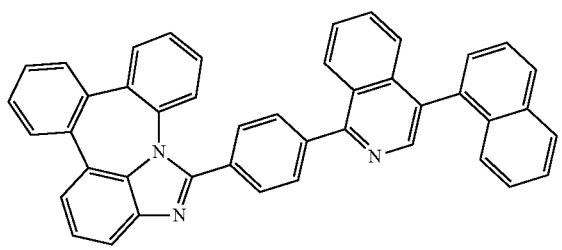
C-12
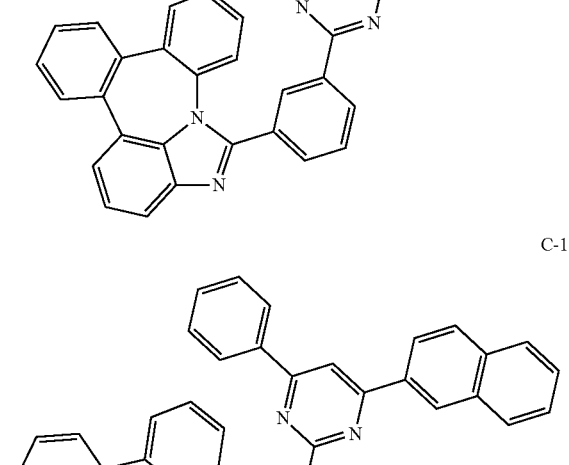
C-16
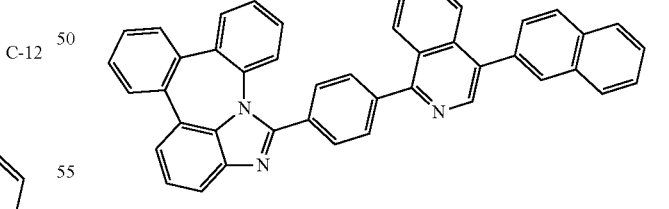
C-17
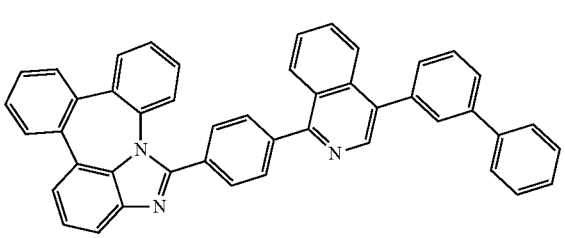
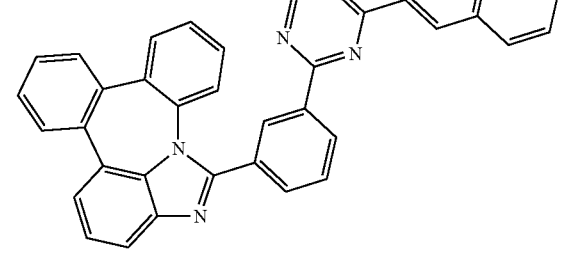

C-18
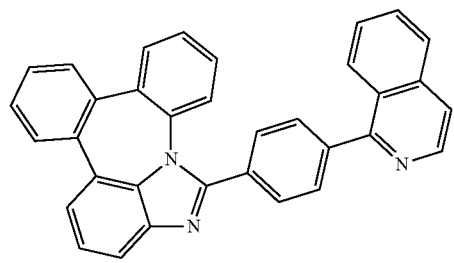
C-19
C-20
C-21
C-22
C-23
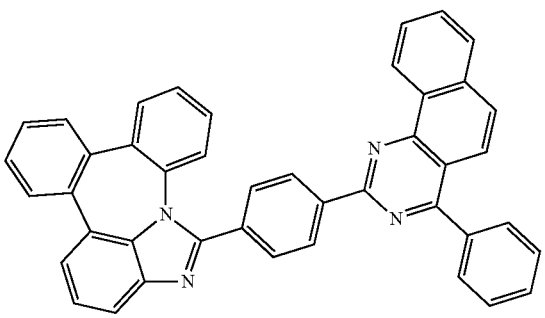
C-24
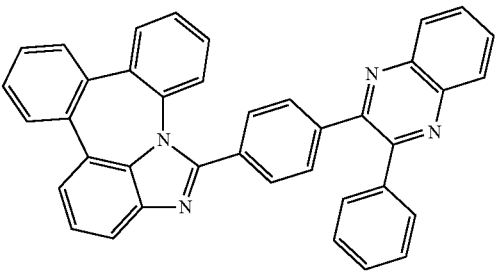
C-25
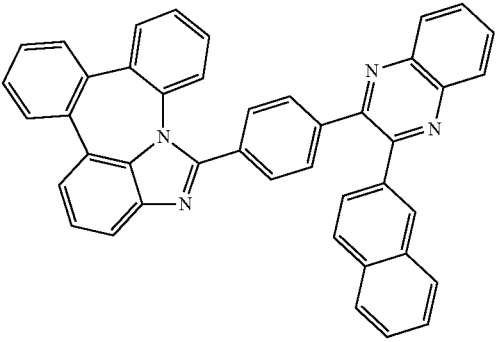
C-26
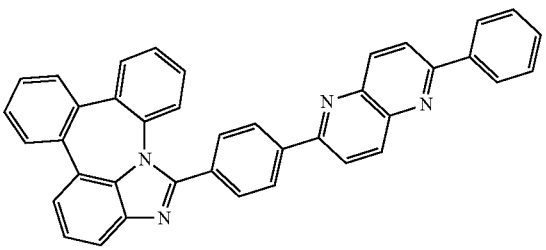
C-27
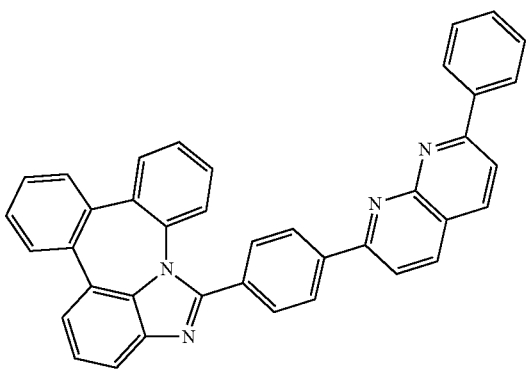

C-28
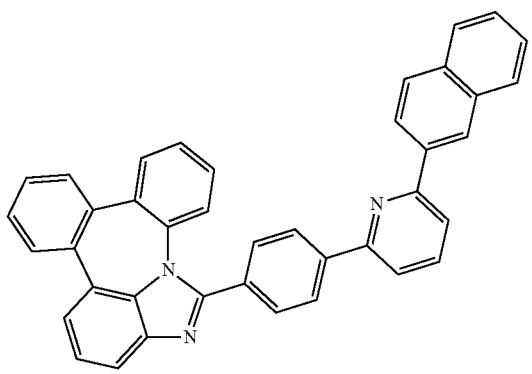
C-29
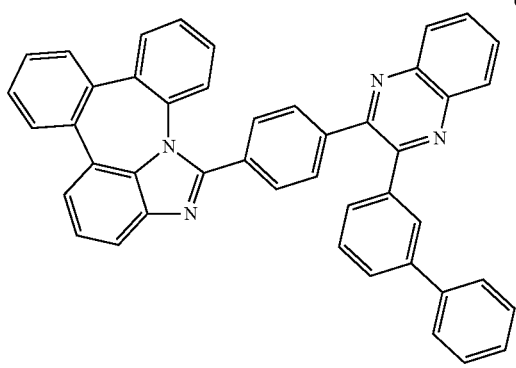
C-30
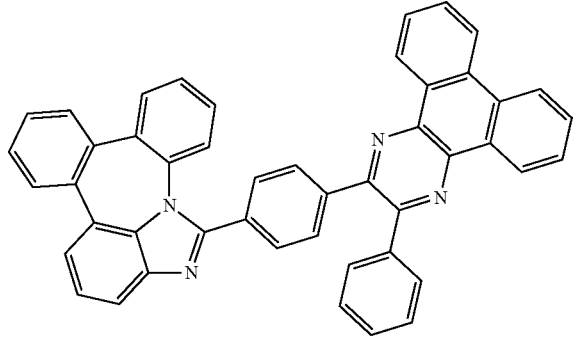
C-31
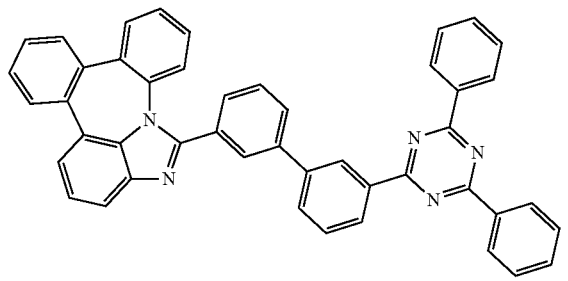
C-32
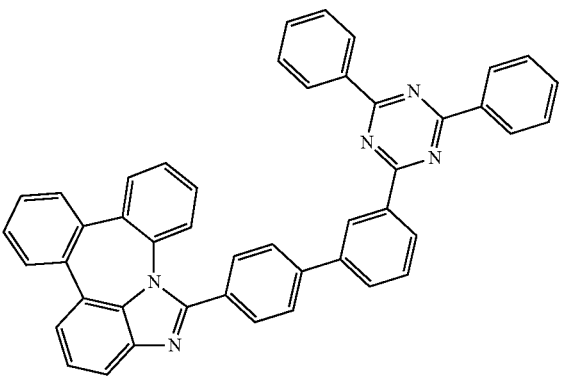
C-33
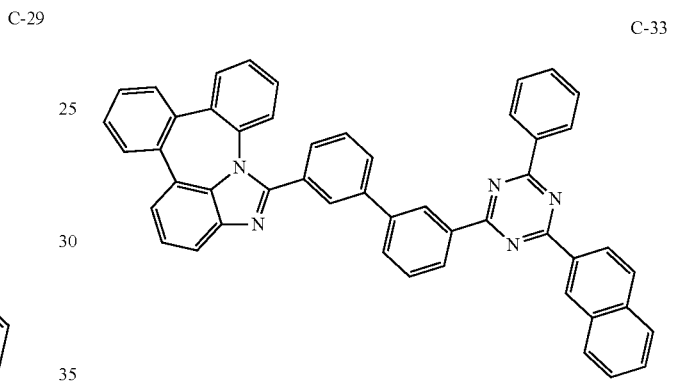
C-34
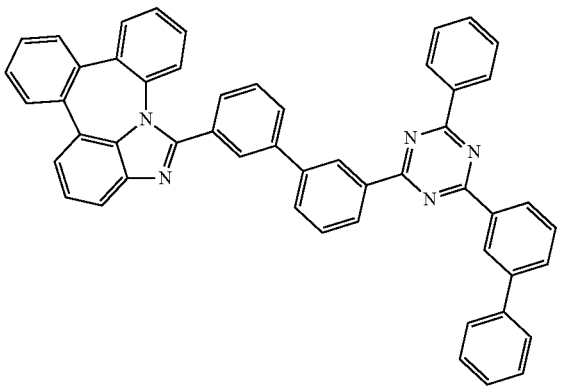
C-35
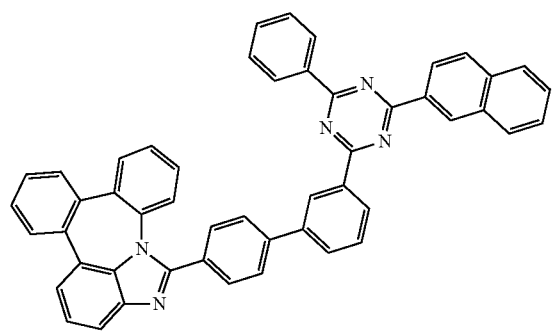

-continued
C-36
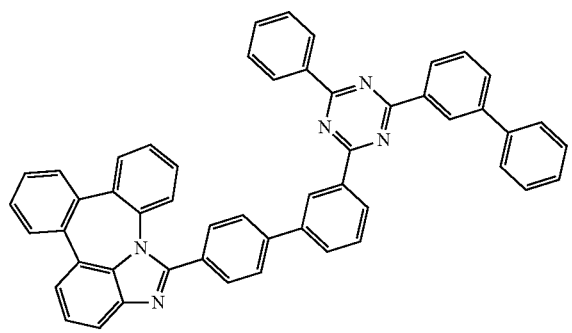
C-40
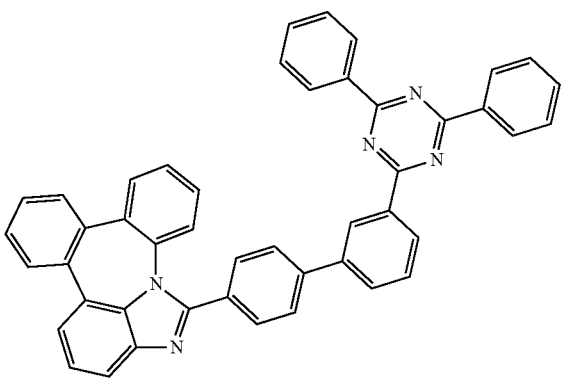
C-37
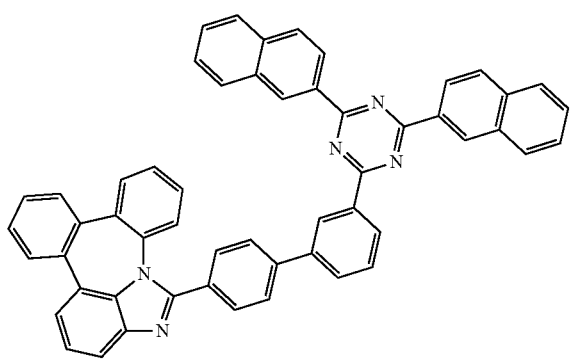
C-41
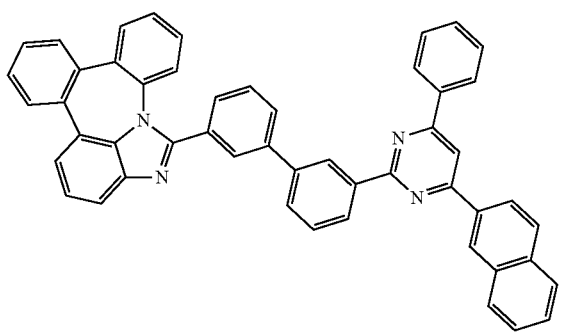
C-38
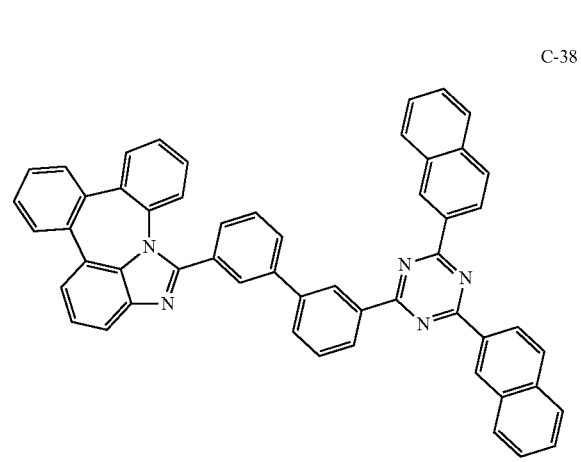
C-42
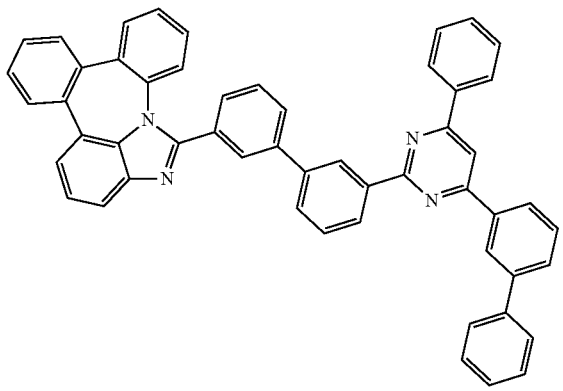
C-39
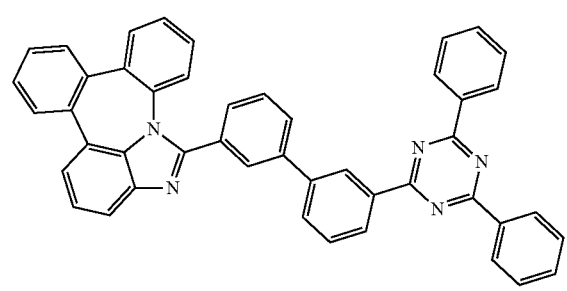
C-43
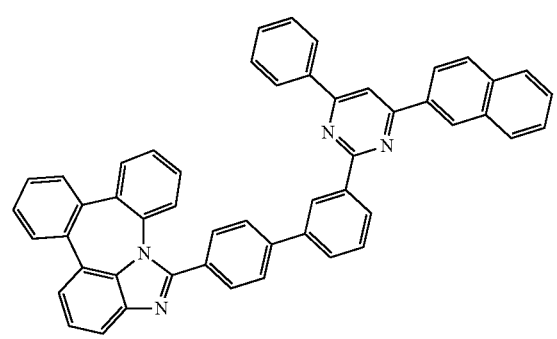

-continued
C-44
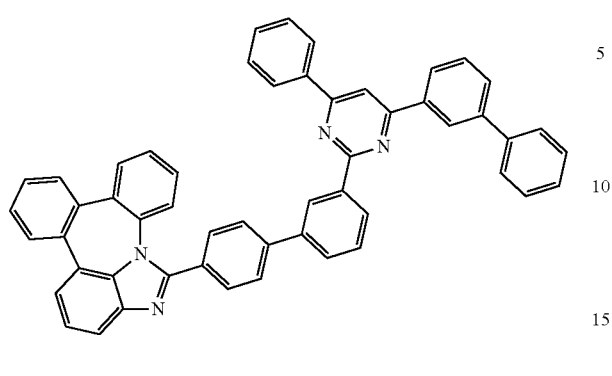
C-45
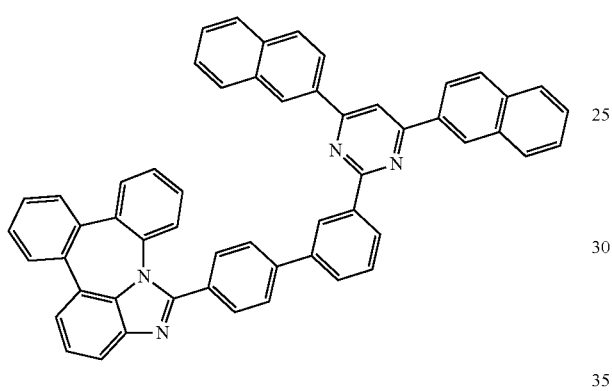
C-46
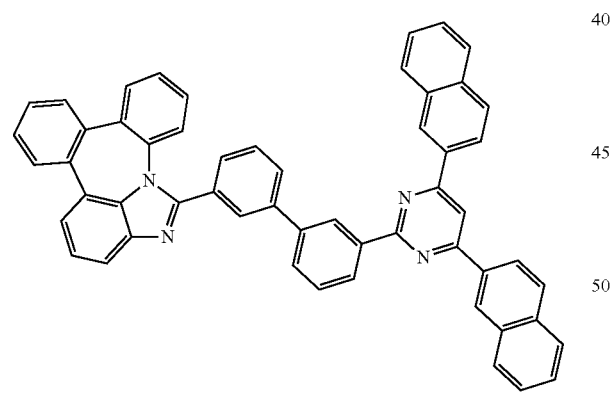
C-47
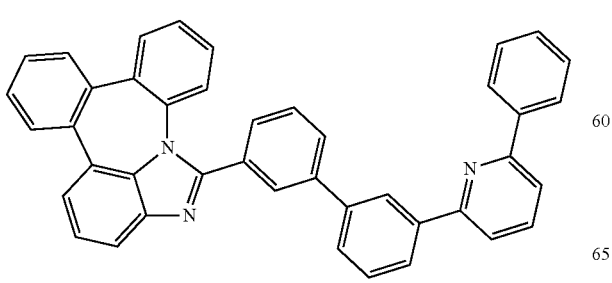
-continued
C-48
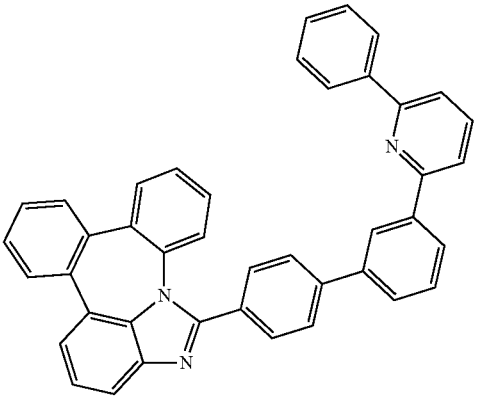
C-49
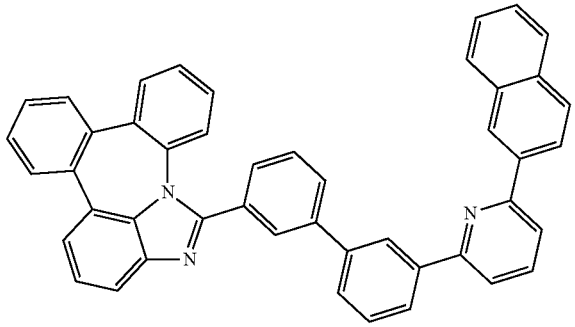
C-50
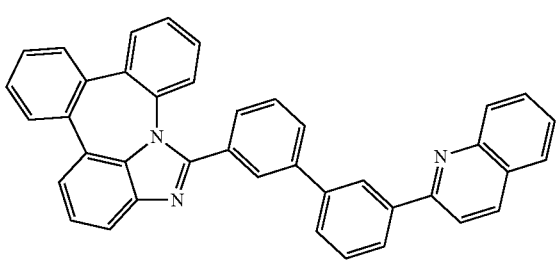
C-51
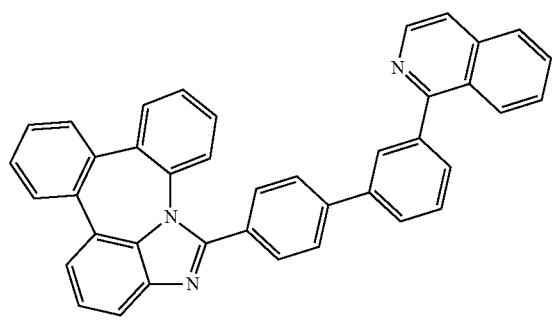

C-52
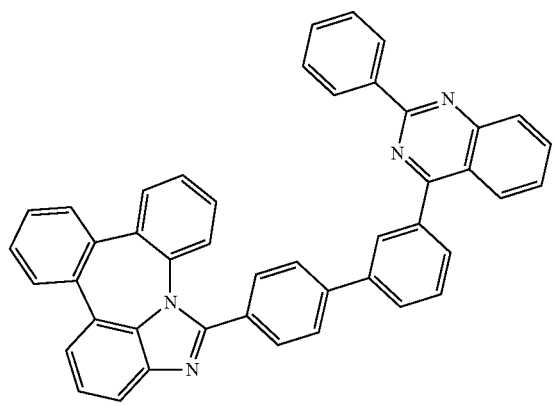
C-53
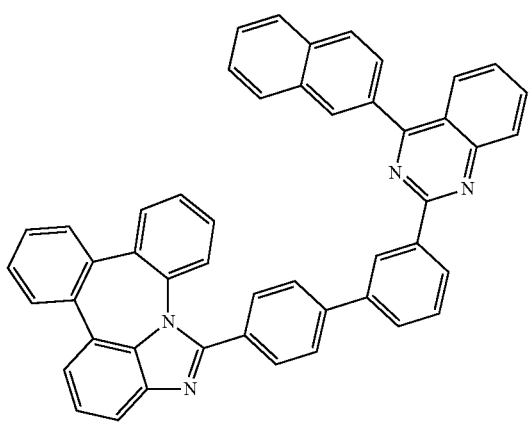
C-54
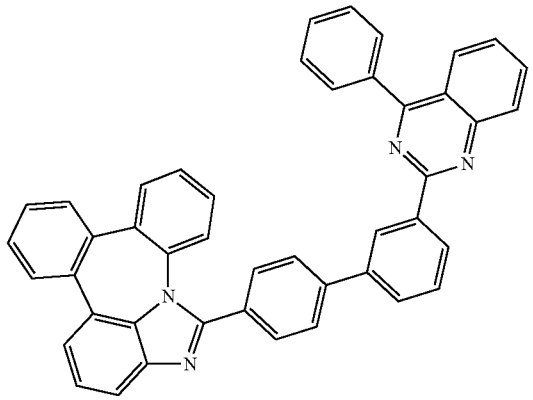
C-55
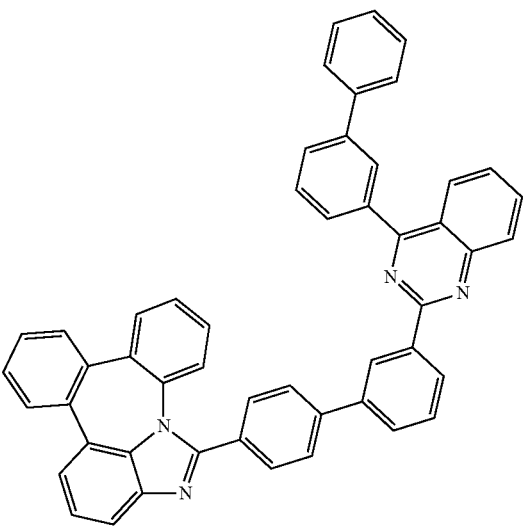
C-56
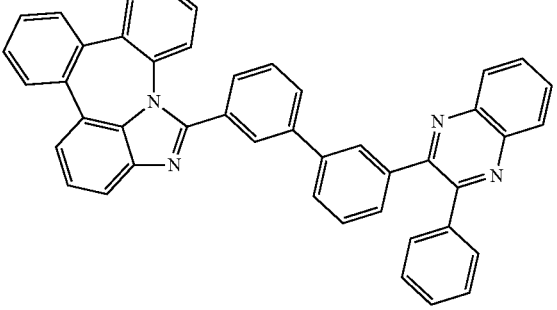
C-57
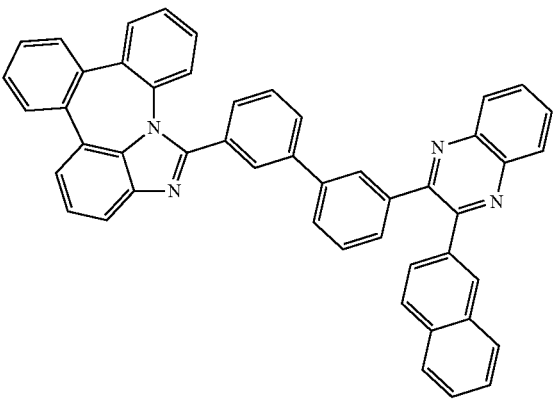

-continued
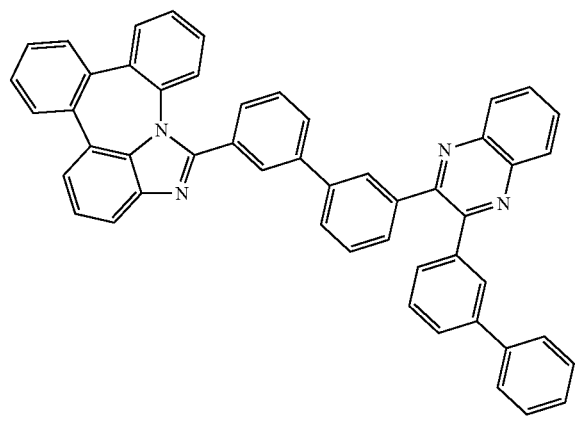
C-58
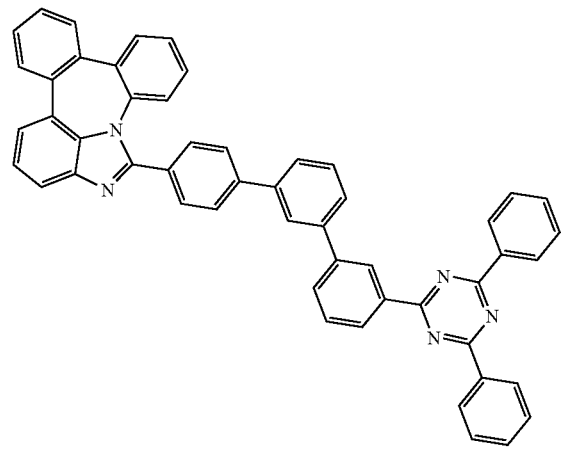
C-61
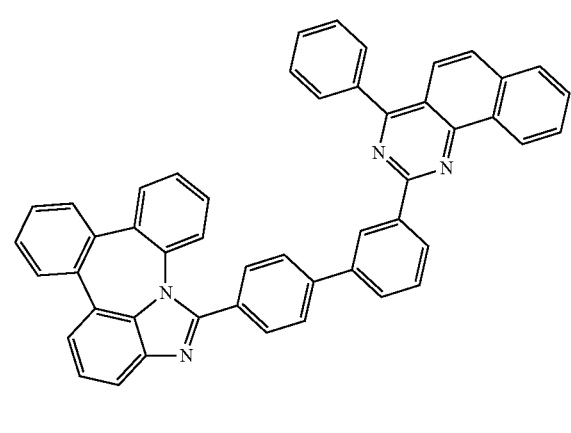
C-59
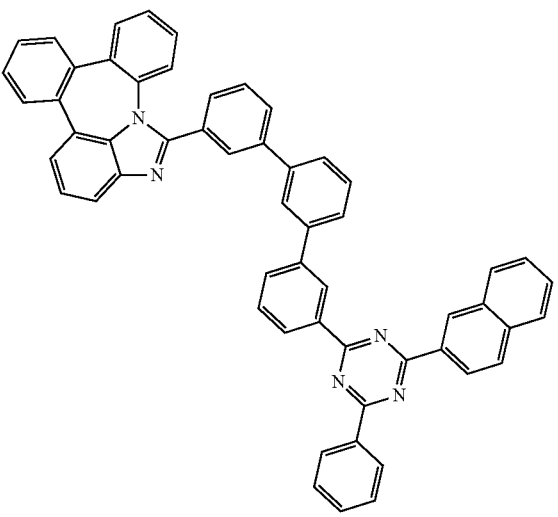
C-62
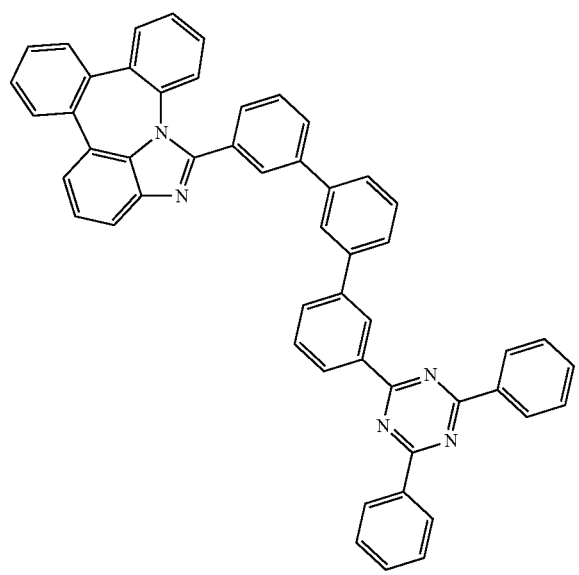
C-60
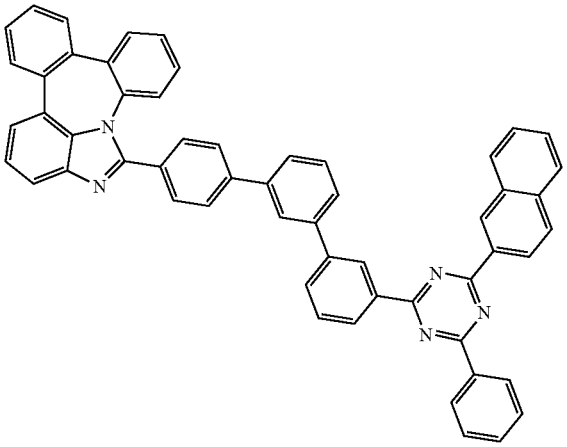
C-63

C-64
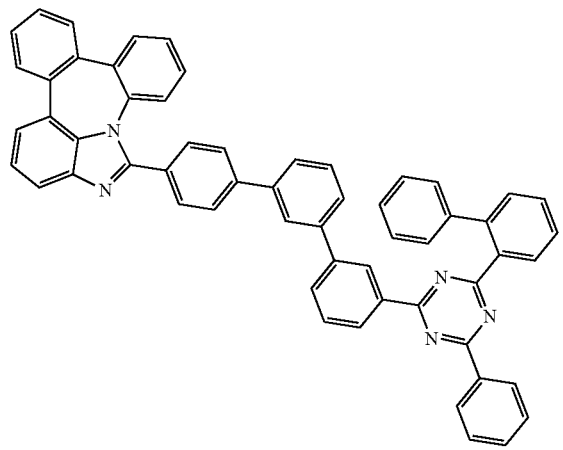
C-65
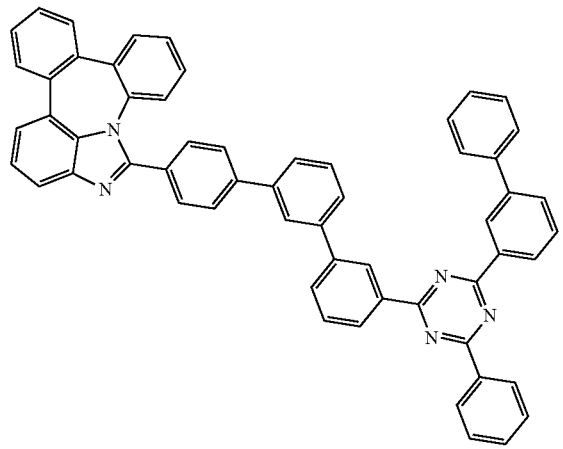
C-66
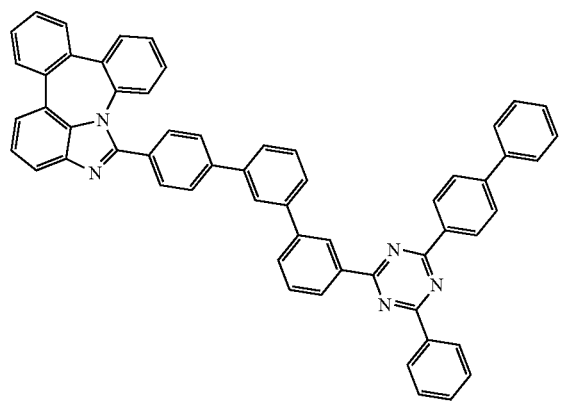
C-67
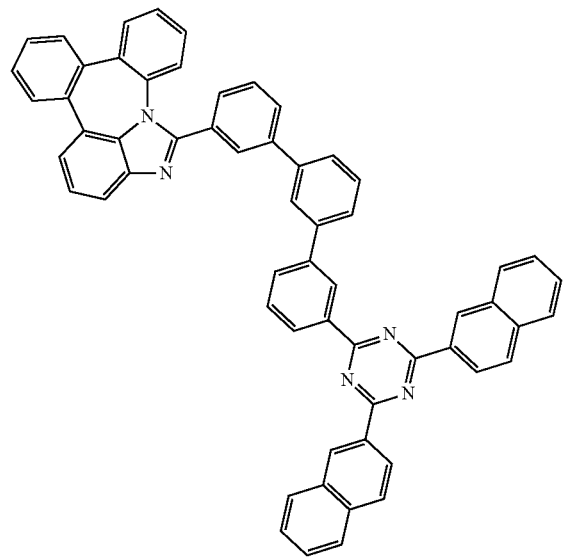
C-68
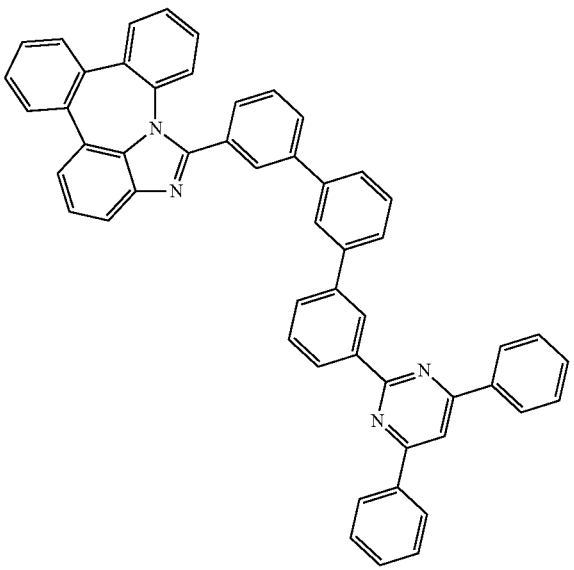
C-69
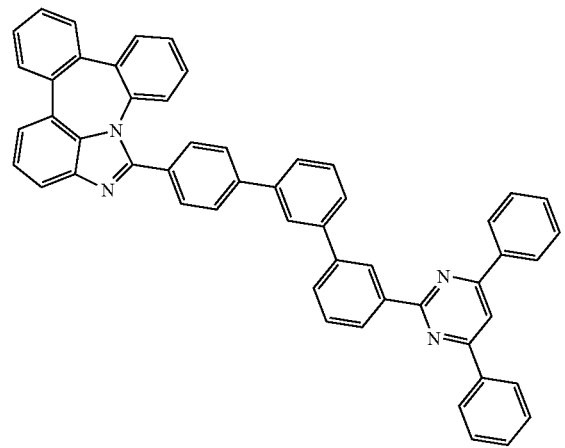

C-70
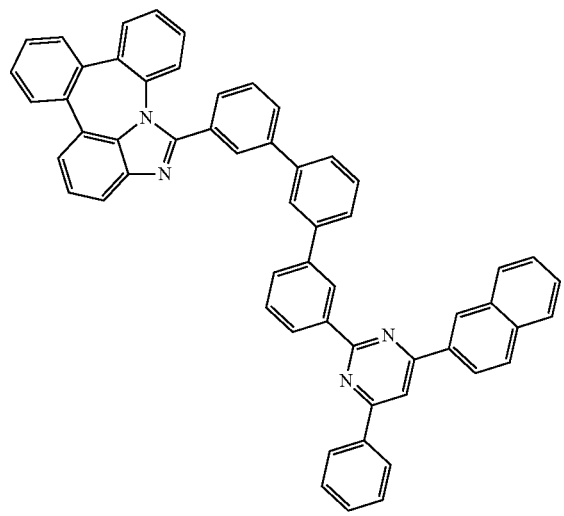
C-71
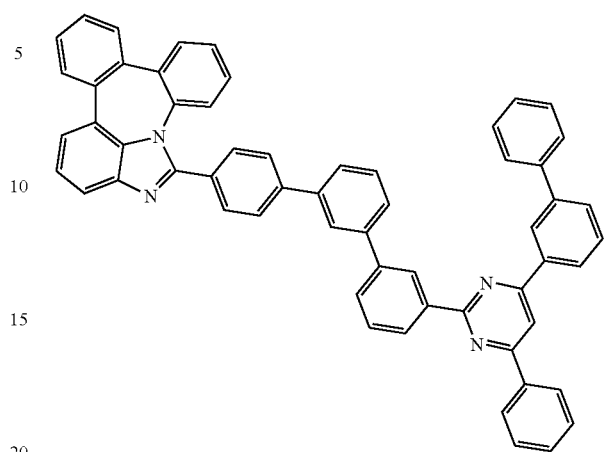
C-72
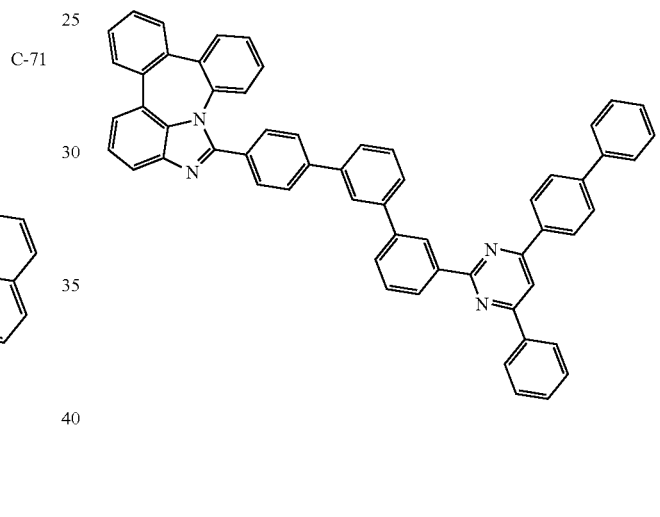
C-73
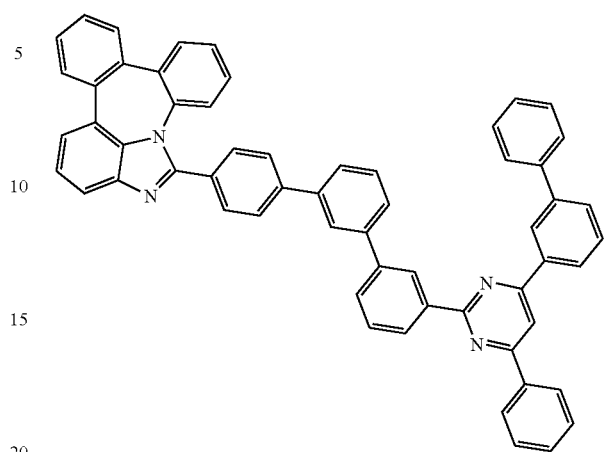
C-74
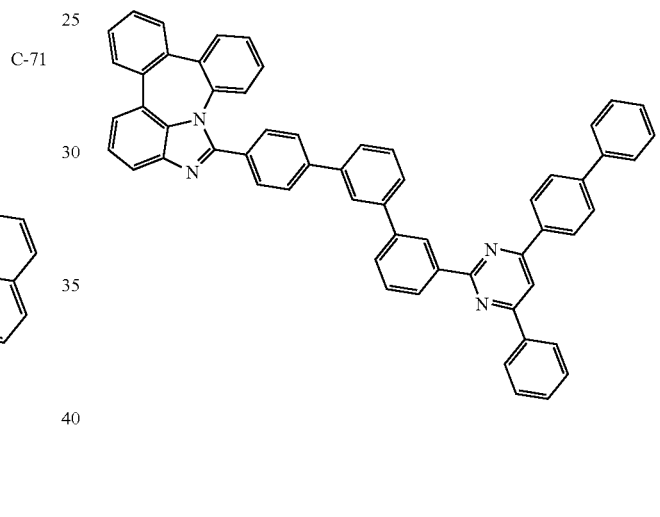
C-75
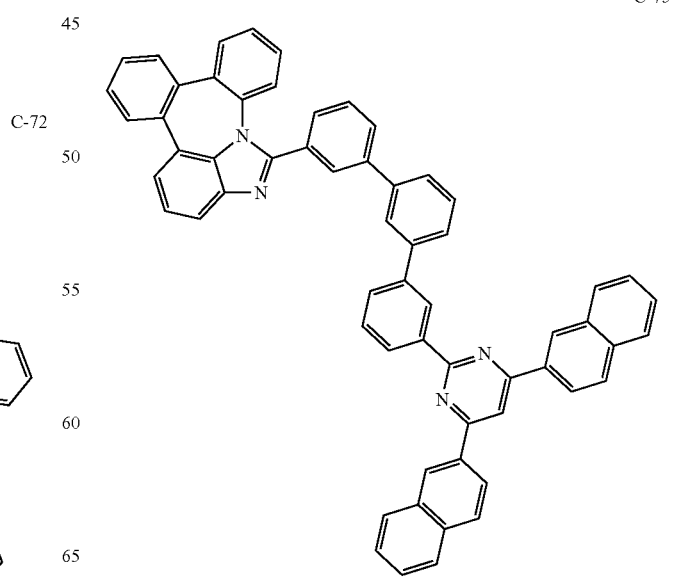

C-76
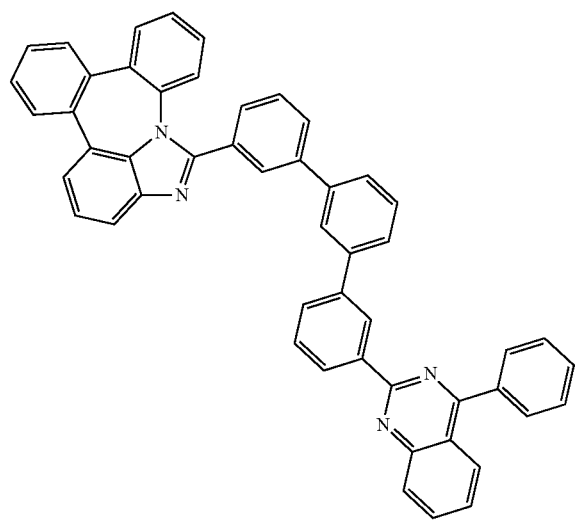
C-77
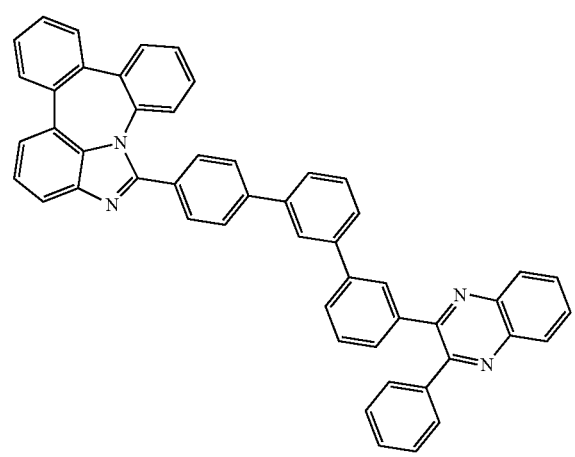
C-78
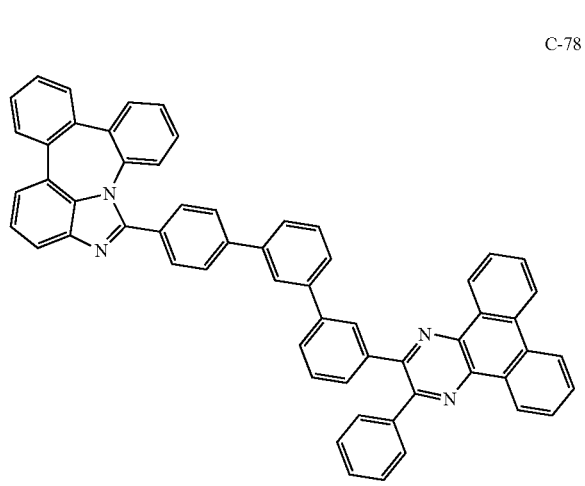
C-79
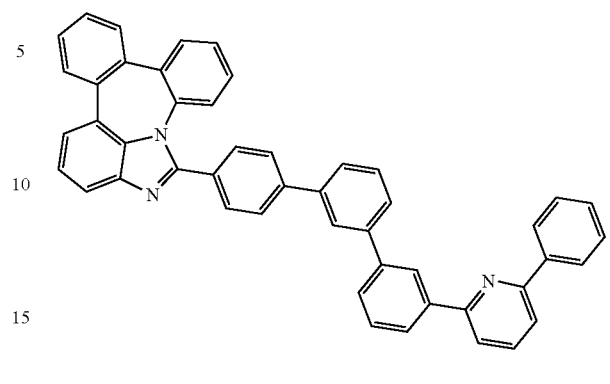
C-80
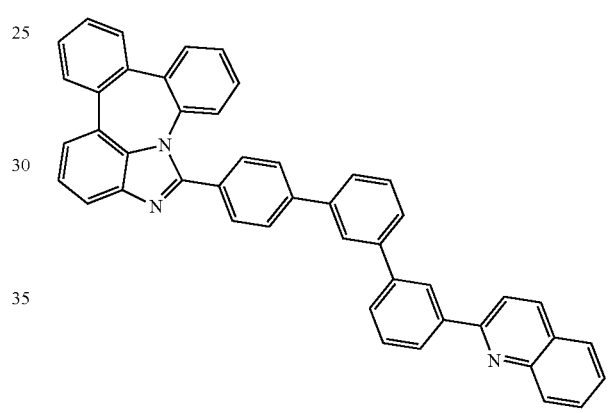
C-81
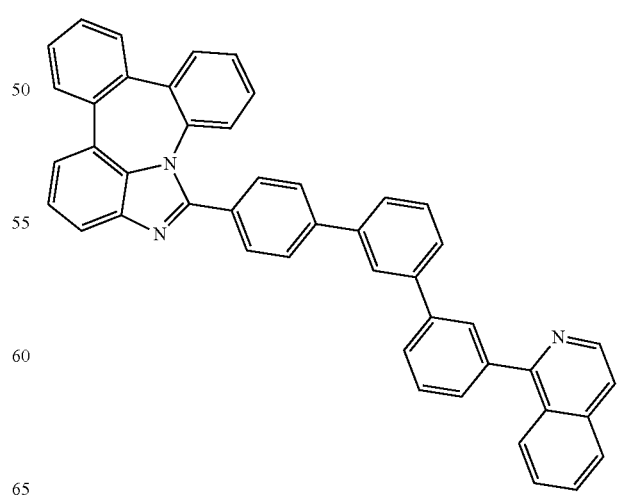

-continued
C-82
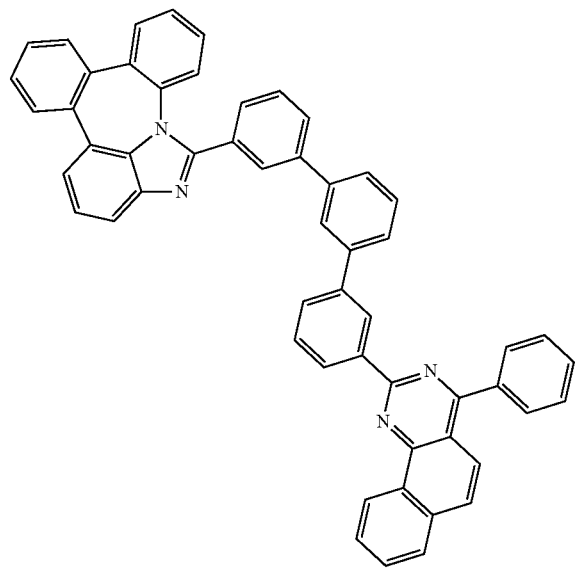
C-83
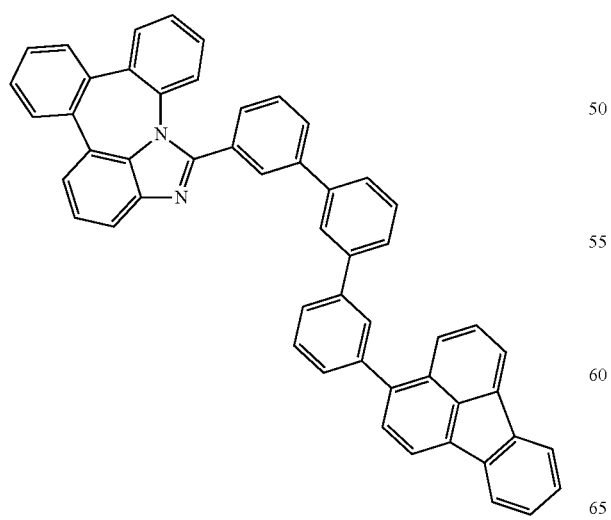
C-84
C-85
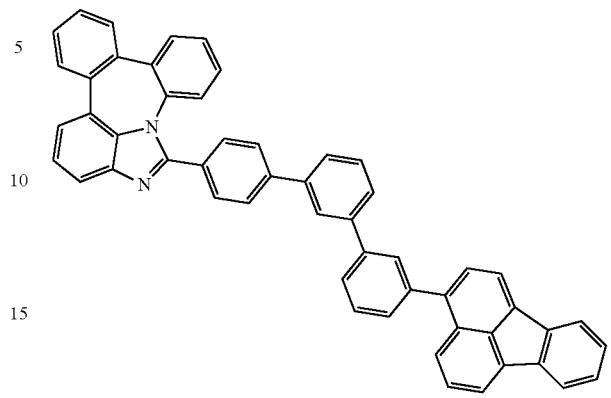
C-86
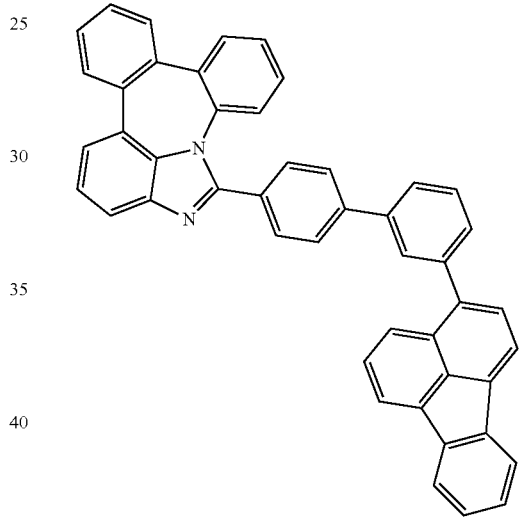
C-87
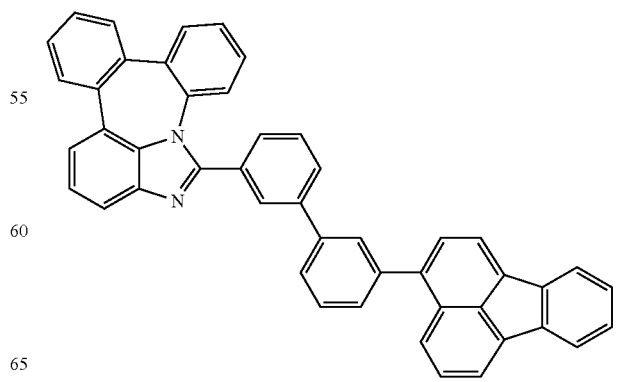

C-88
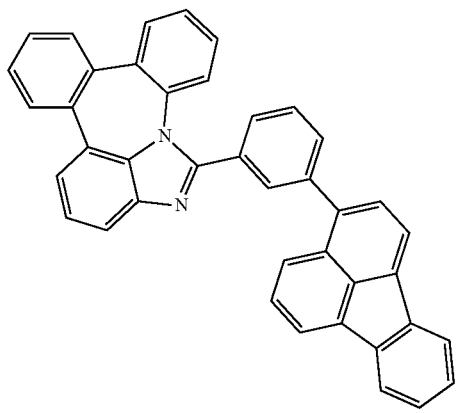
C-89
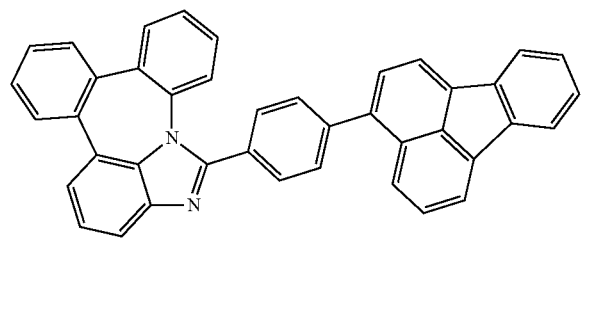
C-90
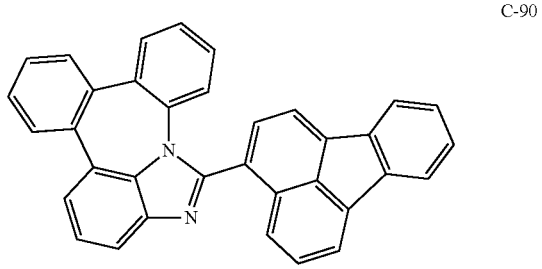
C-91
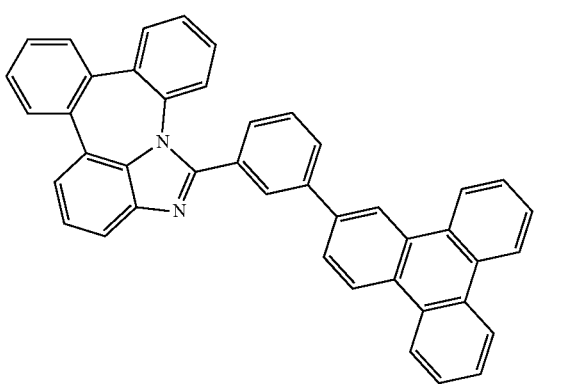
C-92
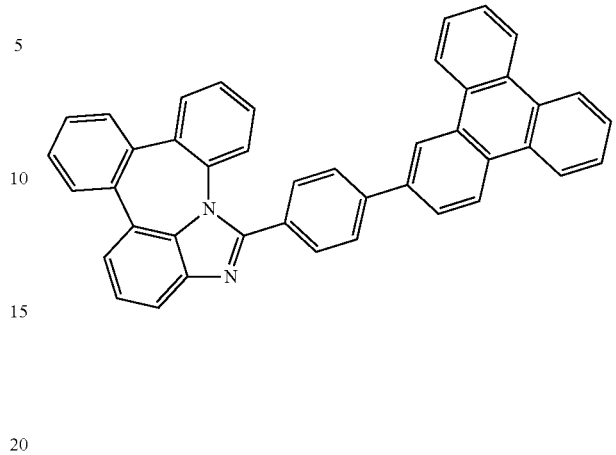
C-93
C-94

-continued
C-95
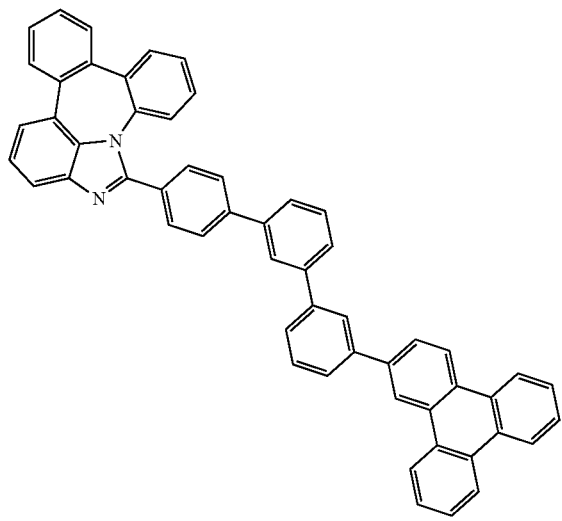
C-96
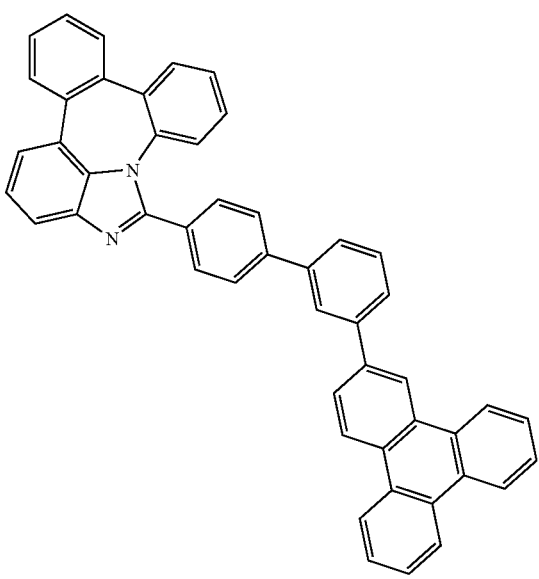
C-97
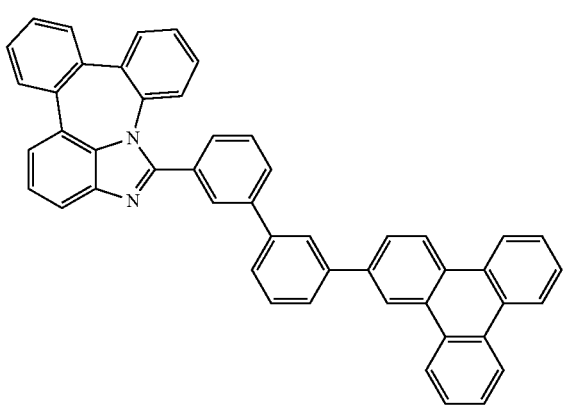
-continued
C-98
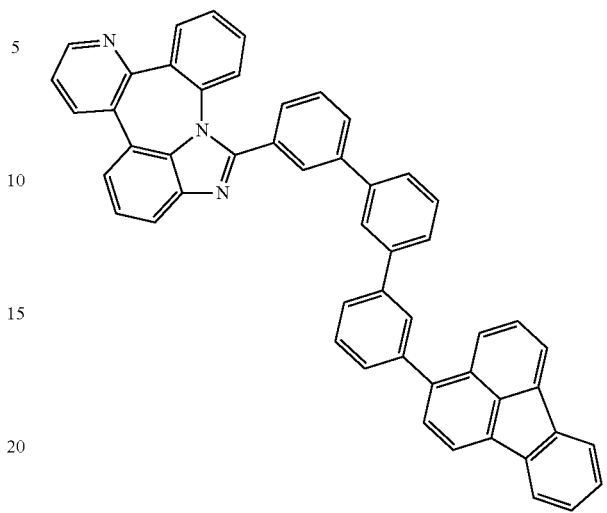
C-99
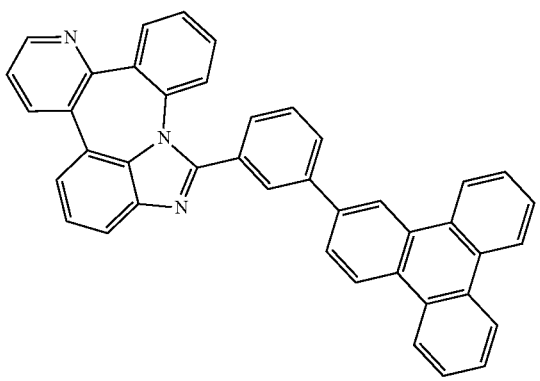
C-100
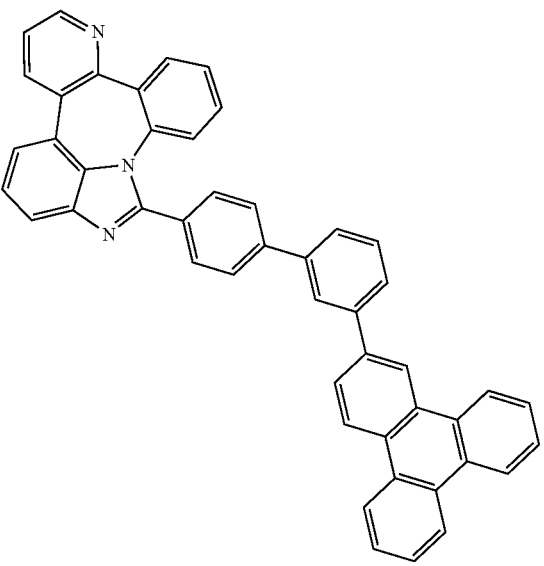

C-101
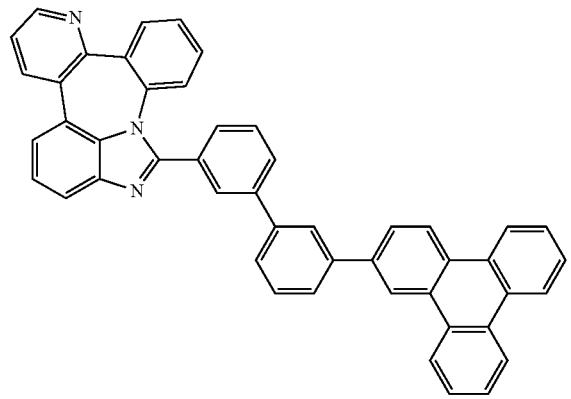
C-102
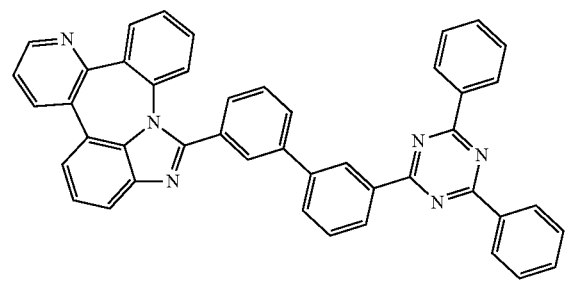
C-103
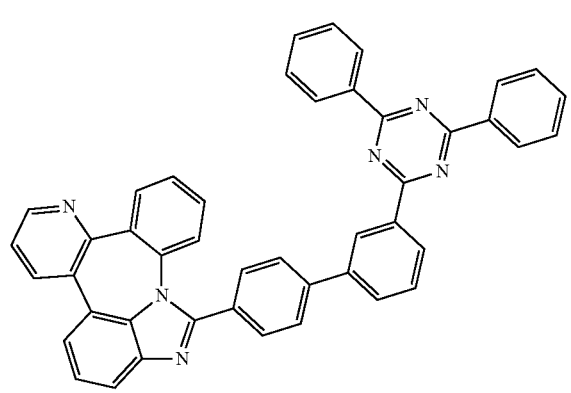
C-104
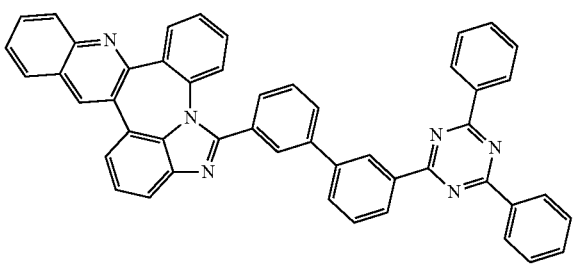
C-105
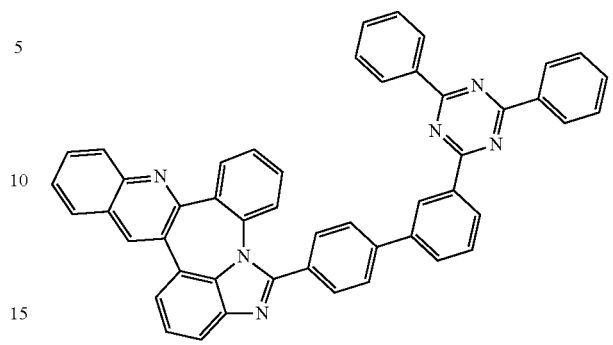
C-106
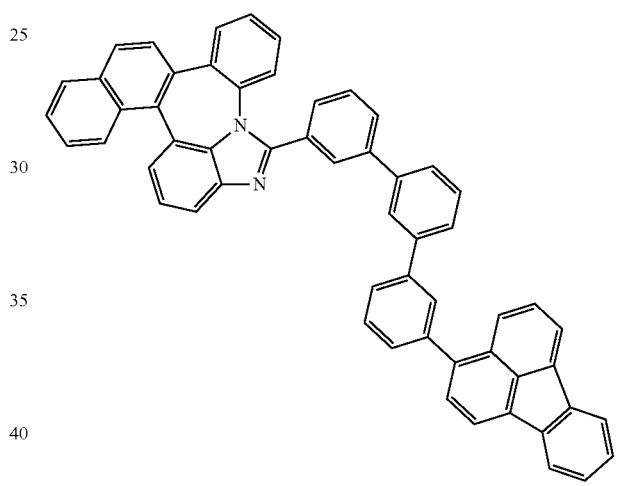
C-107
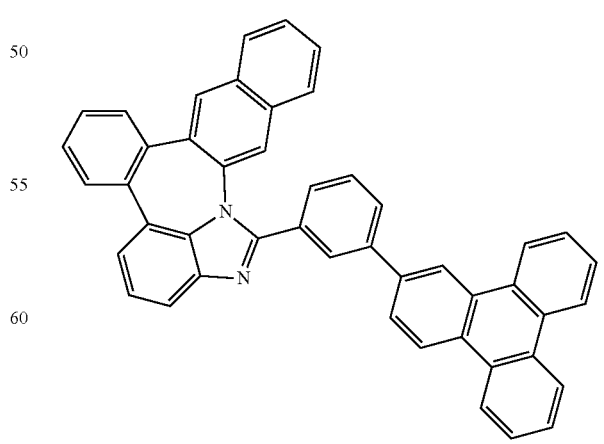

C-108
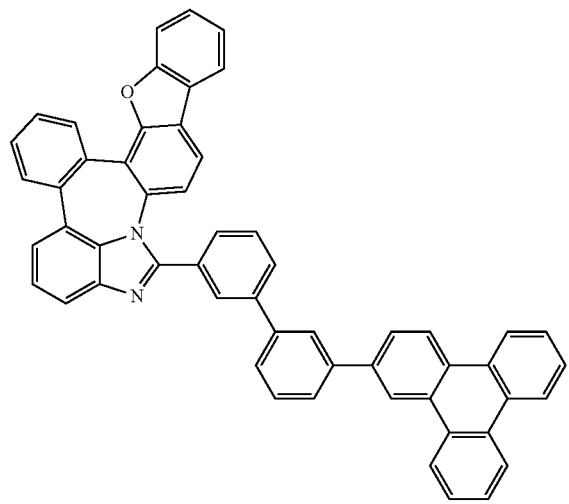
C-109
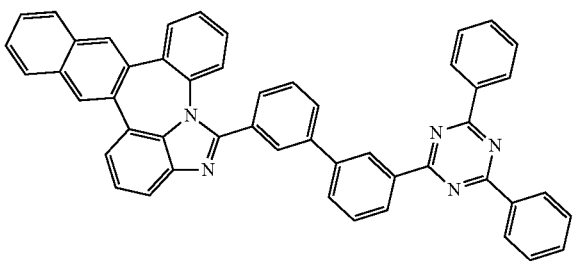
C-110
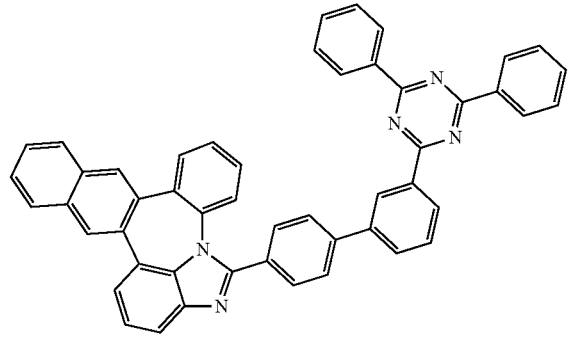
C-111
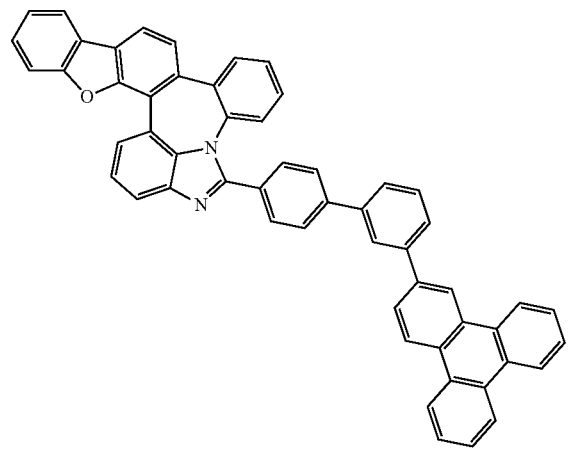
C-112
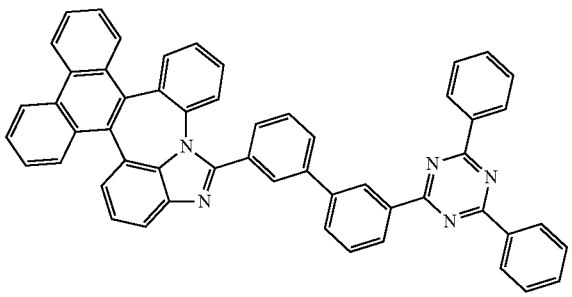
C-113
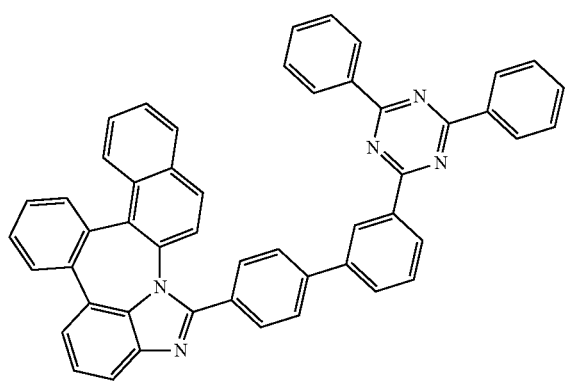
C-114
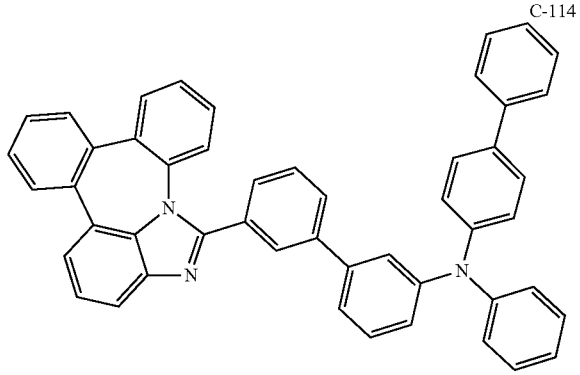
C-115
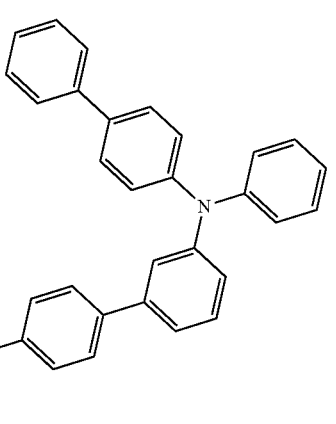

C-116
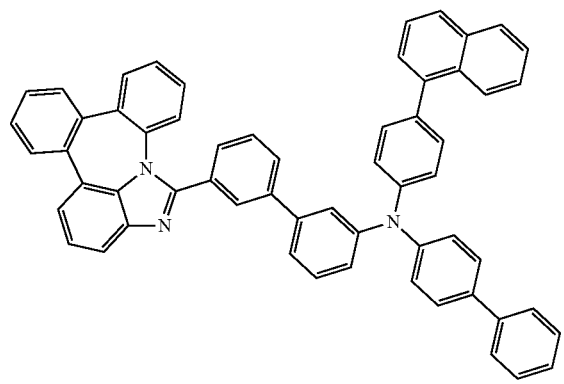
C-120
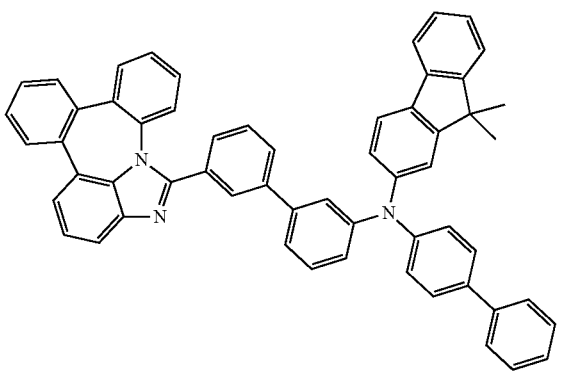
C-117
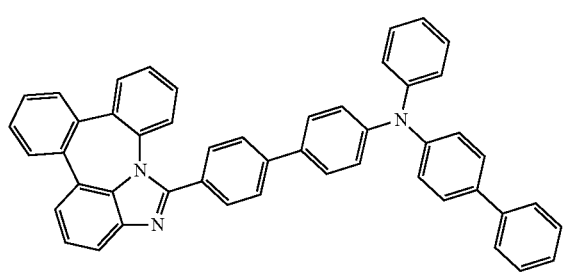
C-118
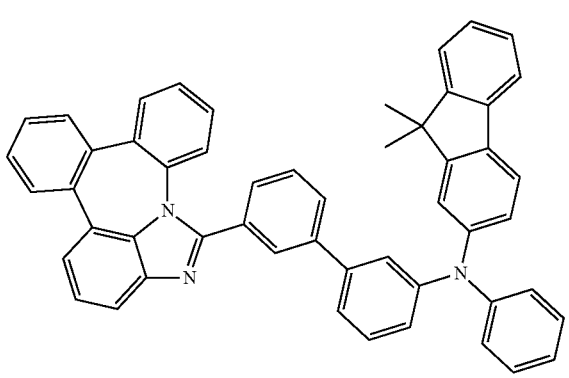
C-121
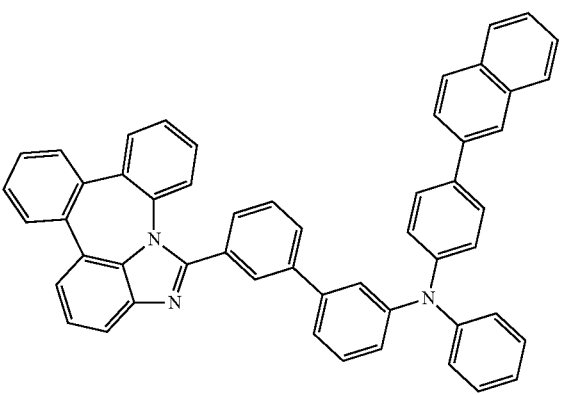
C-119
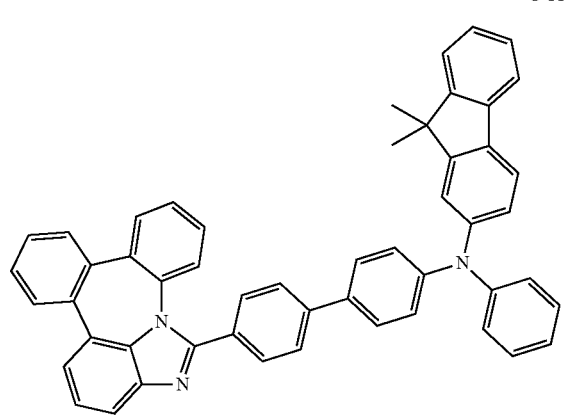
C-122

C-123
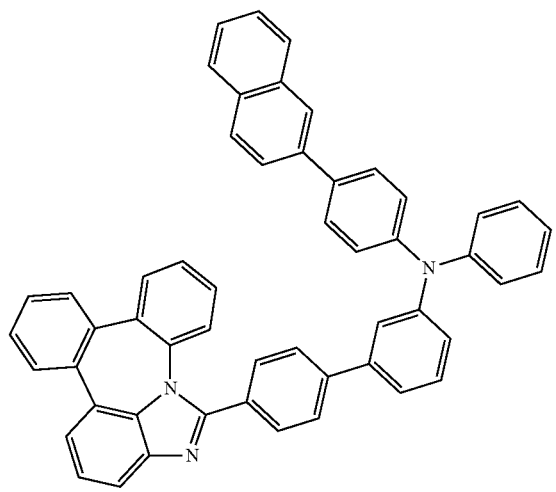
C-124
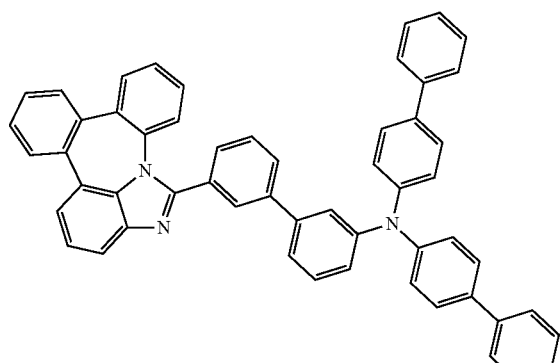
C-125
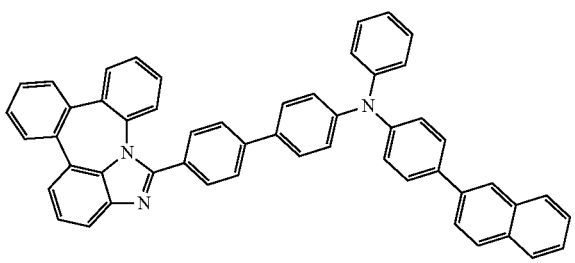
C-126
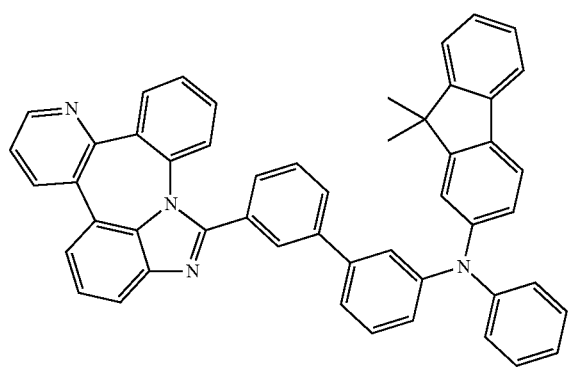
C-127
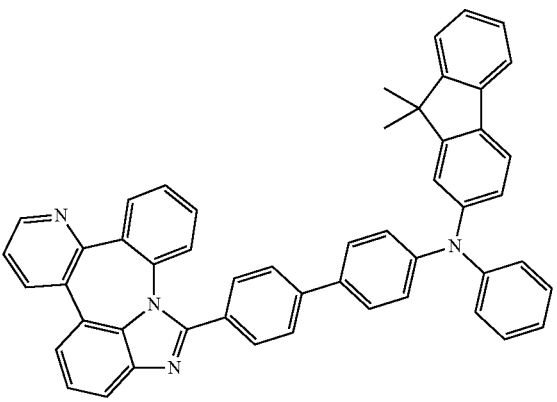
C-128
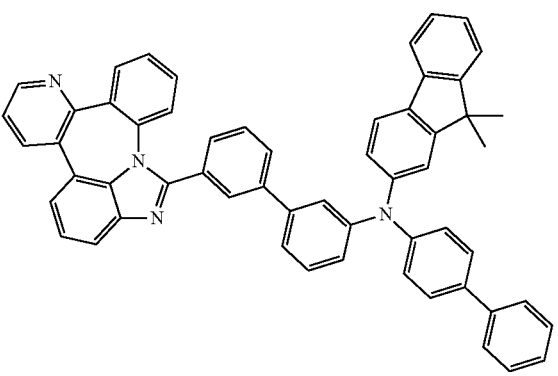
C-129
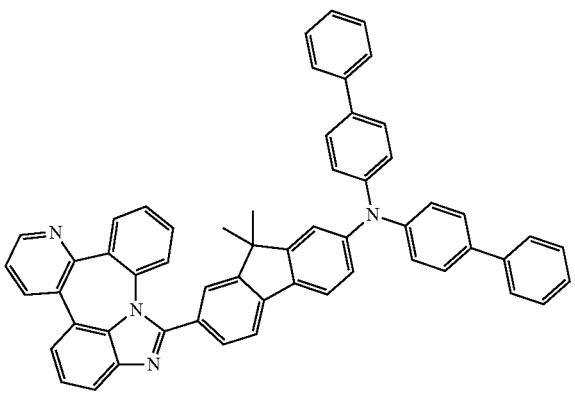
C-130
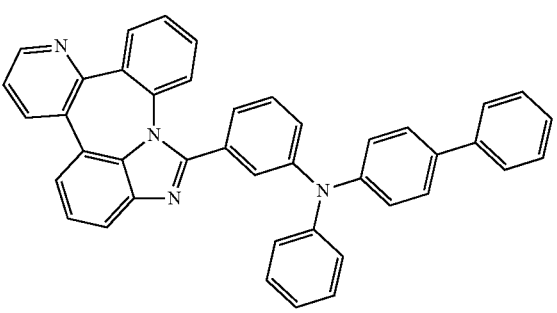

C-131
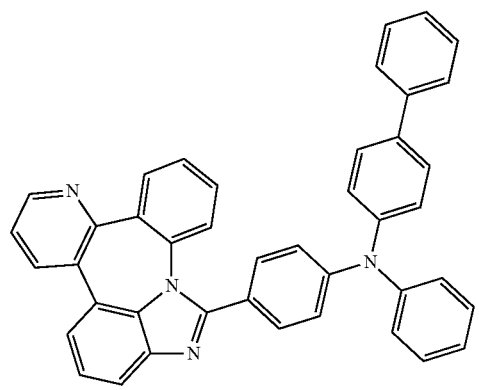
C-132
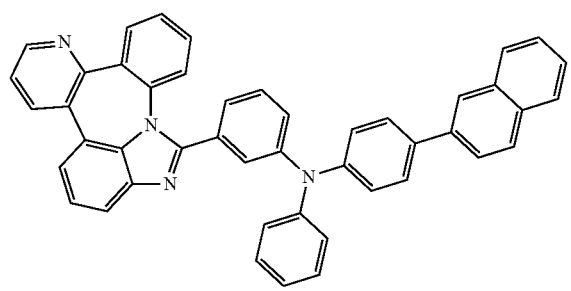
C-133
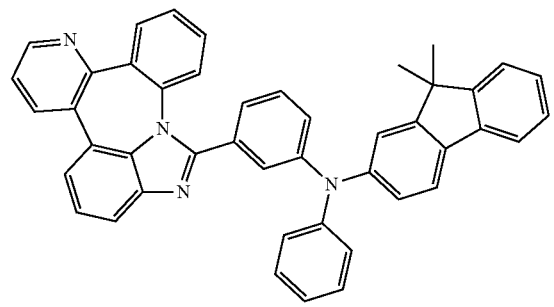
C-134
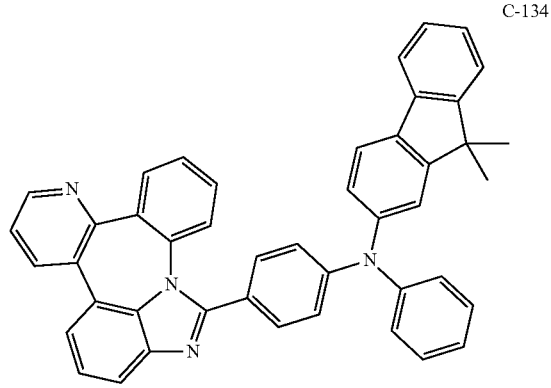
C-135
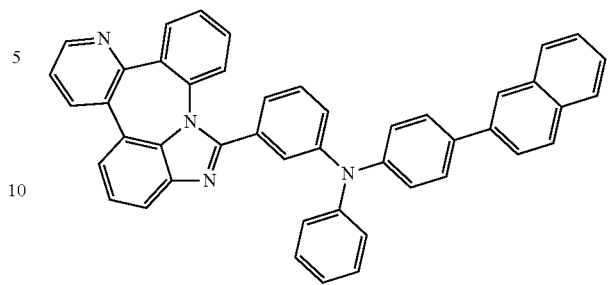
C-136
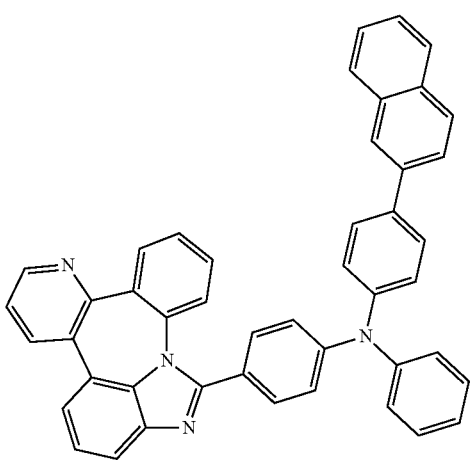
C-137
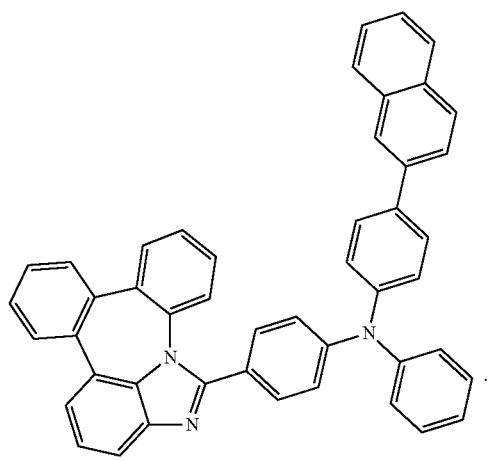
The compounds of formula 1 according to the present disclosure can be prepared by a synthetic method known to one skilled in the art, for example, as shown in the following reaction scheme.
[Reaction Scheme 1]
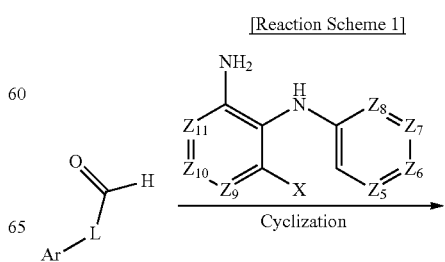

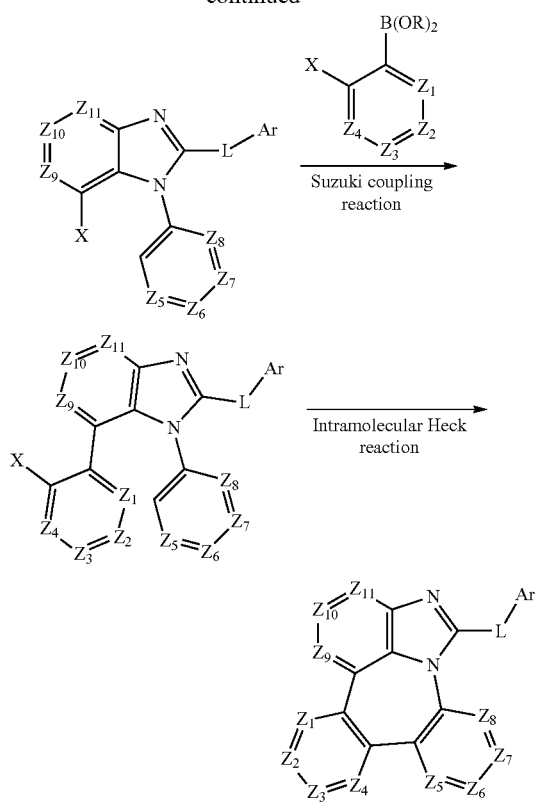

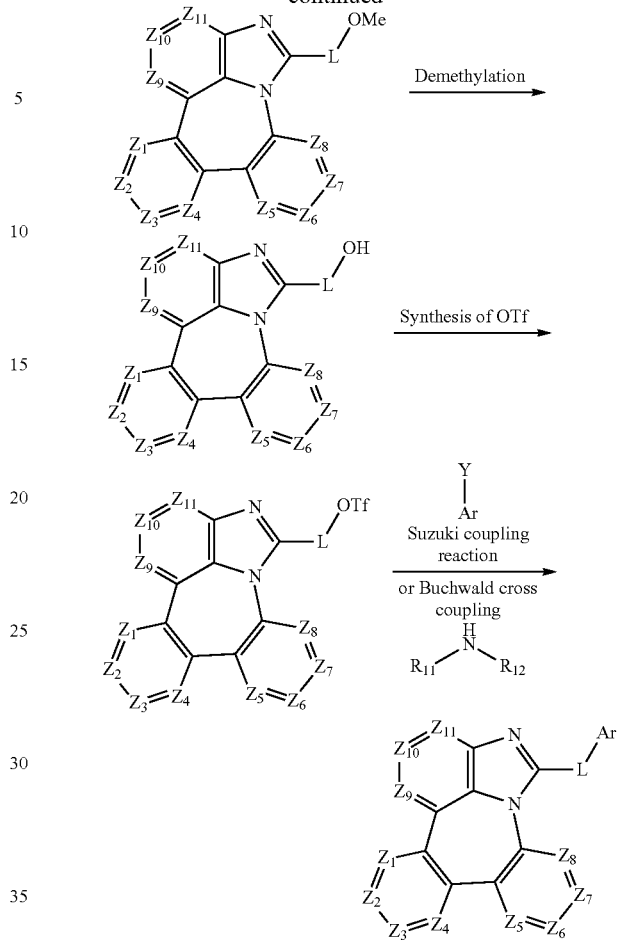

[Reaction Scheme 2]

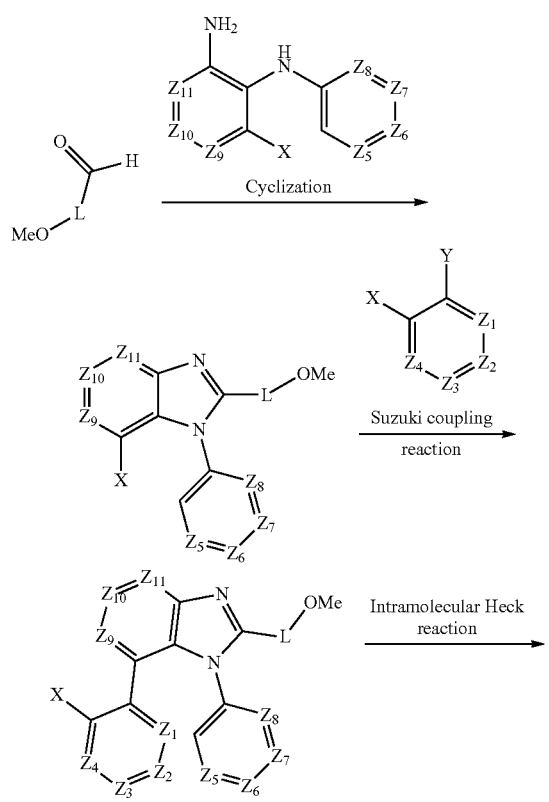

In reaction schemes 1 and 2, $Z_1$ to $Z_{11}$, L, Ar, $R_{11}$, and $R_{12}$ are as defined in formula 1, X represents hydrogen, and Y represents boronic acid or pinacolborate.

The present disclosure may provide the organic electroluminescent material comprising the organic electroluminescent compound of formula 1 and an organic electroluminescent device comprising the organic electroluminescent material.

The organic electroluminescent material may be comprised solely of the organic electroluminescent compound of the present disclosure, and may further comprise conventional materials included in the organic electroluminescent material.

The organic electroluminescent device according to the present disclosure includes a first electrode; a second electrode; and at least one organic material layer interposed between the first electrode and the second electrode.

One of the first electrode and the second electrode may be an anode and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The organic electroluminescent compound represented by formula 1 of the present disclosure may be comprised in at least one layer of the light-emitting layer, the hole injecting layer, the hole transport layer, the hole auxiliary layer, the light-emitting auxiliary layer, the electron transport layer, the electron buffer layer, the electron injection layer, the interlayer, the hole blocking layer, and the electron blocking layer. According to the case, it may be, preferably, comprised in at least one layer of the electron buffer layer and the electron transport layer. When used in the electron buffer layer, the organic electroluminescent compound of formula 1 of the present disclosure may be comprised as an electron buffer material. When used in the electron transport layer, the organic electroluminescent compound of formula 1 of the present disclosure may be comprised as an electron transport material.

The light-emitting layer may include at least one host and at least one dopant. If necessary, the light-emitting layer may comprise a co-host material, i.e., a plurality of two or more host materials.

The host compound to be used in the present disclosure may be a phosphorescent host compound or a fluorescent host compound. While the kinds of host compound to be used are not particularly limited, specifically, the host compound may be a fluorescent host compound, for example, may be an anthracene compound represented by the following formula 11.

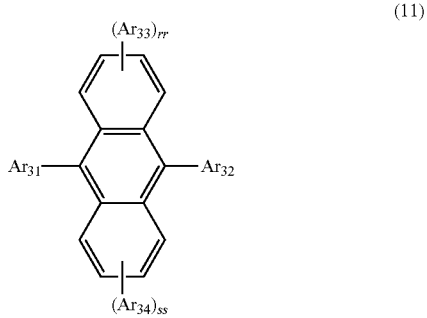

(11)

wherein formula 11, $Ar_{31}$ and $Ar_{32}$ each independently represent a substituted or unsubstituted (C6-C30)aryl, or a substituted or unsubstituted (5- to 30-membered)heteroaryl, preferably a substituted or unsubstituted (C6-C25)aryl, or a substituted or unsubstituted (5- to 25-membered)heteroaryl, more preferably a substituted or unsubstituted (C6-C18)aryl, or a substituted or unsubstituted (5- to 18-membered)heteroaryl; $Ar_{33}$ and $Ar_{34}$ each independently represent hydrogen, deuterium, halogen, cyano, nitro, hydroxy, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30) cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)ar(C1-C30)alkylsilyl, or —NR$_{41}$R$_{42}$; R$_{41}$ and R$_{42}$ each independently represent hydrogen, a substituted or unsubstituted (C6-C30)aryl, or a substituted or unsubstituted (5- to 30-membered)heteroaryl; or may be bonded to each other to form a (3- to 30-membered) mono- or polycyclic, alicyclic or aromatic ring, or a combination of alicyclic and aromatic rings whose carbon atom may be replaced with at least one heteroatom selected from nitrogen, oxygen, and sulfur; preferably halogen, cyano, or a substituted or unsubstituted (C1-C20)alkyl, more preferably halogen, cyano, or a substituted or unsubstituted (C1-C10)alkyl; rr and ss each independently represent an integer of 1 to 4; and where rr or ss is an integer of 2 or more, each of $Ar_{33}$ or $Ar_{34}$ may be the same or different.

According to one embodiment of the present disclosure, $Ar_{31}$ and $Ar_{32}$ each independently represent a substituted or unsubstituted phenyl, a substituted or unsubstituted biphenyl, a substituted or unsubstituted naphthylene, a substituted or unsubstituted fluorene, a substituted or unsubstituted spirofluorene, a substituted or unsubstituted pyrene, a substituted or unsubstituted benzoanthracene, a substituted or unsubstituted phenanthrene, a substituted or unsubstituted carbazole, a substituted or unsubstituted dibenzofuran, a substituted or unsubstituted dibenzothiophene, or a substituted or unsubstituted benzonaphthofuran, etc.

The host material of the present disclosure represented by formula 11 may be specifically illustrated by the following compounds, but is not limited thereto:

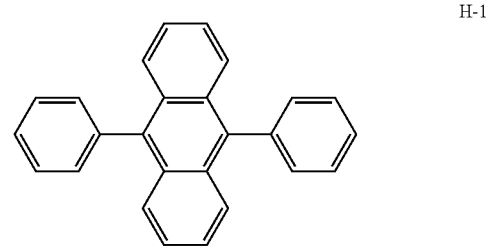

H-1

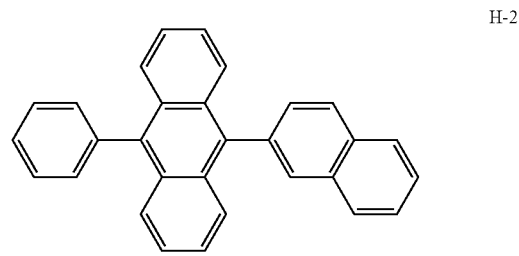

H-2

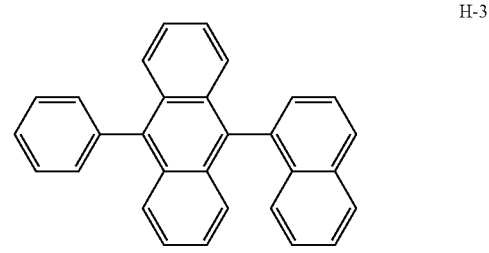

H-3

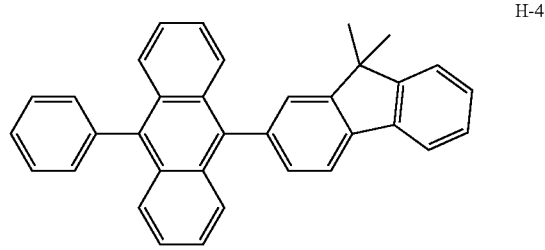

H-4

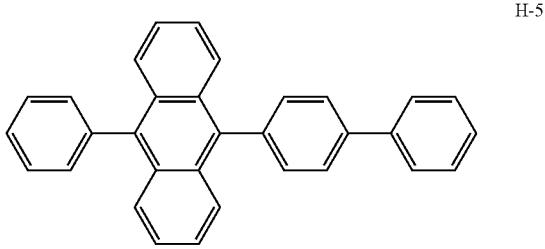

H-5

H-6
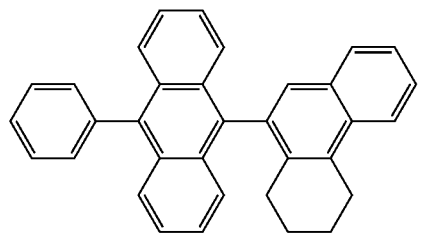
H-7
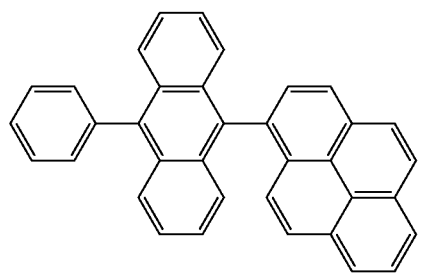
H-8
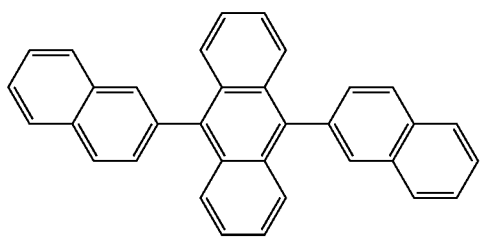
H-9
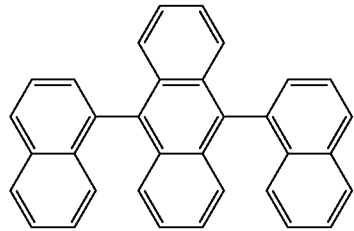
H-10
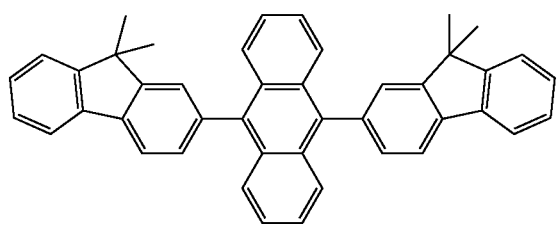
H-11
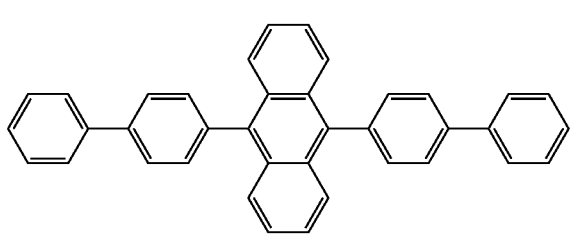
H-12
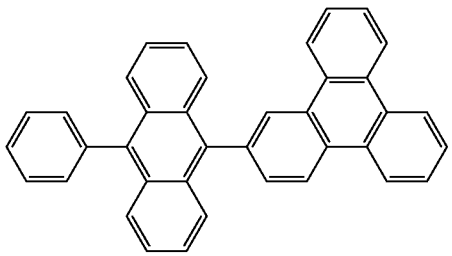
H-13
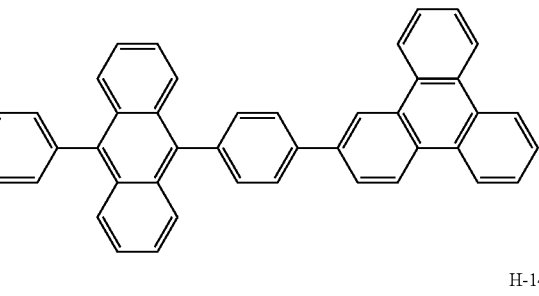
H-14
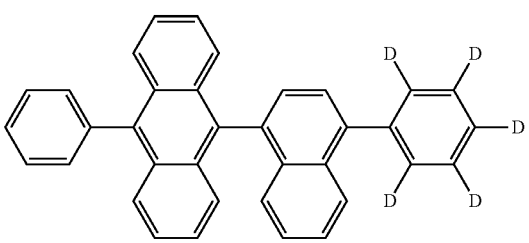
H-15
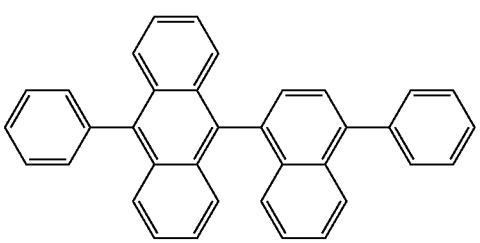
H-16
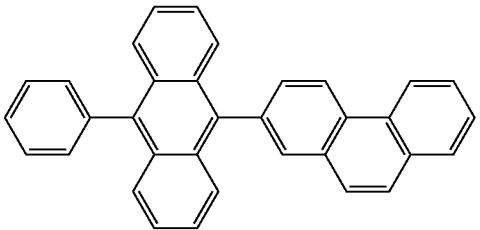
H-17
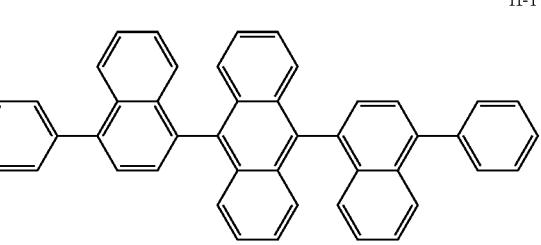

H-18
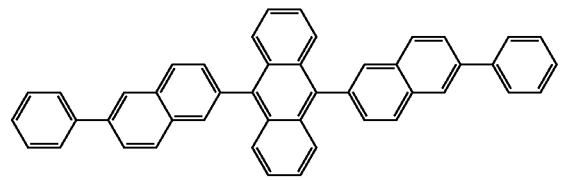
H-19
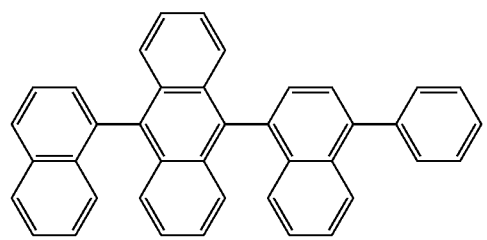
H-20
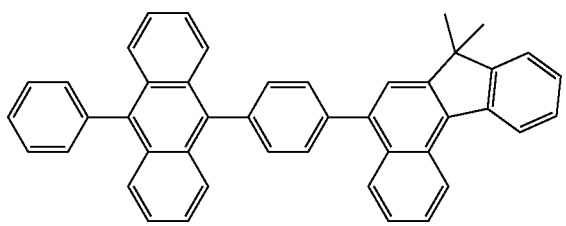
H-21
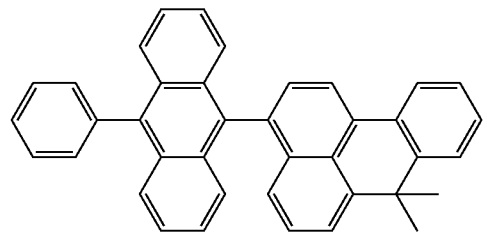
H-22
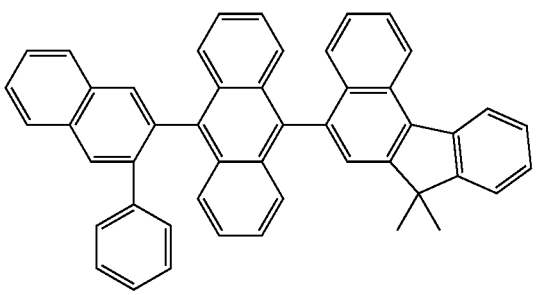
H-23
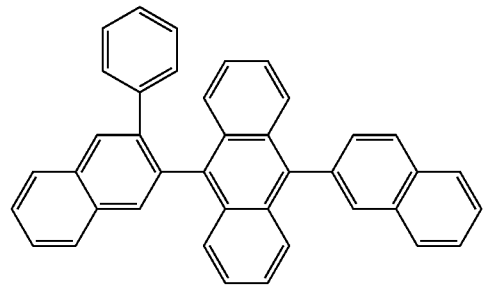
H-24
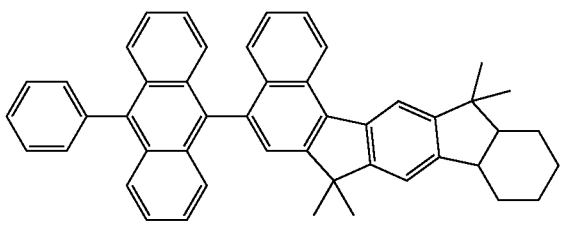
H-25
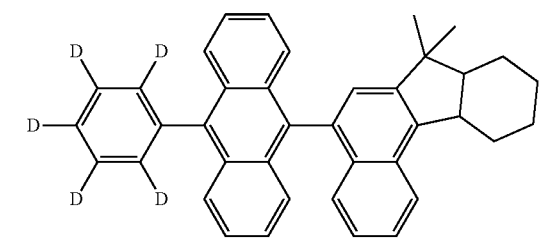
H-26
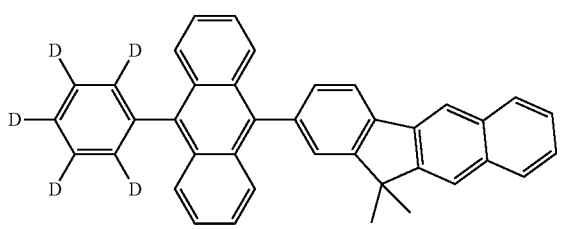
H-27
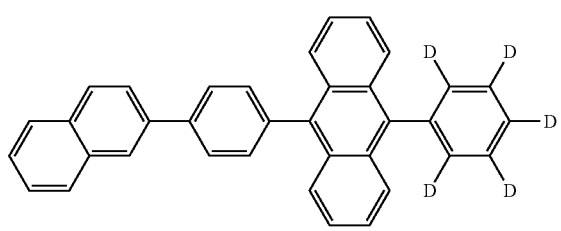
H-28
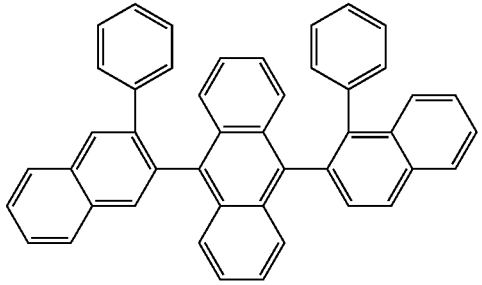
H-29
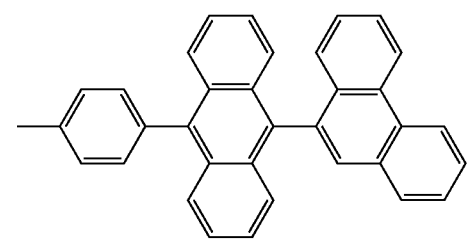

H-30
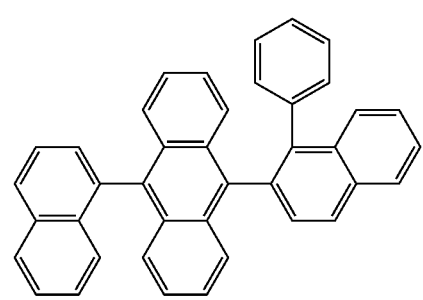
H-31
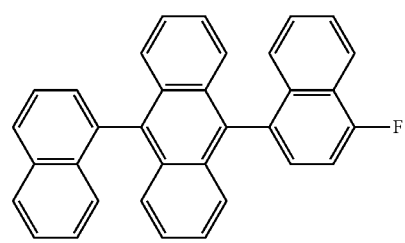
H-32
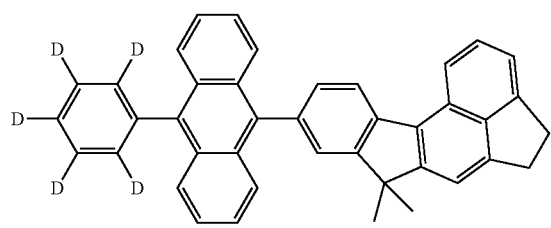
H-33
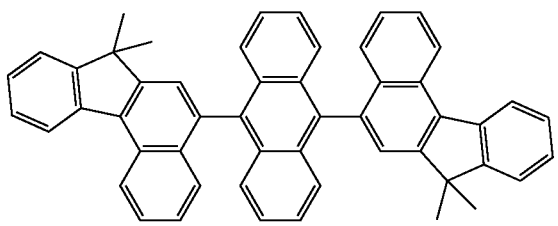
H-34
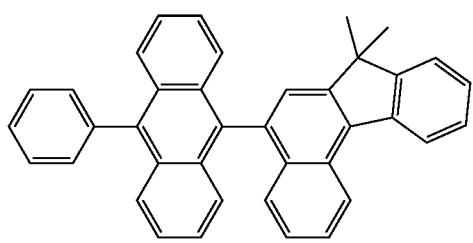
H-35
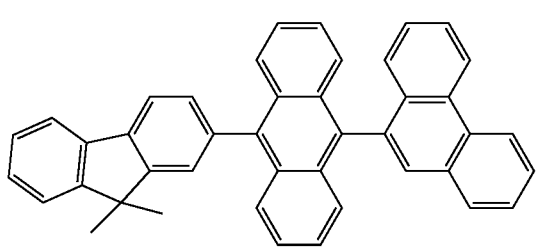
H-36
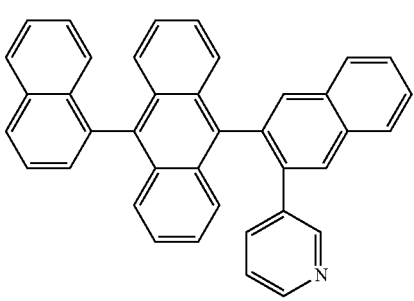
H-37
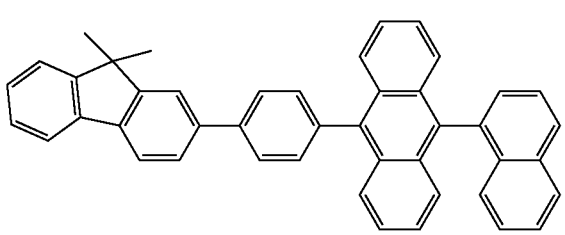
H-38
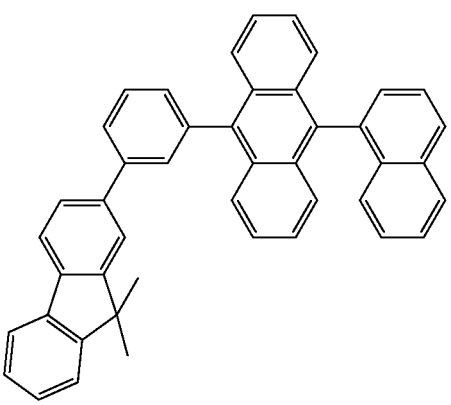
H-39
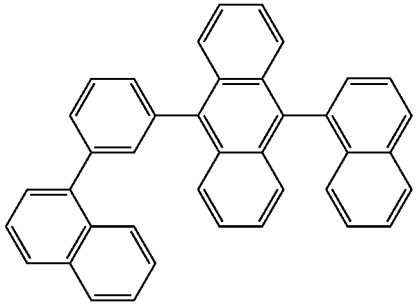
H-40
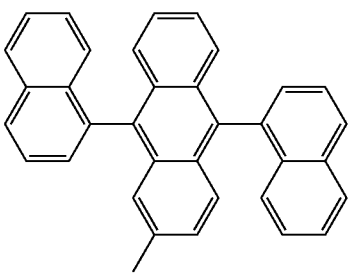

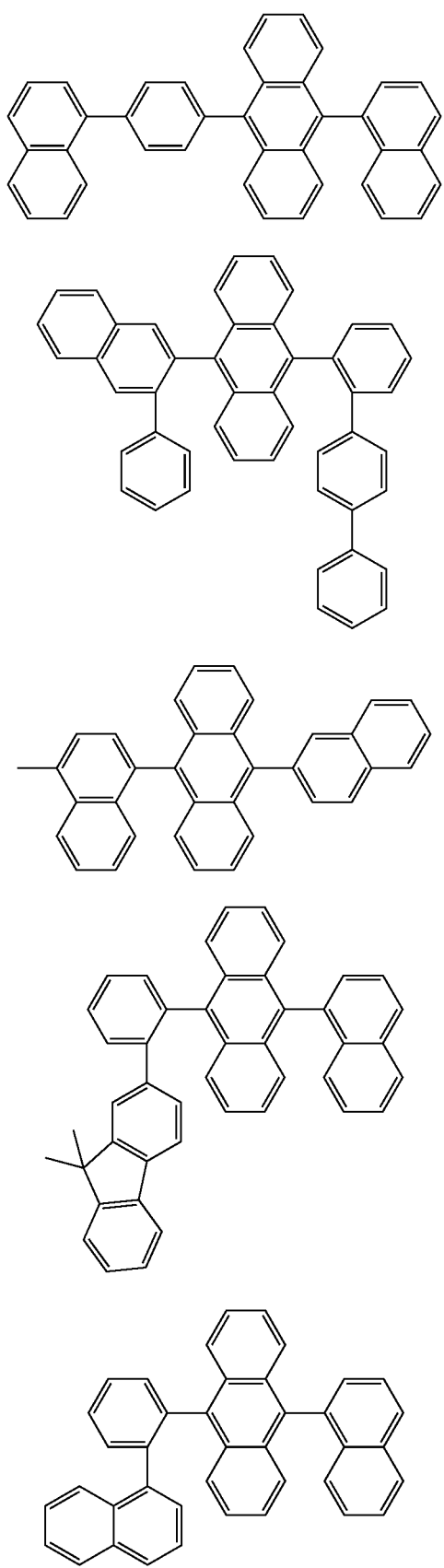
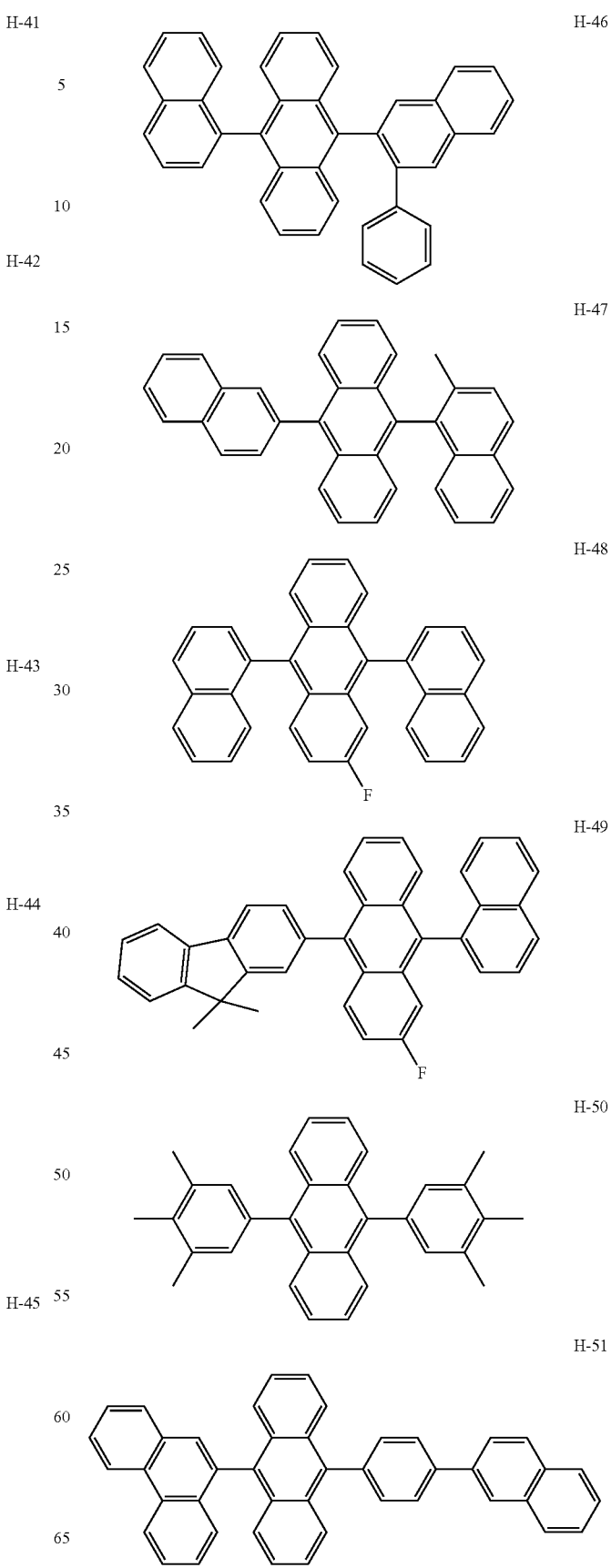

H-52
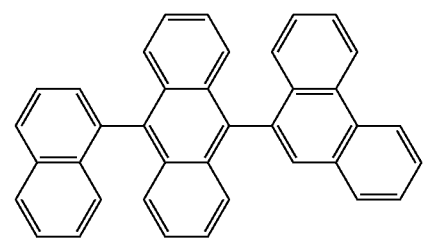
H-53
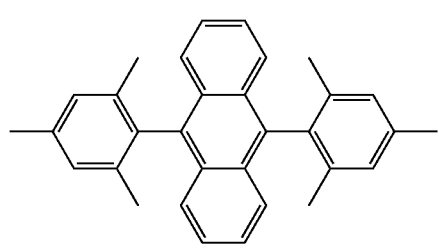
H-54
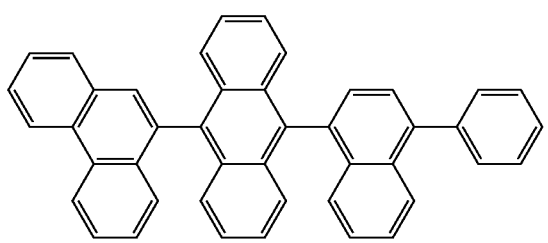
H-55
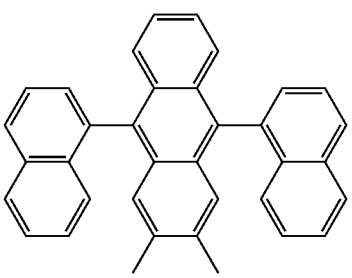
H-56
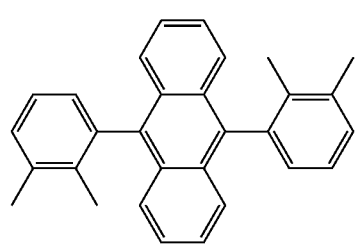
H-57
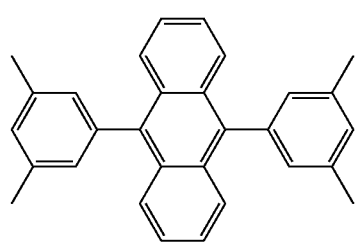
H-58
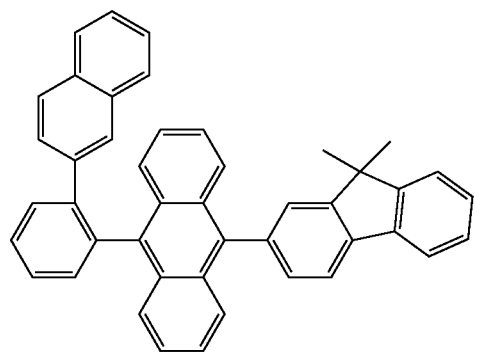
H-59
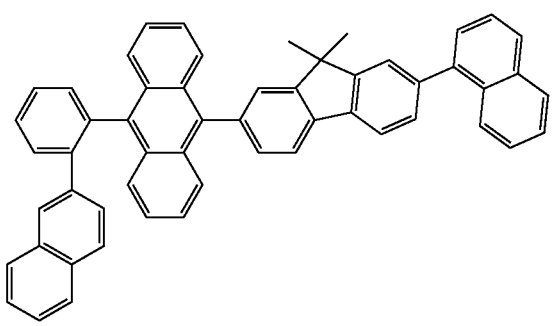
H-60
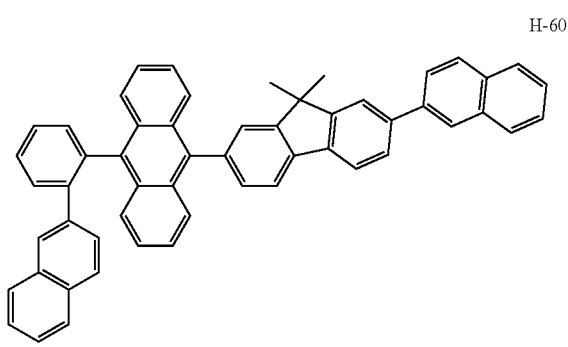
H-61
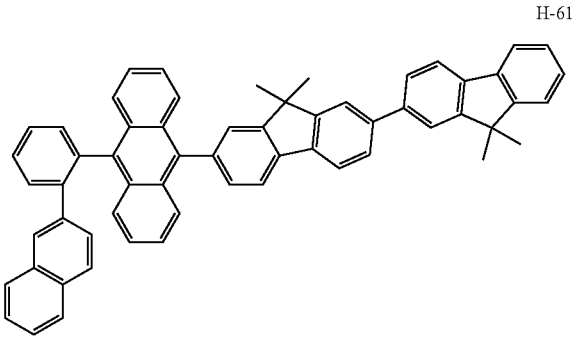

H-62
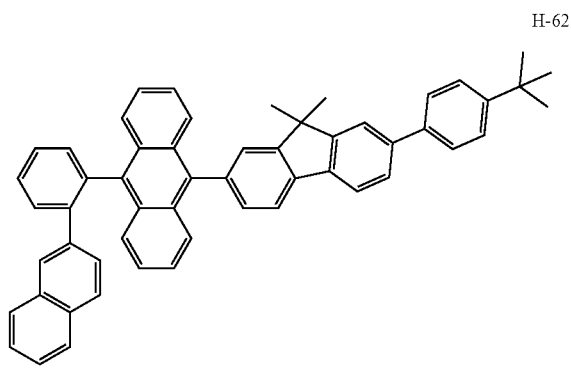
H-67
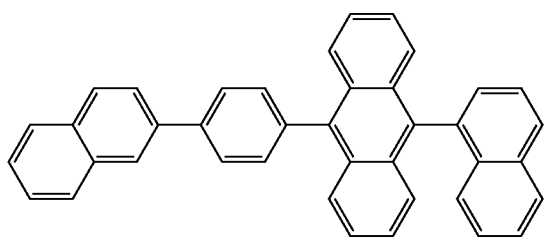
H-63
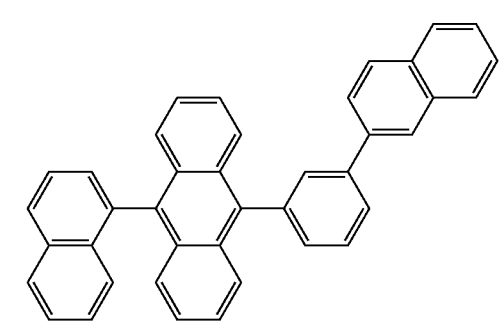
H-68
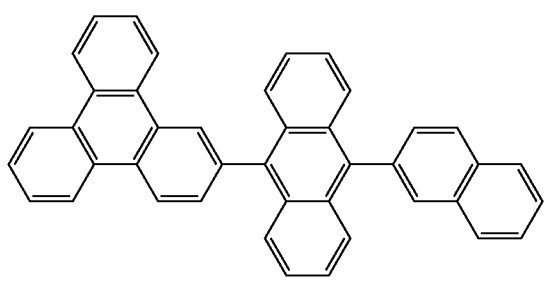
H-64
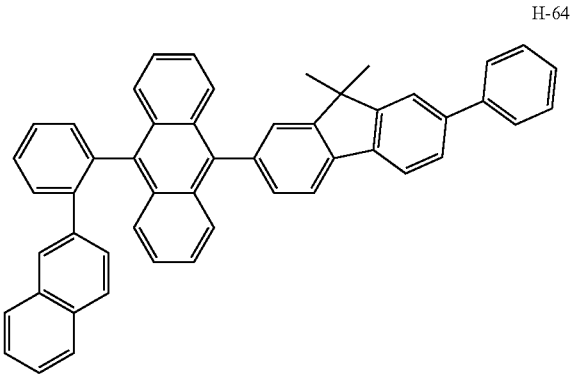
H-69
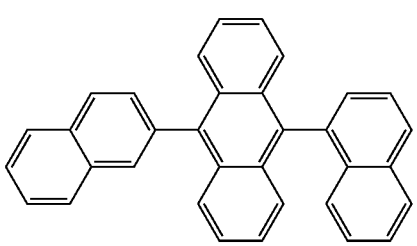
H-65
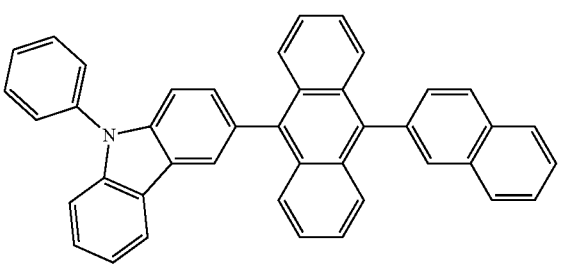
H-70
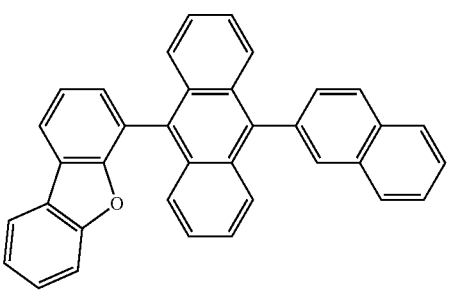
H-66
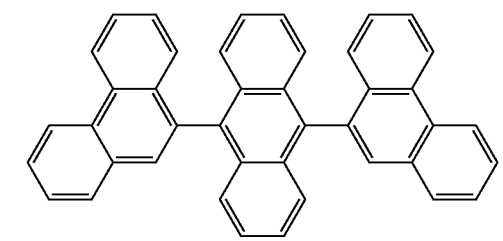
H-71
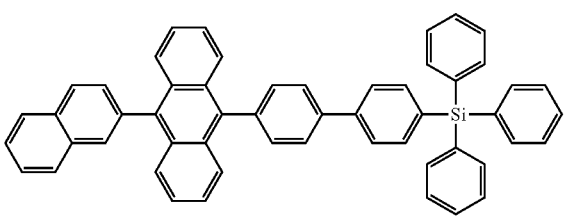

-continued
H-72
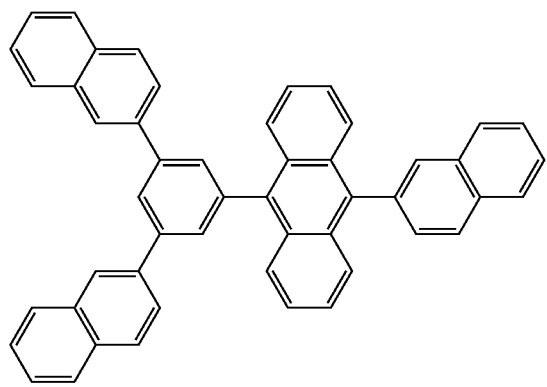
H-73
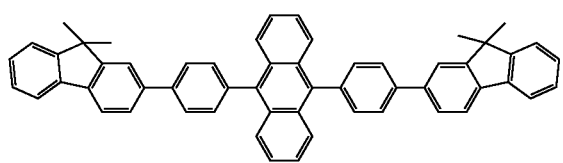
H-74
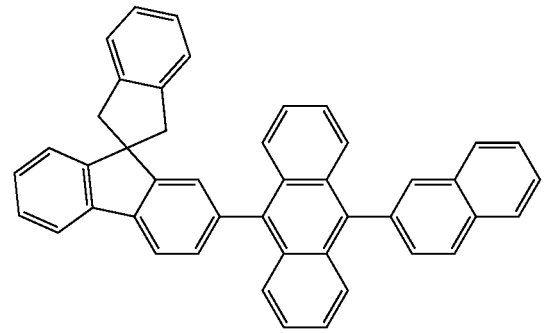
H-75
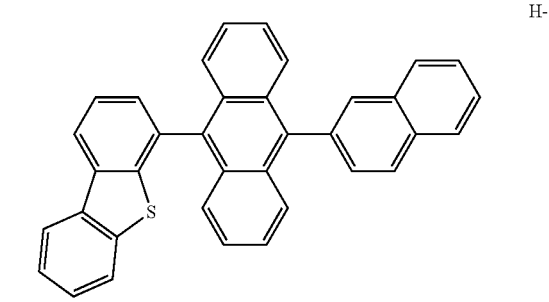
H-76
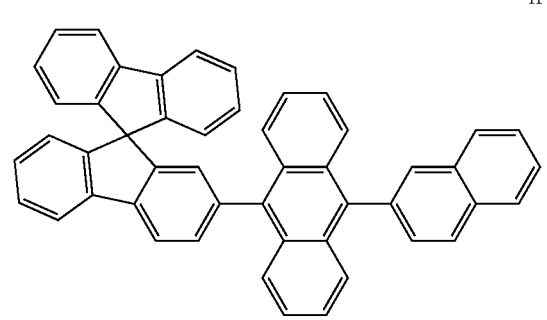
-continued
H-77
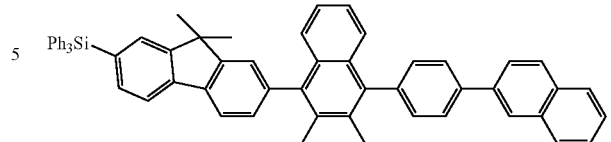
H-78
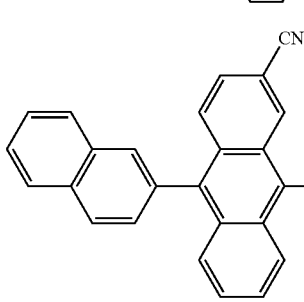
H-79
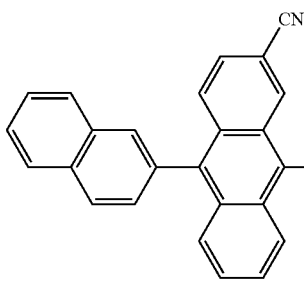
H-80
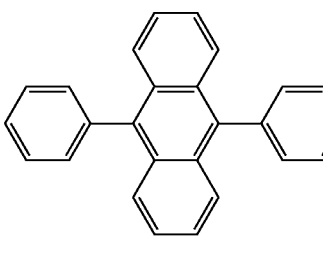
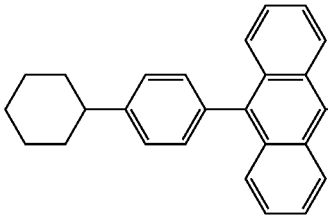
H-81
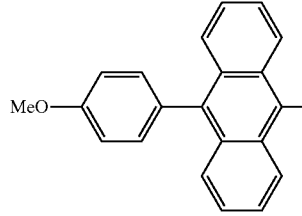
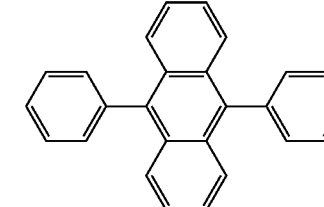
H-82
The dopant compound to be used in the present disclosure may be a phosphorescent dopant compound or a fluorescent dopant compound. Specifically, the dopant compound may be a fluorescent dopant compound, for example, may be a condensed polycyclic amine derivative represented by the following formula 21.

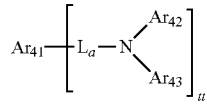
(21)

wherein formula 21, wherein Ar$_{41}$ represents a substituted or unsubstituted (C6-C50)aryl or styryl; L$_a$ represents a single bond, a substituted or unsubstituted (C6-C30)arylene, or a substituted or unsubstituted (3- to 30-membered)heteroarylene; Ar$_{42}$ and Ar$_{43}$ each independently represent hydrogen, deuterium, a halogen, a substituted or unsubstituted (C1-C30) alkyl, a substituted or unsubstituted (C6-C30)aryl, or a substituted or unsubstituted (3- to 30-membered)heteroaryl; or may be linked to an adjacent substituent(s) to form a (3- to 30-membered) mono- or polycyclic, alicyclic or aromatic ring, or a combination of alicyclic and aromatic rings whose carbon atom may be replaced with at least one heteroatom selected from nitrogen, oxygen, and sulfur; tt represents 1 or 2; and where tt is 2, each of

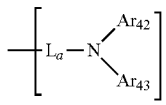

may be the same or different.

A preferable aryl group for Ar$_{41}$ includes a substituted or unsubstituted phenyl, a substituted or unsubstituted fluorenyl, a substituted or unsubstituted anthryl, a substituted or unsubstituted pyrenyl, a substituted or unsubstituted chrysenyl, a substituted or unsubstituted benzofluorenyl, and spiro[fluoren-benzofluorene], etc.

The compound of formula 21 may be illustrated by the following compounds, but is not limited thereto:

D-1
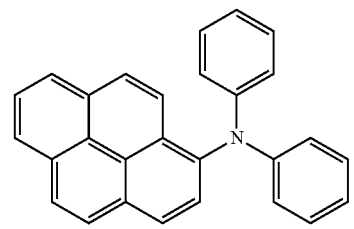

D-2
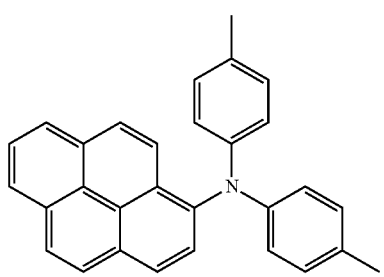

-continued

D-3
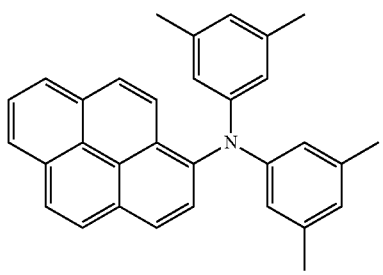

D-4
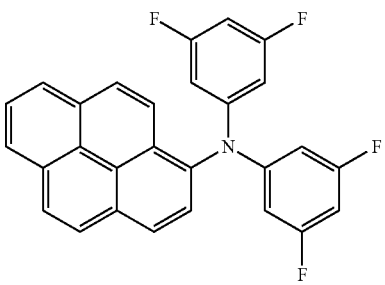

D-5
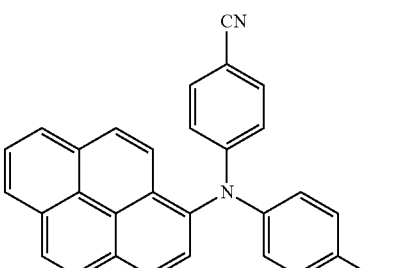

D-6
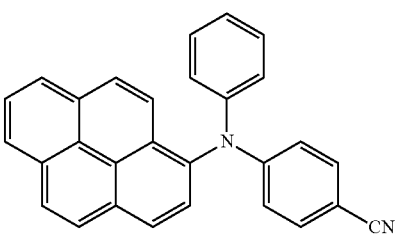

D-7

D-8
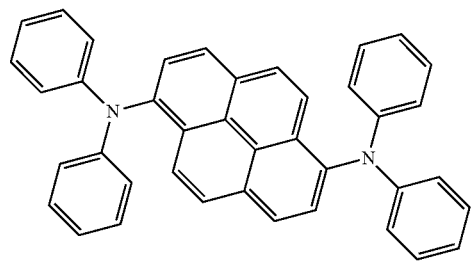
D-9
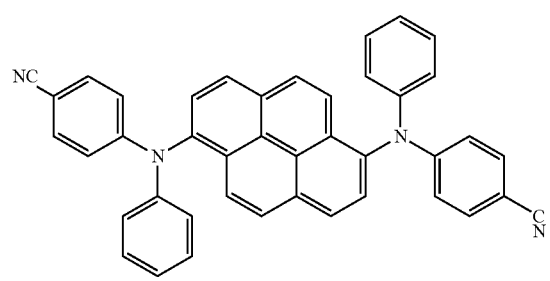
D-10
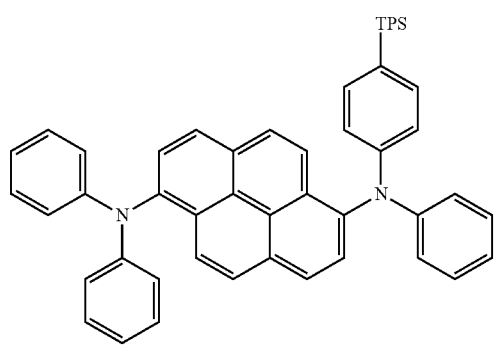
D-11
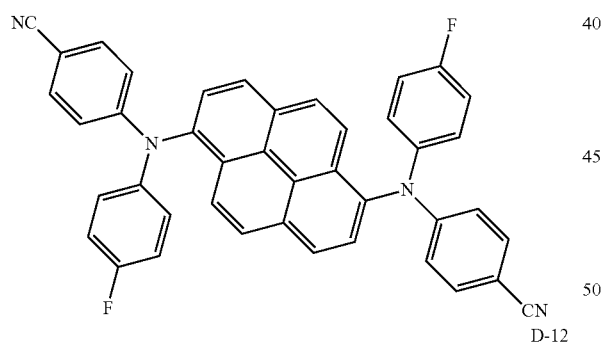
D-12
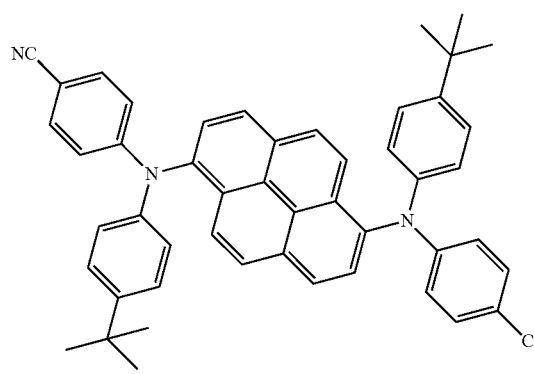
D-13
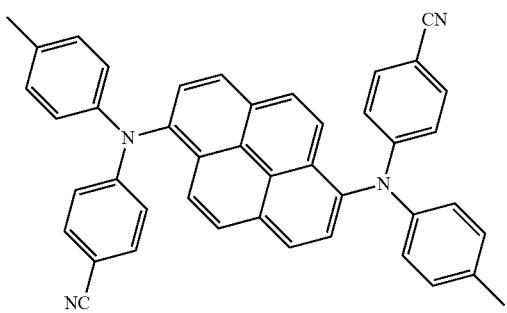
D-14
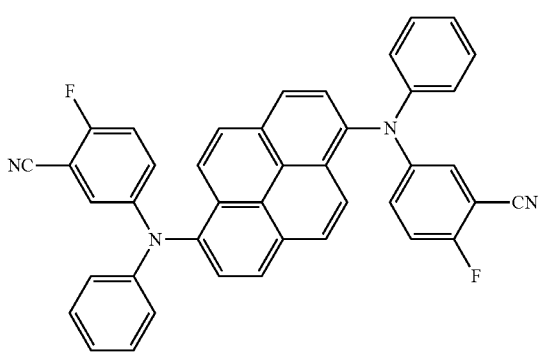
D-15
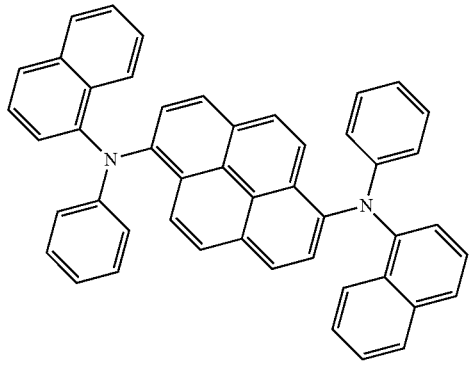
D-16
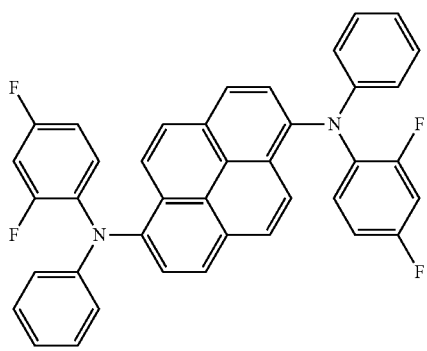

-continued
D-17
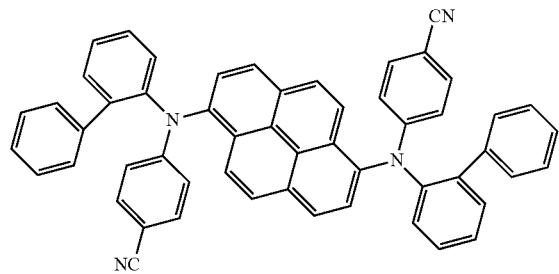
D-18
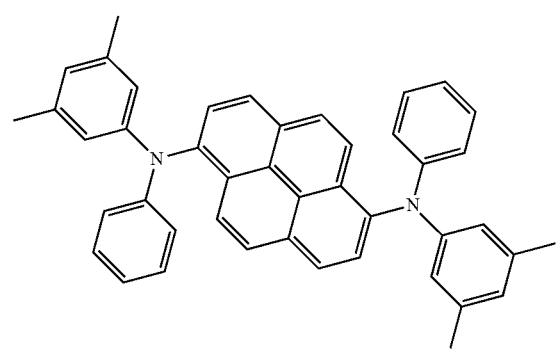
D-19
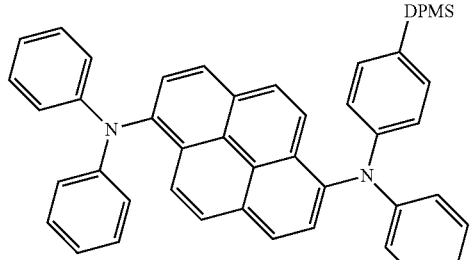
D-20
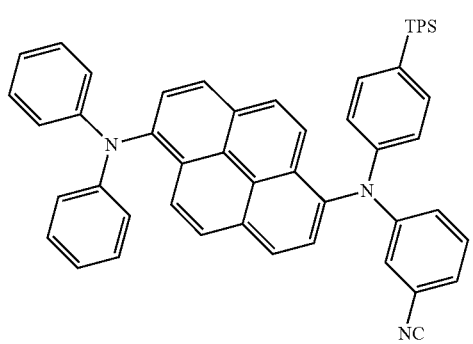
D-21
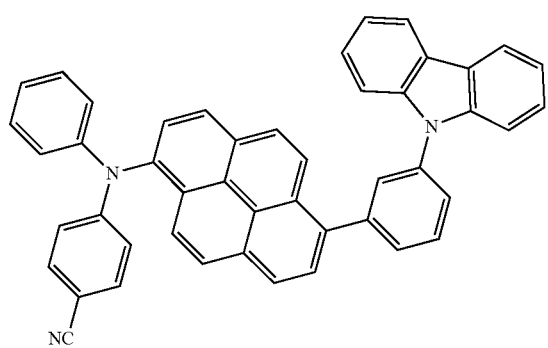
-continued
D-22
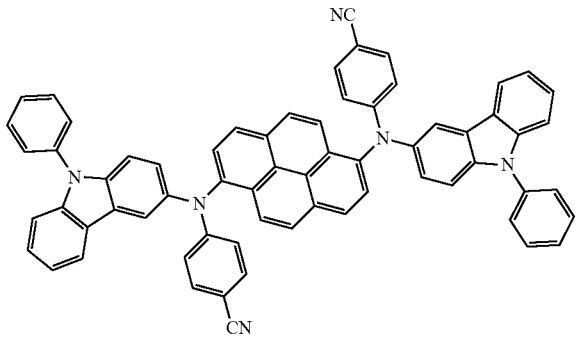
D-23
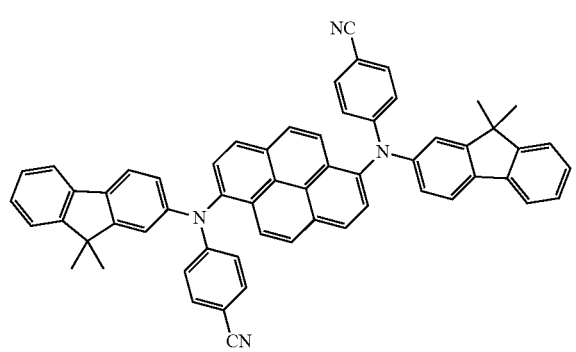
D-24
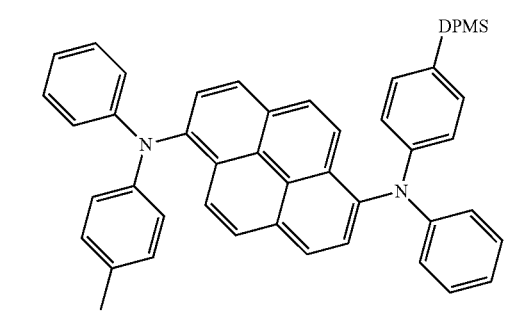
D-25
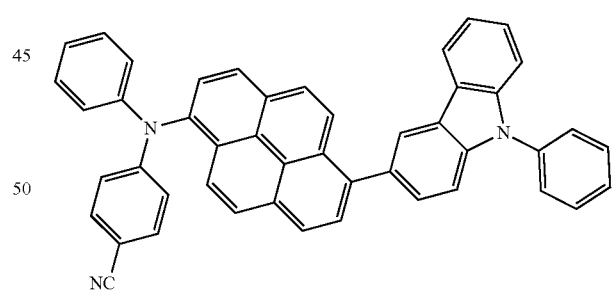
D-26
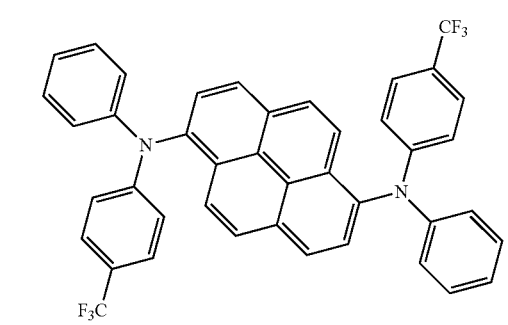

-continued
D-27
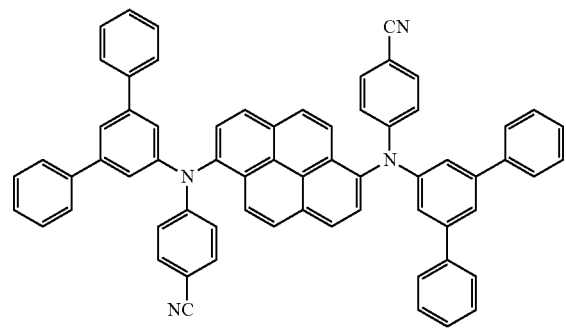
D-31
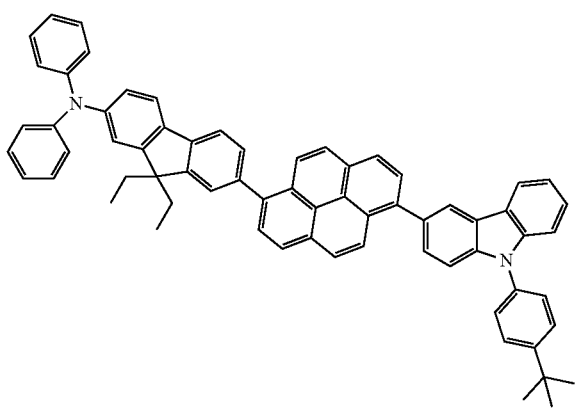
D-28
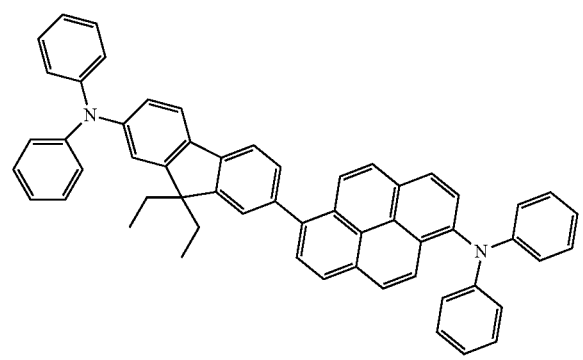
D-32
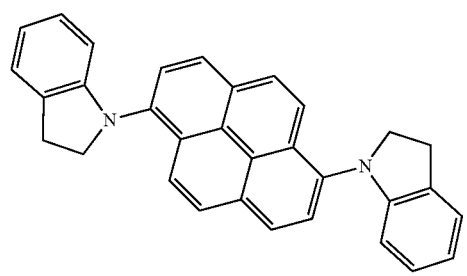
D-29
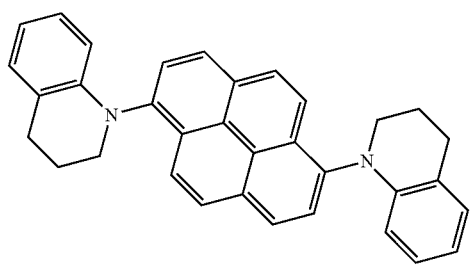
D-33
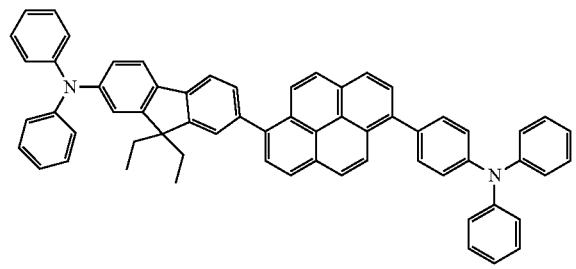
D-30
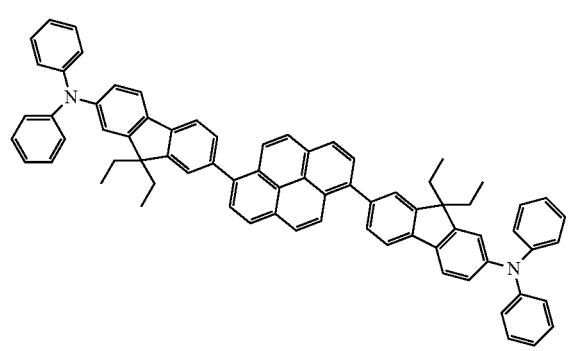
D-34
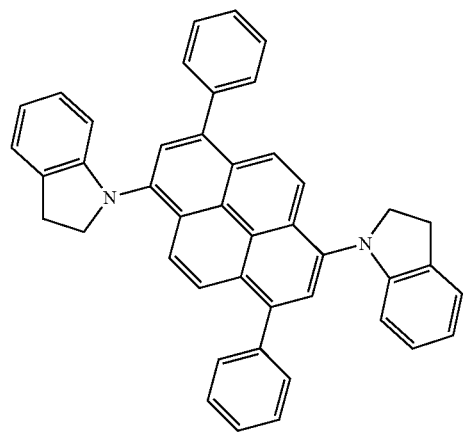

-continued
D-35
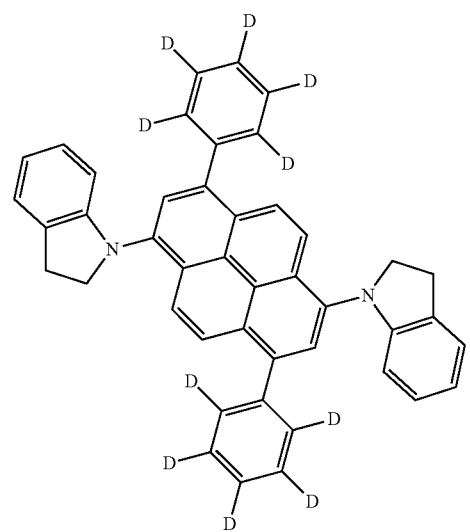
D-36
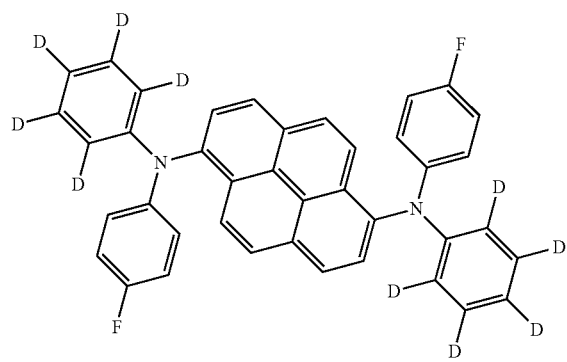
D-37
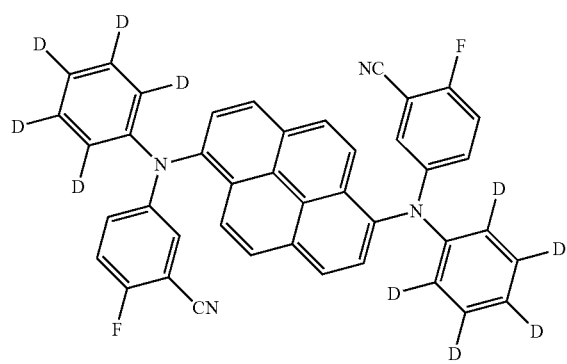
D-38
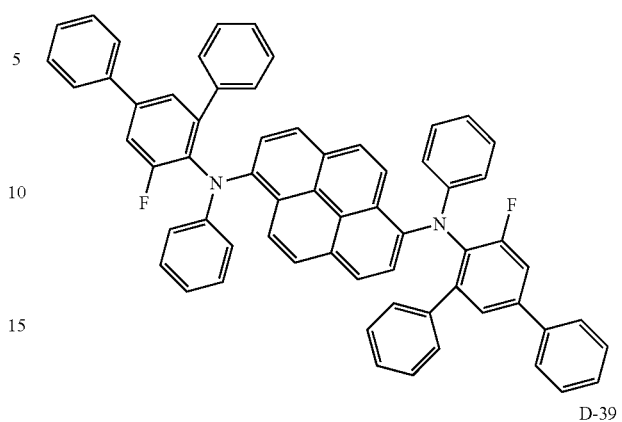
D-39
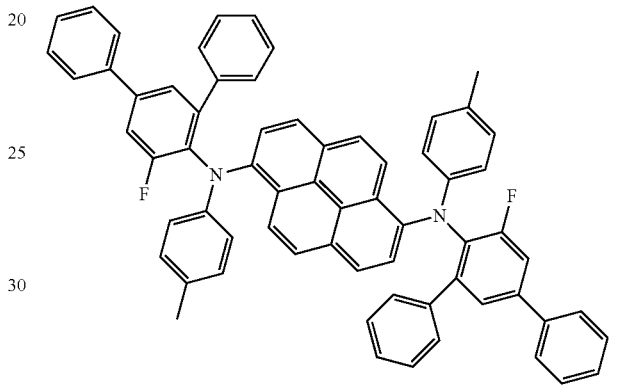
D-40
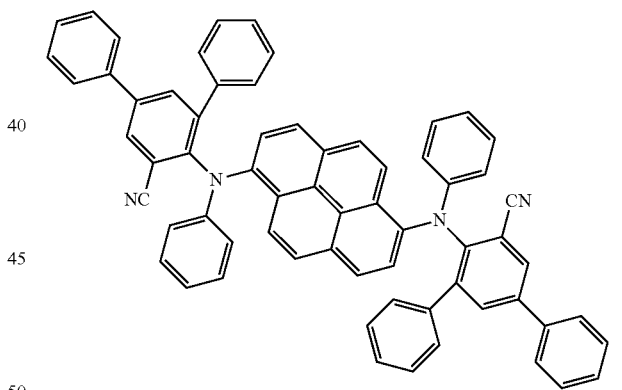
D-41
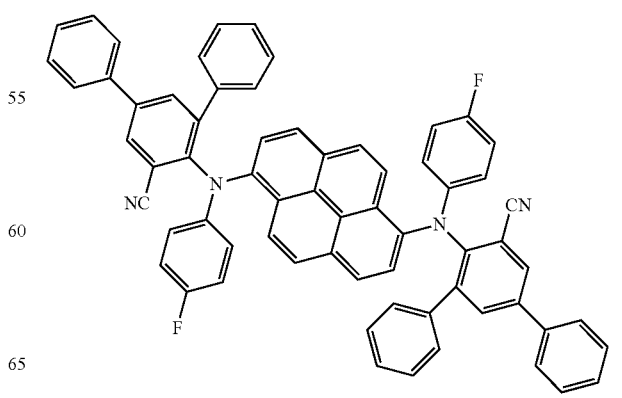

-continued
D-42
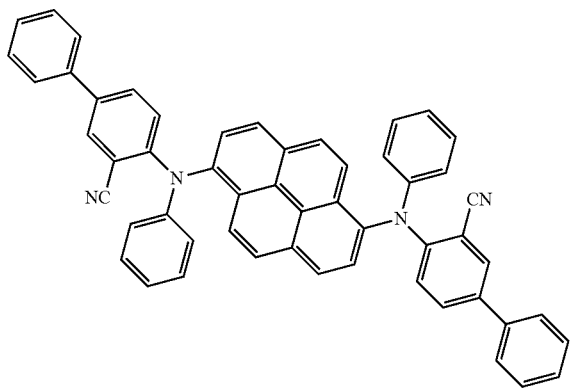
D-43
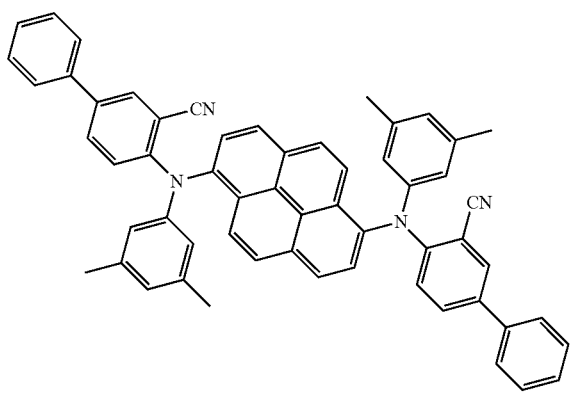
D-44
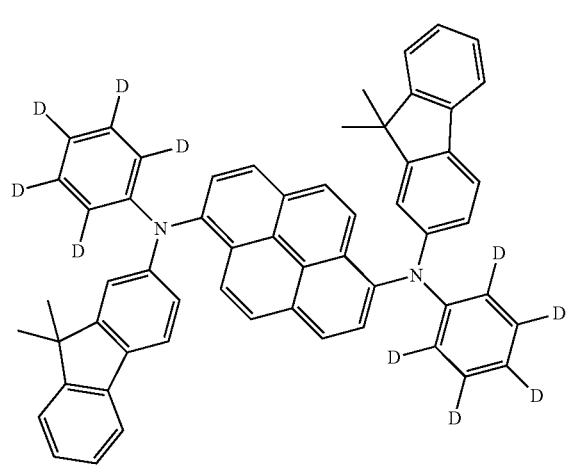
-continued
D-45
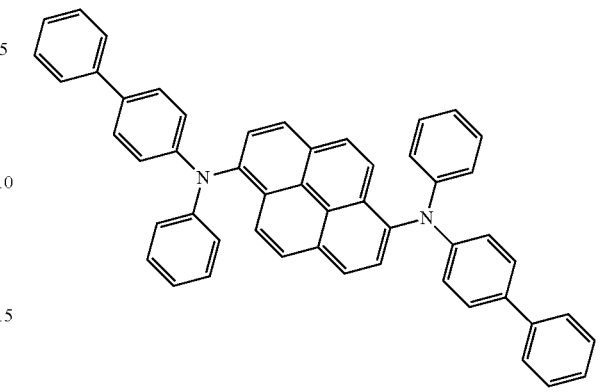
D-46
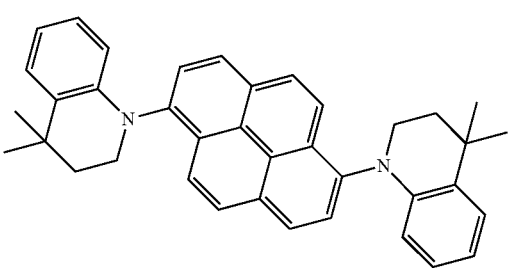
D-47
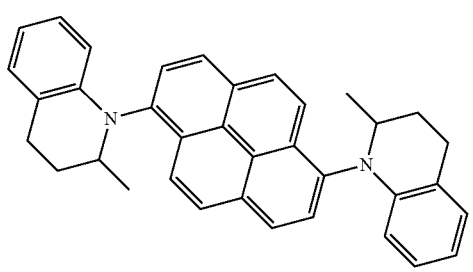
D-48
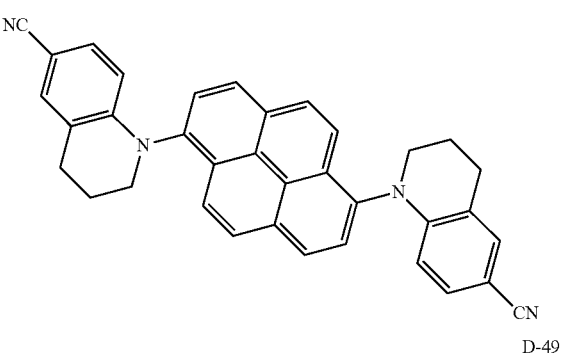
D-49

-continued
D-50
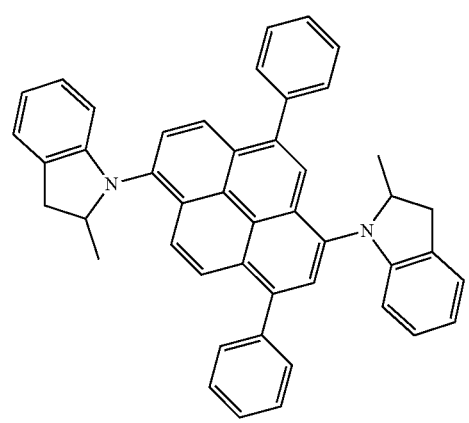
D-51
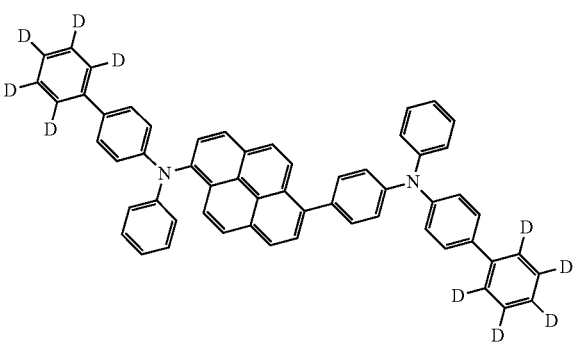
D-52
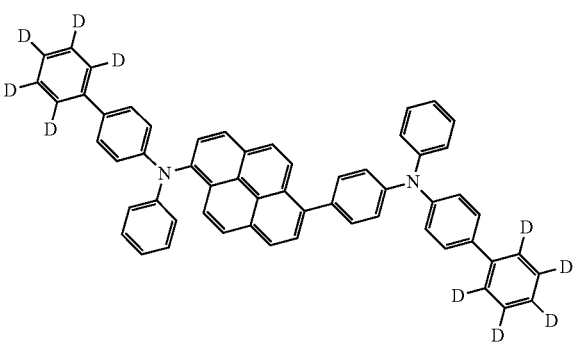
D-53
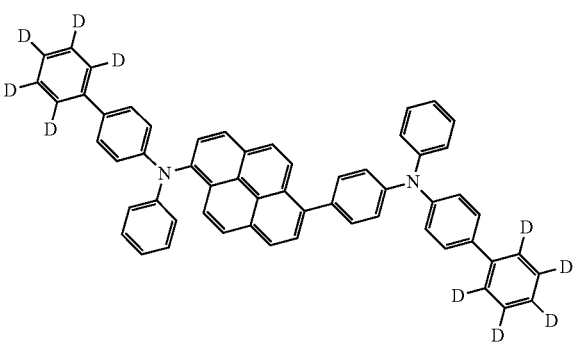
-continued
D-54
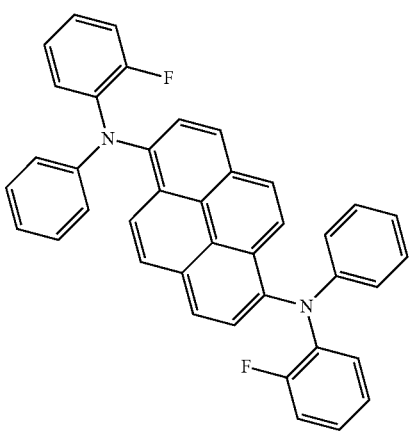
D-55
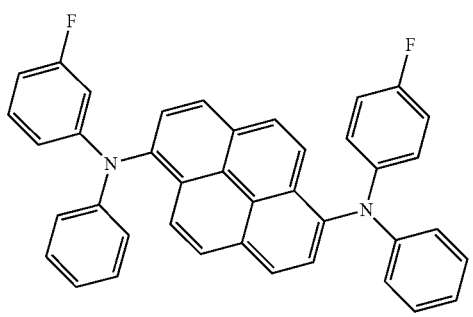
D-56
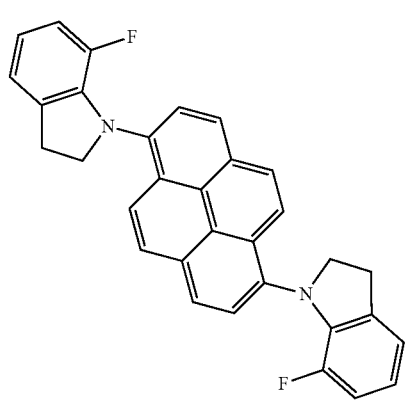
D-57
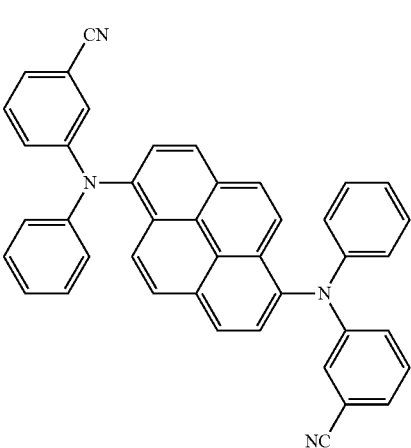

-continued
D-58
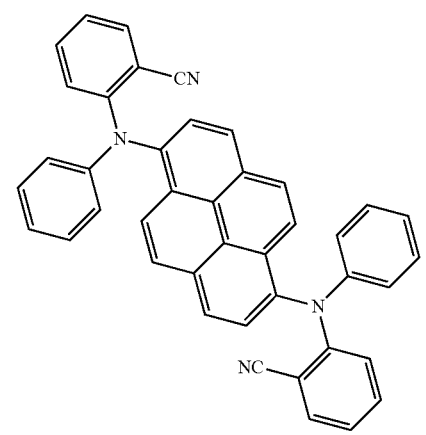
D-59
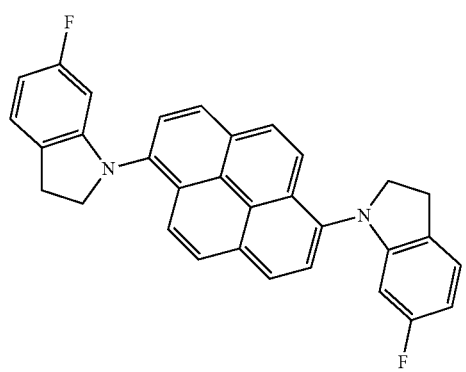
D-60
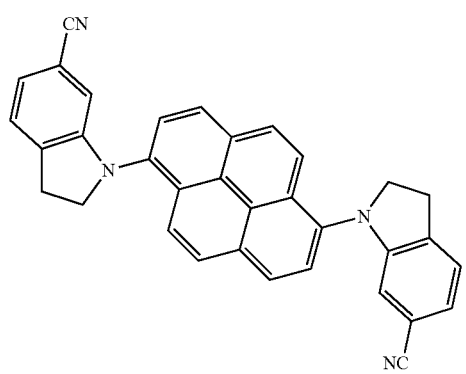
D-61
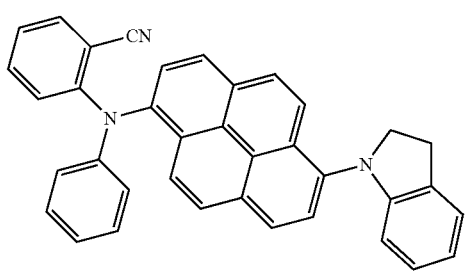
-continued
D-62
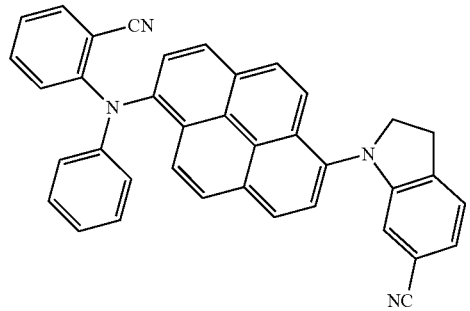
D-63
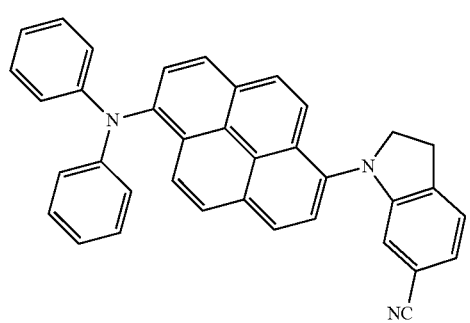
D-64
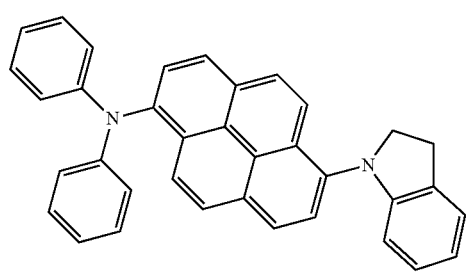
D-65
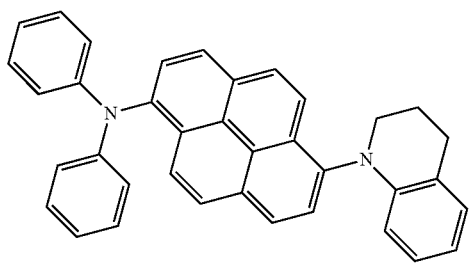
D-66
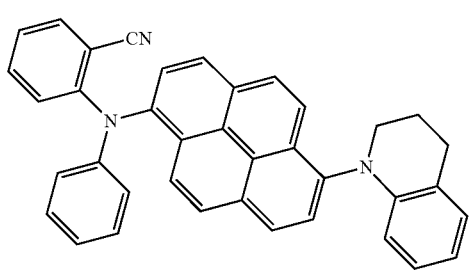

-continued
D-67
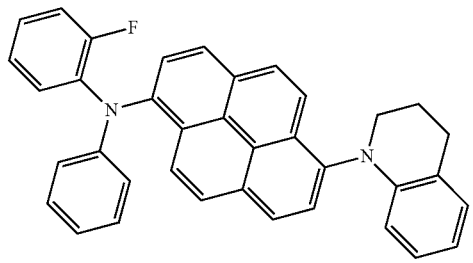
D-68
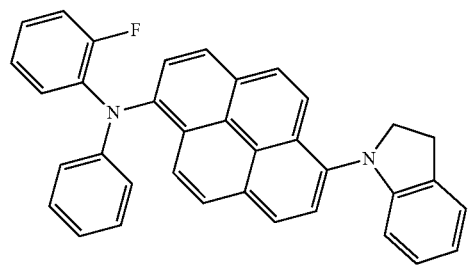
D-69
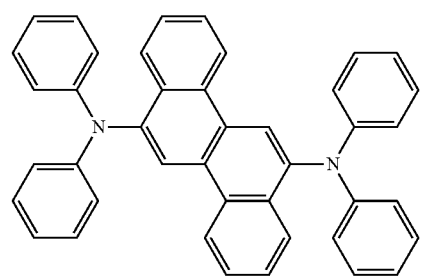
D-70
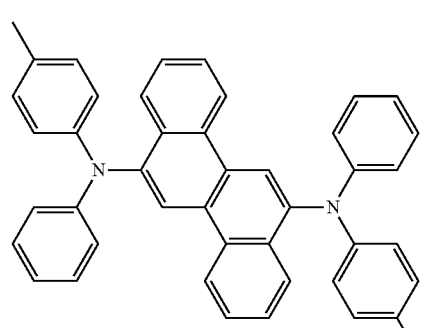
D-71
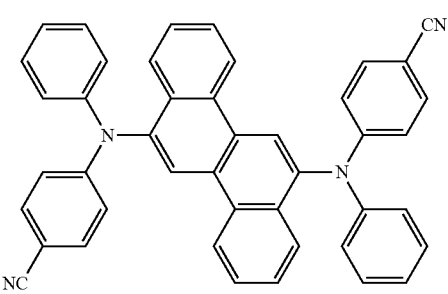
-continued
D-72
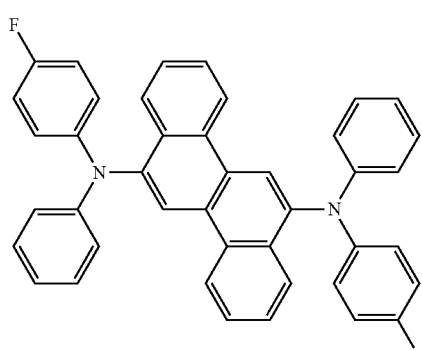
D-73
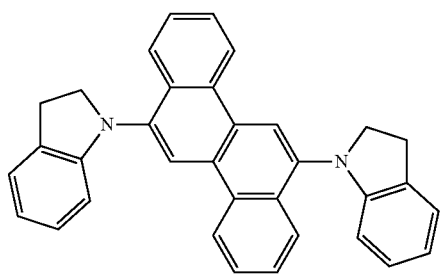
D-74
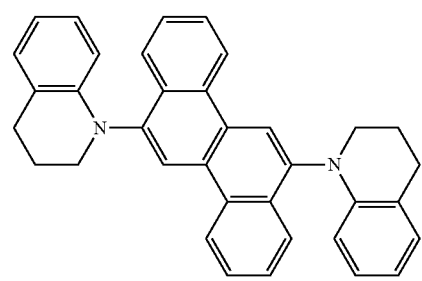
D-75
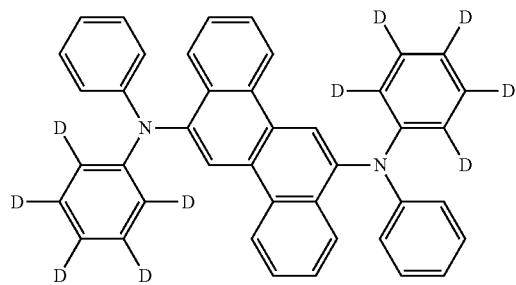

D-76
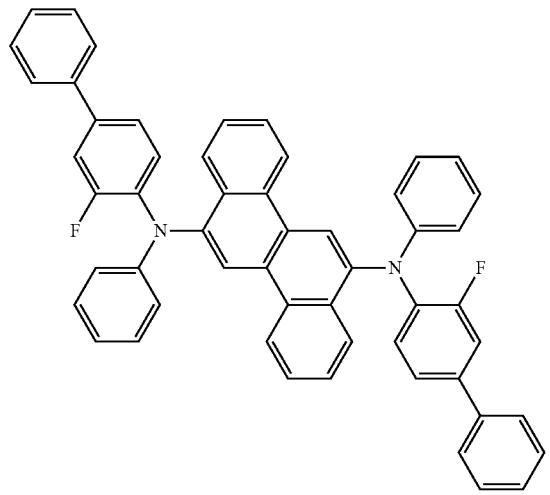
D-77
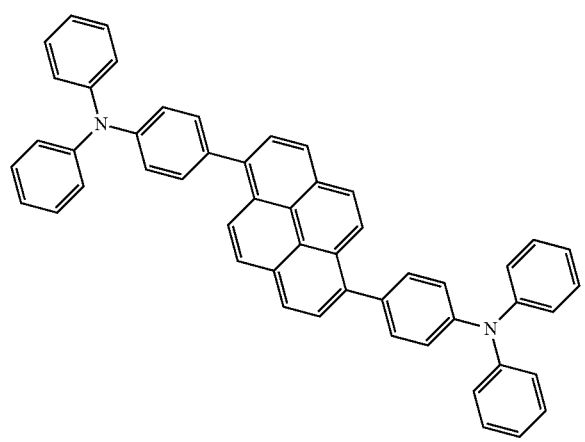
D-78
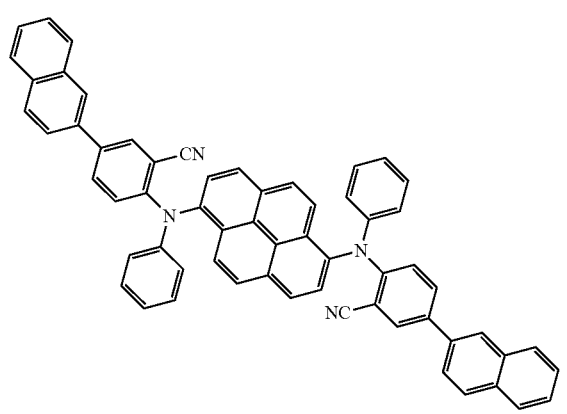
D-79
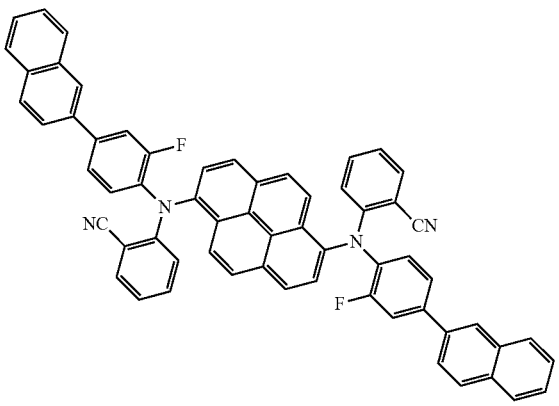
D-80
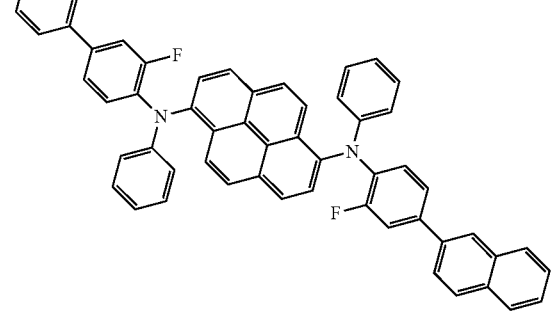
D-81
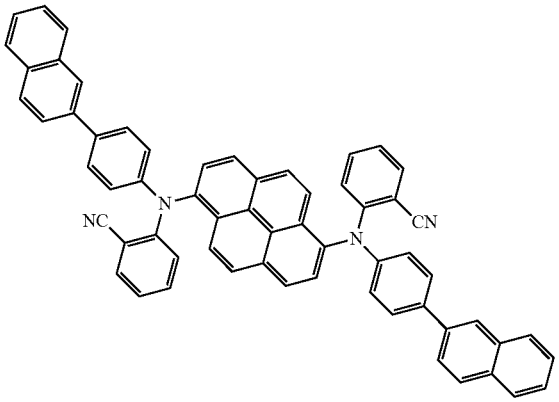
D-82

D-83
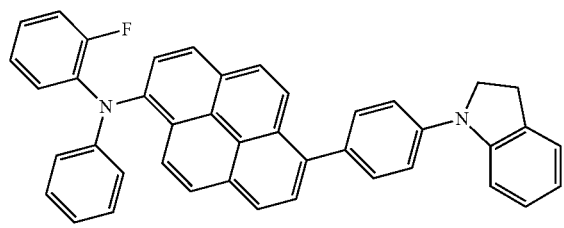
D-86
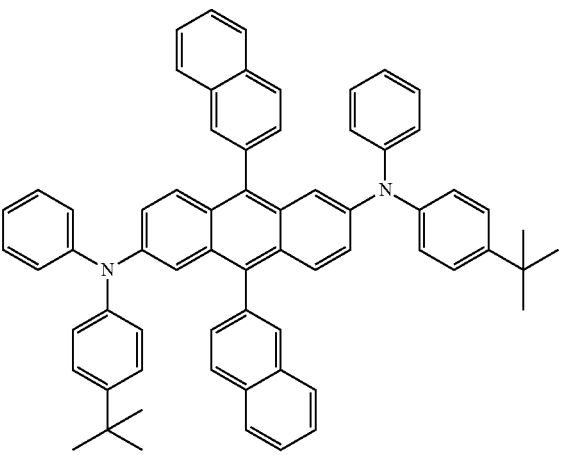
D-84
D-85
D-87
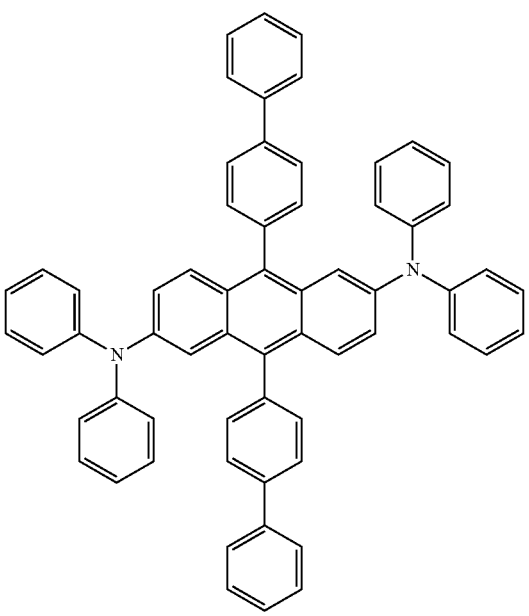

D-88
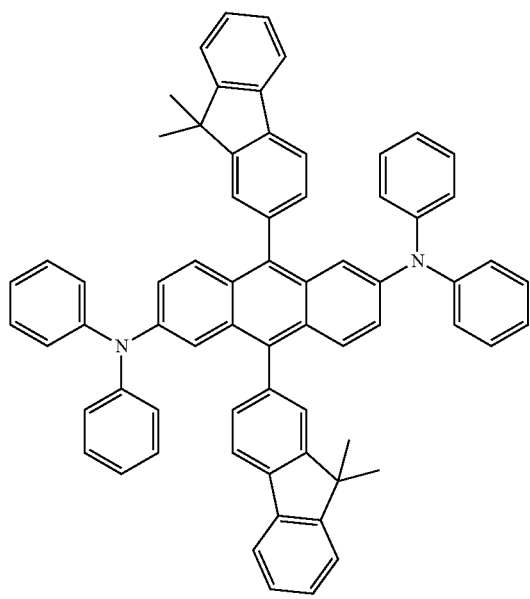
D-89
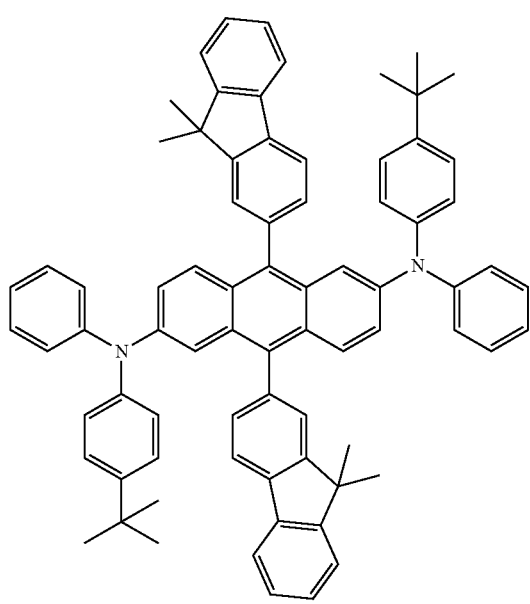
D-90
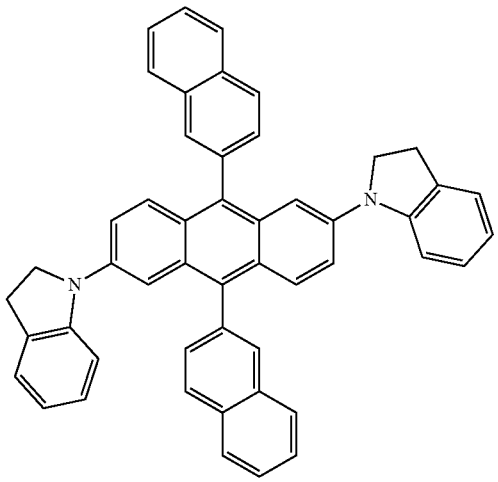
D-91
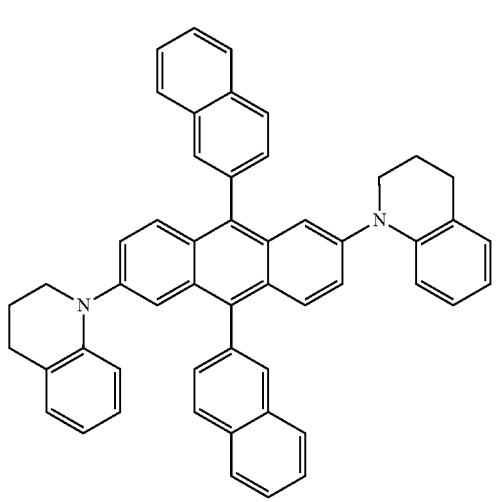
D-92
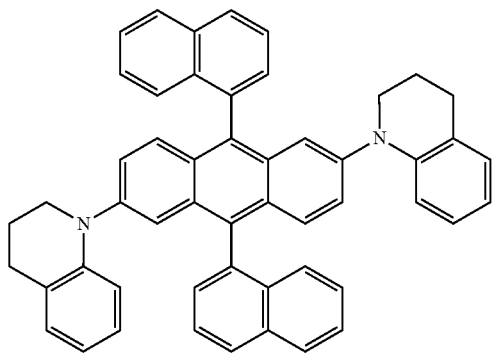

D-93

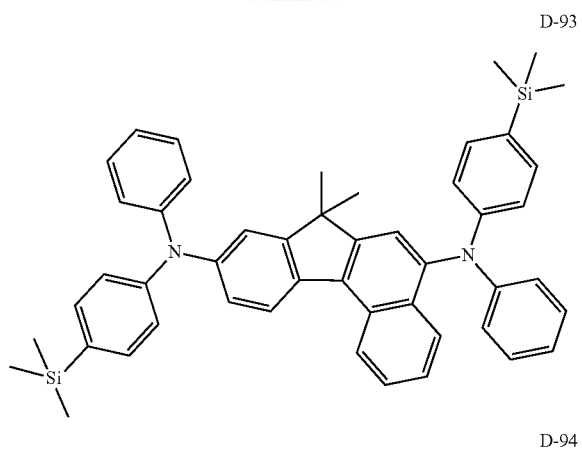

D-94

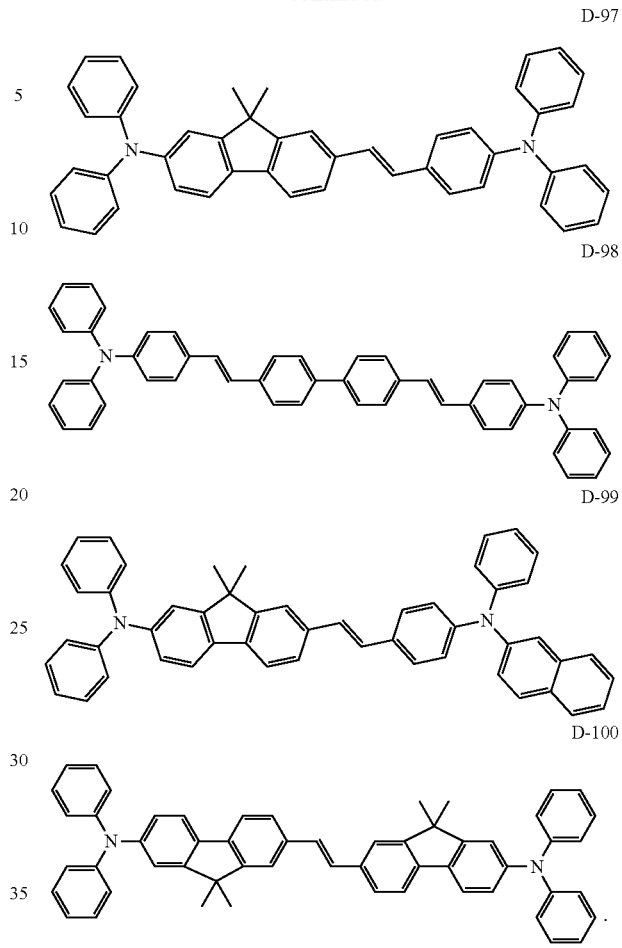

D-97

D-98

D-99

D-100

D-95

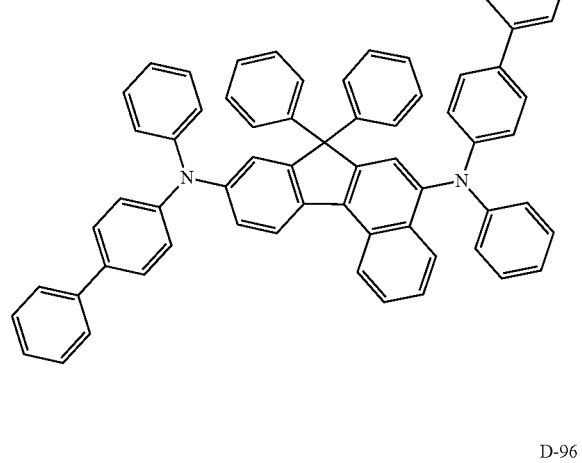

D-96

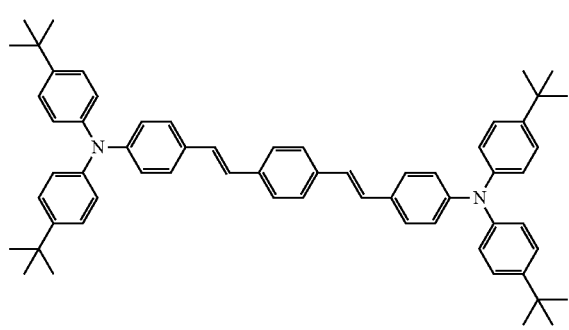

The organic electroluminescent device of the present disclosure may further comprise at least one compound selected from the group consisting of an arylamine-based compound and a styrylarylamine-based compound in the organic layer.

Also, in the organic electroluminescent device of the present disclosure, the organic layer may further comprise at least one metal selected from the group consisting of metals of Group 1, metals of Group 2, transition metals of the 4th period, transition metals of the 5th period, lanthanides, and organic metals of the d-transition elements of the Periodic Table, or at least one complex compound comprising such a metal.

Also, the organic electroluminescent device of the present disclosure further comprises at least one light-emitting layer comprising a blue, red or green light-emitting compound known in the art in addition to the compound of the present disclosure, so that it may emit white light. Further, if necessary, it may further include a yellow or orange light-emitting layer.

In the organic electroluminescent device of the present disclosure, preferably, at least one layer (hereinafter, "a surface layer") selected from a chalcogenide layer, a metal halide layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a metal halide layer or a metal oxide layer is preferably placed on a cathode surface of an electroluminescent medium layer. The operation stability for the organic electroluminescent device may be obtained by the surface layer. Preferably, the chalcogenide includes $SiO_X(1 \leq X \leq 2)$, $AlO_X(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer and the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each layer may use a plurality of compounds. The hole blocking layer or the electron transport layer may also be multi-layers, wherein each layer may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. Also, the hole auxiliary layer may be placed between the hole transport layer (or hole injection layer) and the light-emitting layer, and may be effective to promote or block the hole transport rate (or the hole injection rate), thereby enabling the charge balance to be controlled. Also, the electron blocking layer may be placed between the hole transport layer (or the hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

Forming each layer of the organic electroluminescent device of the present disclosure can apply one method of dry film-forming methods such as vacuum evaporation, sputtering, plasma, ion plating methods, etc., or wet film-forming methods such as ink jet printing, nozzle printing, slot coating, spin coating, dip coating, flow coating methods, etc. The first and the second host compounds of the present disclosure may be film-formed by a co-evaporation process or a mixture-evaporation process.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Also, the organic electroluminescent device of the present disclosure can be used for the manufacture of display devices such as smartphones, tablets, notebooks, PCs, TVs, or display devices for vehicles, or lighting devices such as an outdoor or indoor lighting.

Hereinafter, the preparation method of an organic electroluminescent compound according to the present disclosure, and the properties thereof will be explained in detail with reference to the representative compounds of the present disclosure in order to understand the present disclosure in detail. However, the present disclosure is not limited by the following examples.

EXAMPLE 1: PREPARATION OF COMPOUND C-32
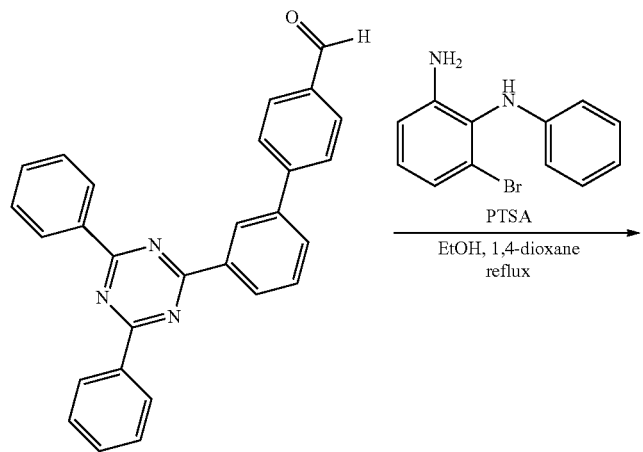
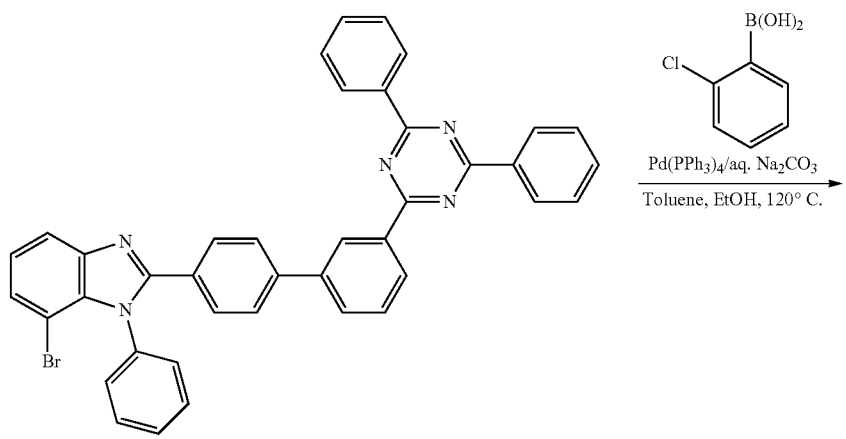
1-1
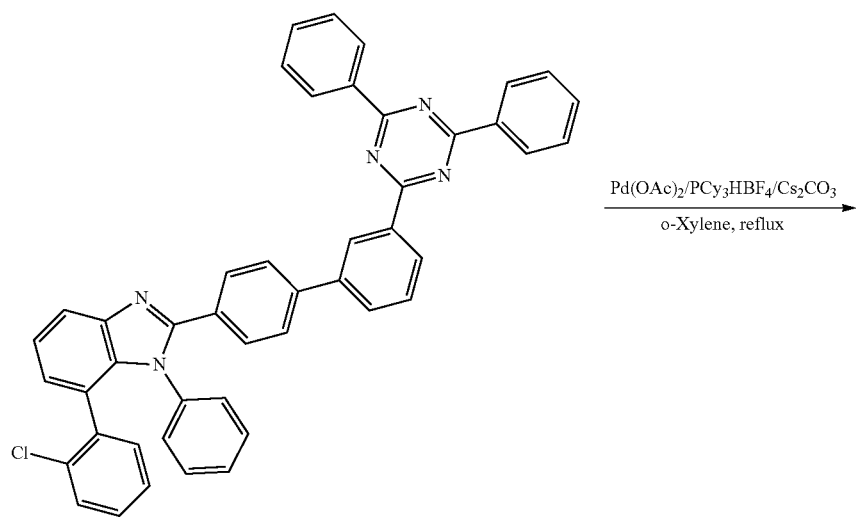
1-2

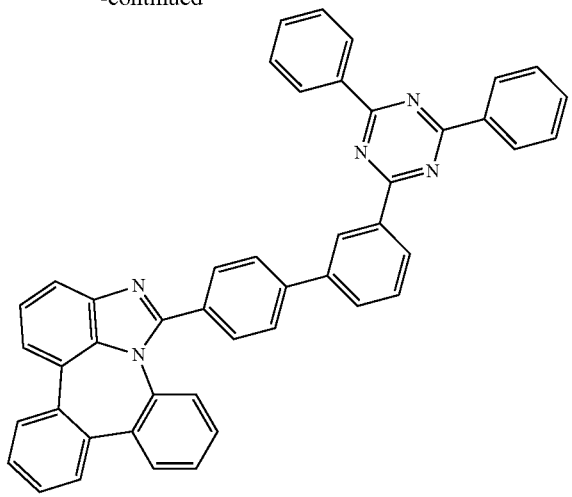

C-32

Preparation of Compound 1-1

3'-(4,6-diphenyl-1,3,5-triazin-2-yl)-[1,1'-biphenyl]-4-carbaldehyde (15.7 g, 38 mmol), 6-bromo-N-phenyl-benzene-1,2-diamine (10 g, 38 mmol), and para-toluenesulfonic acid (0.7 g, 4 mmol), 100 mL of ethanol, and 100 mL of 1,4-dioxane were added into a reaction vessel and refluxed for 24 hours. After completion of the reaction, the organic layer mixture was cooled to room temperature and filtered to obtain compound 1-1 (10 g, yield: 41%).

Preparation of Compound 1-2

Compound 1-1 (9 g, 14 mmol), 2-chlorophenyl boronic acid (2.8 g, 18 mmol), tetrakis(triphenylphosphine)palladium(0) (0.5 g, 0.4 mmol), sodium carbonate (3.6 g, 34 mmol), 70 mL of toluene, 17 mL of ethanol, and 17 mL of distilled water were added into a reaction vessel and stirred at 120° C. for 5 hours. After completion of the reaction, the organic layer mixture was cooled to room temperature and then was extracted with ethyl acetate. After the extracted organic layer was dried with magnesium sulfate, the solvent was removed therefrom with a rotary evaporator. Thereafter, the remaining product was purified by column chromatography to obtain compound 1-2 (8.3 g, yield: 88%).

Preparation of Compound C-32

Compound 1-2 (7.3 g, 11 mmol), palladium(II)acetate (0.2 g, 1 mmol), tricyclohexylphosphine tetrafluoroborate (0.8 g, 2 mmol), cesium carbonate (10.4 g, 32 mmol), and 53 mL of o-xylene were added into a reaction vessel and refluxed for 5 hours. After completion of the reaction, the mixture was washed with distilled water and extracted with ethyl acetate. After the extracted organic layer was dried with magnesium sulfate, the solvent was removed therefrom with a rotary evaporator. Thereafter, the remaining product was purified by column chromatography to obtain compound C-32 (2 g, yield: 29%).

The sample was heated at 10 K/min and the midpoint of the transition was defined as the glass transition temperature (Tg). The glass transition temperature was measured by differential scanning calorimetry (Model Q2000, TA Instruments).

| | MW | UV | PL | M.P. | Tg |
|---|---|---|---|---|---|
| C-32 | 651.77 | 324 nm | 499 nm | 291° C. | 164° C. |

[Device Example 1] Producing a Blue Light-Emitting Organic Electroluminescent Ddvice Containing the Present Compound An OLED device was produced by using the organic electroluminescent compound of the present disclosure. First, a transparent electrode ITO thin film (10 Ω/sq) on a glass substrate for an OLED (GEOMATEC CO., LTD.) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-7}$ torr. Thereafter, an electric current was applied to the cell to evaporate the introduced material, thereby forming a first hole injection layer having a thickness of 60 nm on the ITO substrate. And then compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Compound HT-1 was introduced into another cell of the vacuum vapor deposition apparatus. Thereafter, an electric current was applied to the cell to evaporate the introduced material, thereby forming a first hole transport layer having a thickness of 20 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows.

Compound H-15 as a host was introduced into one cell of the vacuum vapor deposition apparatus and compound D-38 as a dopant was introduced into another cell of the apparatus. The two materials were evaporated at a different rate and the dopant was deposited in a doping amount of 3 wt %, based on the total weight of the host and dopant, to form a light-emitting layer having a thickness of 20 nm on the second hole transport layer. Next, compound C-32 as an electron buffer material was deposited on the light emitting layer to a thickness of 5 nm, and then compound ET-1 as an electron transport material was introduced into one cell and evaporated to deposit an electron transport layer having a thickness of 30 nm on the electron buffer layer. After depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced. For each of the materials, each of the compounds were used by purifying by vacuum sublimation at $10^{-6}$ torr.

[COMPARATIVE EXAMPLES 1 AND 2] A BLUE LIGHT-EMITTING ORGANIC ELECTROLUMINESCENT DEVICE NOT ACCORDING TO THE PRESENT DISCLOSURE

In Comparative Examples 1 and 2, an OLED device was produced in the same manner as in the Device Example 1 except that the electron buffer material shown in Table 1 below was used as the electron buffer material.

The driving voltage of luminance of 1,000 nits, luminous efficiency, and lifespan of 2,000 nits of the organic electroluminescent device of Device Example 1 were measured. As a result, a luminous efficiency of 5.5 cd/A was obtained at a voltage of 4.6 V, and blue light of 1,000 cd/m² was confirmed. Also, the time taken for the emission to reduce from 100% to 90% was 49.3 hours when a constant current is applied at a luminance of 2,000 nits.

The luminous efficiency and the glass transition temperature of Device Example 1 and Comparison Examples 1 and 2 were measured and are shown in the following Table 1.

TABLE 1

|  | Electron Buffer Material | Luminous Efficiency (cd/A) | Glass Transition (Tg) |
|---|---|---|---|
| Device Example 1 | C-32 | 5.5 | 164° C. |
| Comparative Example 1 | A-1 | 4.4 | 116° C. |
| Comparative Example 2 | A-2 | 5.3 | No Detection |

In general, a display device such as a smartphone may instantaneously generate heat to a temperature of 60° C. or higher, and should operate stably even in an extreme temperature condition of −40° C. to 105° C. To satisfy this requirement, the organic electroluminescent material of OLED requires high thermal stability, and thus should have a high glass transition temperature. In general, it is preferable to have a glass transition temperature of 120° C. or higher for commercial use since if the glass transition temperature is low, the material is denatured, thereby making it difficult to achieve the desired device characteristics and losing commercial merit.

Referring to Table 1 above, an OLED device using the organic electroluminescent compound C-32 according to the present disclosure, as an electron buffer material, exhibit characteristics similar to or more excellent than those of conventional compounds in terms of voltage and luminous efficiency, and has a high glass transition temperature. Thus, it can be confirmed that it is advantageous not only for forming a layer by vapor deposition but also for use in a display device such as a smartphone.

The compounds used in the Device Example and Comparative Examples are shown in Table 2 below.

TABLE 2

| Hole Injection Layer/ Hole Transport Layer | 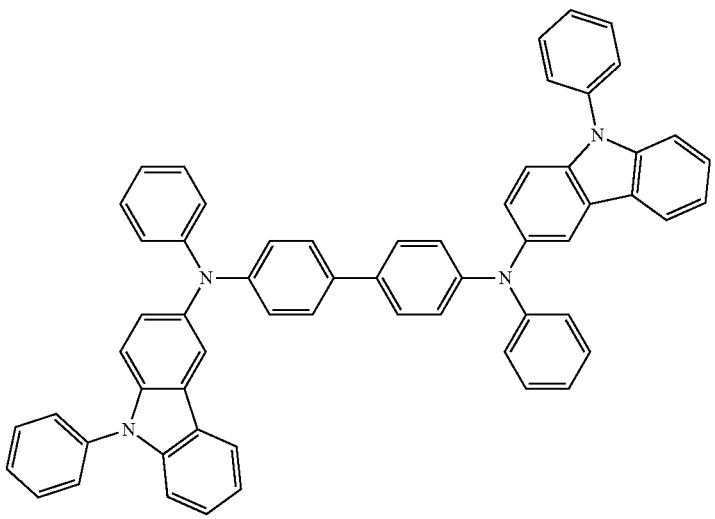 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1] HI-1 |
|---|---|

TABLE 2-continued
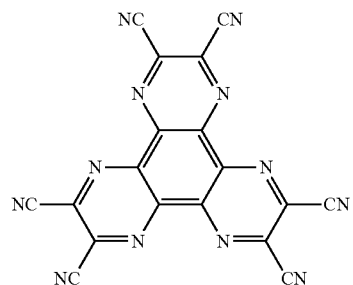 [SMILES: N#Cc1nc2c3nc(C#N)c(C#N)nc3c3nc(C#N)c(C#N)nc3c2nc1C#N]
HI-2
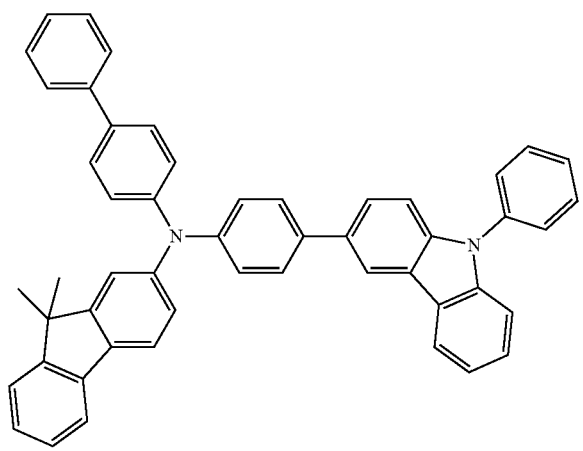 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-1
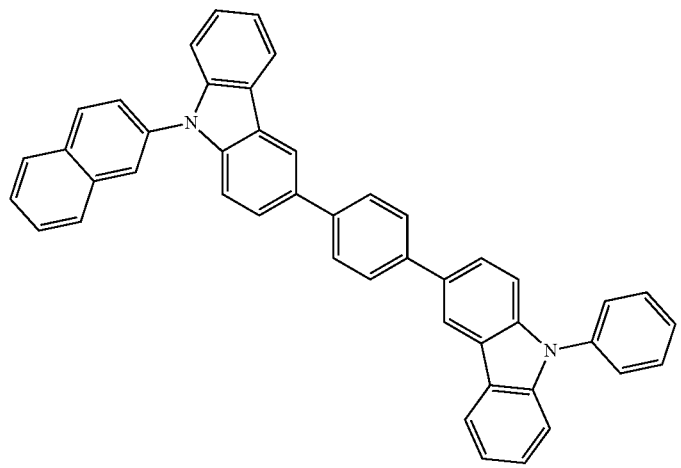 [SMILES: c1ccc(-n2c3ccccc3c3cc(-c4ccc(-c5ccc6c(c5)c5ccccc5n6-c5ccc6ccccc6c5)cc4)ccc32)cc1]
HT-2

TABLE 2-continued
| Light-Emitting Layer | |
|---|---|
| | 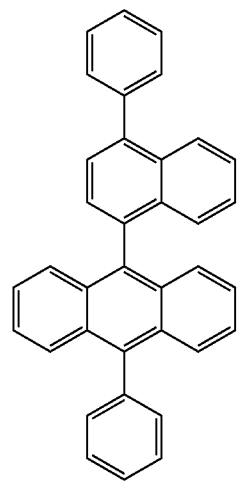 [SMILES: c1ccc(-c2ccc(-c3c4ccccc4c(-c4ccccc4)c4ccccc34)c3ccccc23)cc1]<br>H-15 |
| | 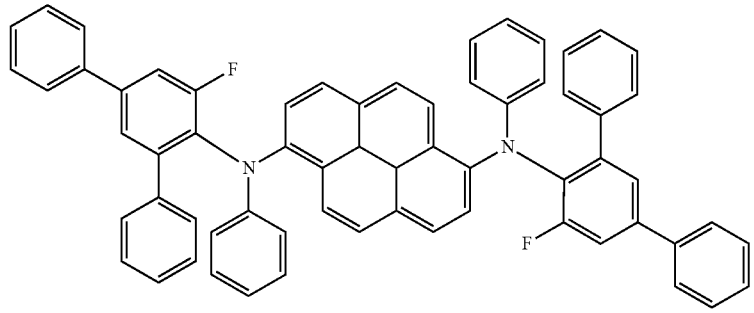 [SMILES: Fc1cc(-c2ccccc2)cc(-c2ccccc2)c1N(C1=CC=C2C=CC3=C(N(c4ccccc4)c4c(F)cc(-c5ccccc5)cc4-c4ccccc4)C=CC4=CC=C1C2C43)c1ccccc1]<br>D-38 |
| Electron Buffer Layer/<br>Electron Transport Layer/<br>Electron Injection Layer | 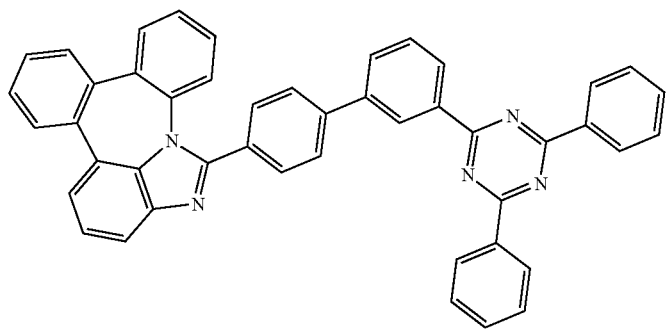 [SMILES: c1ccc(-c2nc(-c3ccccc3)nc(-c3cccc(-c4ccc(-c5nc6cccc7c6n5-c5ccccc5-c5ccccc5-7)cc4)c3)n2)cc1]<br>C-32 |
| | 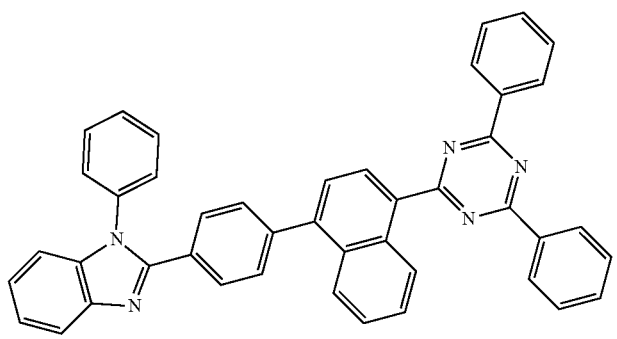 [SMILES: c1ccc(-c2nc(-c3ccccc3)nc(-c3ccc(-c4ccc(-c5nc6ccccc6n5-c5ccccc5)cc4)c4ccccc34)n2)cc1]<br>A-1 |

TABLE 2-continued

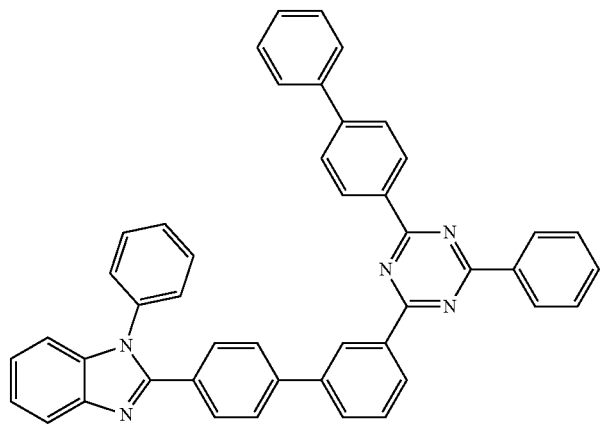 [SMILES: c1ccc(-c2ccc(-c3nc(-c4ccccc4)nc(-c4cccc(-c5ccc(-c6nc7ccccc7n6-c6ccccc6)cc5)c4)n3)cc2)cc1]

A-2

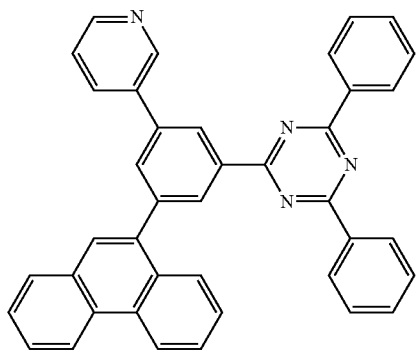 [SMILES: c1ccc(-c2nc(-c3ccccc3)nc(-c3cc(-c4cccnc4)cc(-c4cc5ccccc5c5ccccc45)c3)n2)cc1]

ET-1

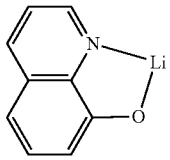

EI-1

The invention claimed is:

1. An organic electroluminescent compound represented by the following formula 1:

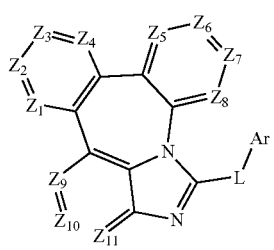

(1)

wherein formula 1, $Z_1$ to $Z_{11}$ each independently represent $CR_1$ or N;

$R_1$ represents hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur;

L represents a single bond, a substituted or unsubstituted (C6-C30)arylene, or a substituted or unsubstituted (5- to 30-membered)heteroarylene;

Ar represents hydrogen, deuterium, halogen, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)ar(C1-C30)alkyl, $-N(R_{11})(R_{12})$, $-Si(R_{13})(R_{14})(R_{15})$, $-S(R_{16})$, $-O(R_{17})$, cyano, nitro or hydroxy;

R$_{11}$ to R$_{17}$ each independently represent hydrogen, deuterium, halogen, a substituted or unsubstituted (C1-C30)alkyl, a substituted or unsubstituted (C6-C30)aryl, a substituted or unsubstituted (5- to 30-membered) heteroaryl, a substituted or unsubstituted (3- to 7-membered)heterocycloalkyl, or a substituted or unsubstituted (C3-C30)cycloalkyl; or may be linked to an adjacent substituent to form a substituted or unsubstituted, (C3-C30) mono- or polycyclic, alicyclic or aromatic ring, or a combination of alicyclic and aromatic rings, whose carbon atom may be replaced with at least one heteroatom selected from nitrogen, oxygen, and sulfur;

the heteroaryl(ene) contains at least one heteroatom selected from B, N, O, S, Si, and P.

2. The organic electroluminescent compound according to claim 1, wherein R$_1$, L, Ar and R$_{11}$ to R$_{17}$, the substituents of the substituted (C1-C30)alkyl, the substituted (C6-C30)aryl(ene), the substituted (5- to 30-membered)heteroaryl(ene), the substituted (3- to 7-membered)heterocycloalkyl, the substituted (C3-C30)cycloalkyl, the substituted (C6-C30)ar(C1-C30)alkyl, and the substituted (C3-C30) mono- or polycyclic, alicyclic or aromatic ring, or the combination thereof each independently, represent at least one selected from the group consisting of deuterium; halogen; cyano; carboxyl; nitro; hydroxy; (C1-C30)alkyl; halo(C1-C30)alkyl; (C2-C30)alkenyl, (C2-C30)alkynyl; (C1-C30)alkoxy; (C1-C30)alkylthio, (C3-C30)cycloalkyl; (C3-C30)cycloalkenyl; (3- to 7-membered)heterocycloalkyl; (C6-C30)aryloxy; (C6-C30)arylthio; a (C6-C30)aryl-substituted or unsubstituted (5- to 30-membered)heteroaryl; a (5- to 30-membered)heteroaryl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; a mono- or di-(C1-C30)alkylamino; a (C1-C30)alky-substituted or unsubstituted mono- or di-(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl.

3. The organic electroluminescent compound according to claim 1, wherein,

Z$_1$ to Z$_{11}$ each independently represent CR$_1$ or N;

R$_1$ represents hydrogen, or may be linked to an adjacent substituent to form a (C5-C10) mono- or polycyclic, alicyclic or aromatic ring, or a combination of alicyclic and aromatic rings, whose carbon atom may be replaced with at least one heteroatom selected from nitrogen, oxygen, and sulfur;

L represents a single bond, or a substituted or unsubstituted (C6-C20)arylene;

Ar represents a substituted or unsubstituted (C6-C25)aryl, a substituted or unsubstituted (5- to 25-membered) heteroaryl, or —N(R$_{11}$)(R$_{12}$).

4. The organic electroluminescent compound according to claim 1, wherein

Z$_1$ to Z$_{11}$ each independently represent CR$_1$ or N;

R$_1$ represents hydrogen, or may be linked to an adjacent substituent to form a benzene ring or benzofuran ring;

L represents a single bond, or a (C1-C6)alkyl-substituted or unsubstituted (C6-C20)arylene;

Ar represents an unsubstituted (C6-C20)aryl, at least one (C6-C12)aryl-substituted or unsubstituted (5- to 25-membered)heteroaryl, or —N(R$_{11}$)(R$_{12}$).

5. The organic electroluminescent compound according to claim 1, wherein the compound represented by Formula 1 is at least one selected from the group consisting of:

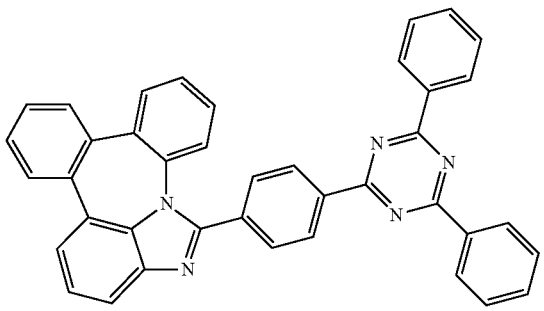

C-1

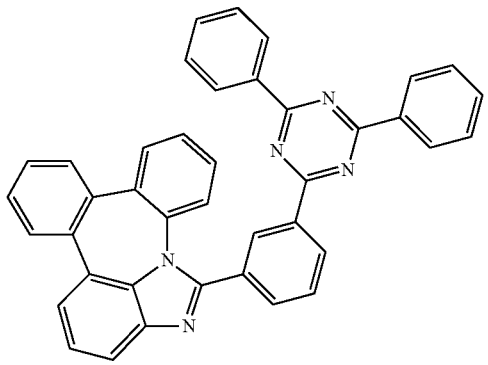

C-2

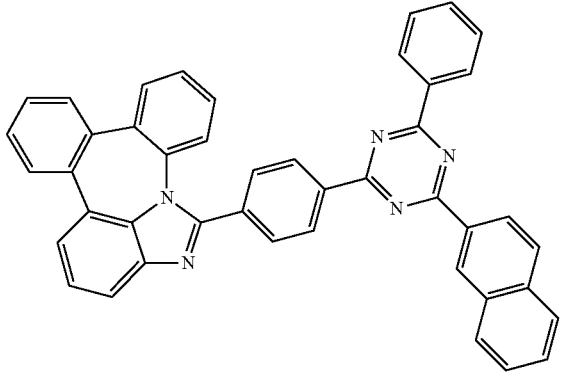

C-3

-continued
C-4
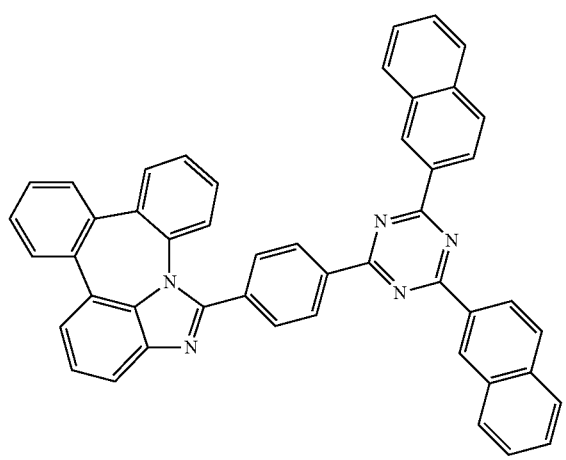
C-5
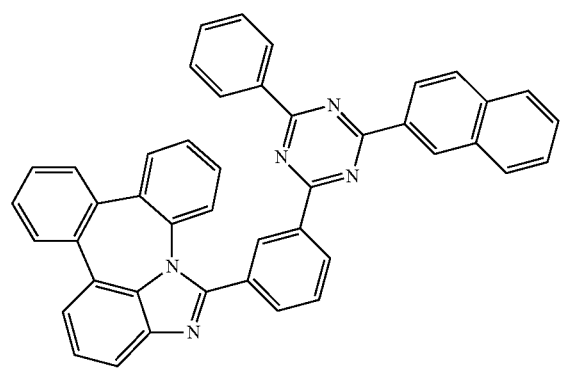
C-6
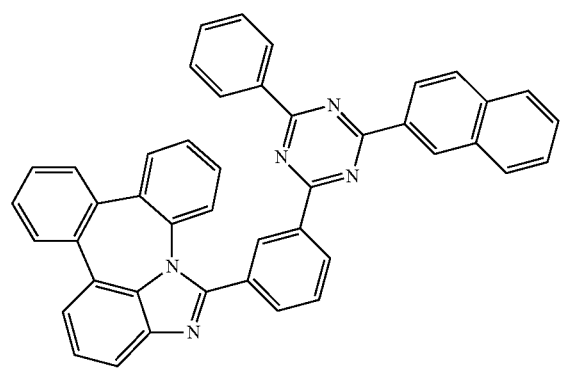
-continued
C-7
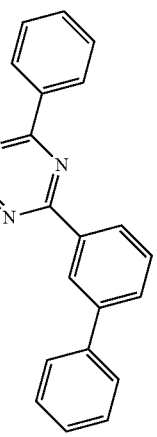
C-8
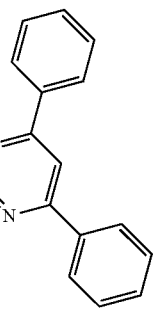
C-9
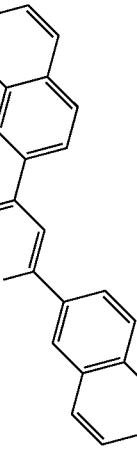
C-10
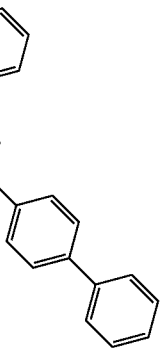

C-11
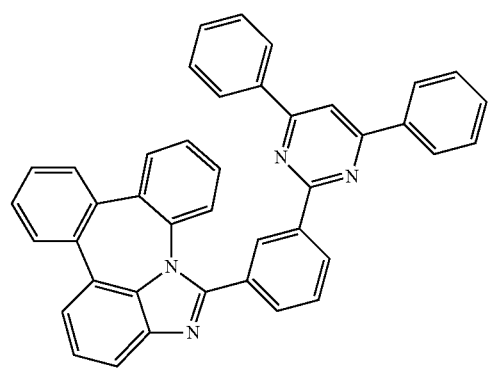
C-15
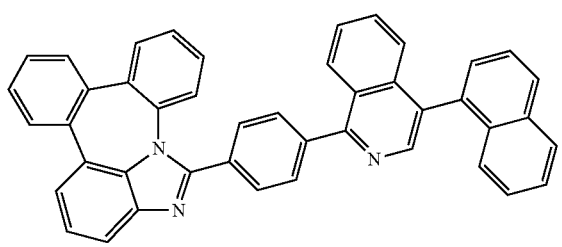
C-16
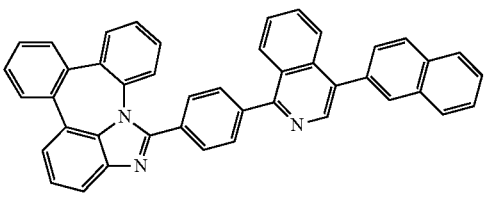
C-12
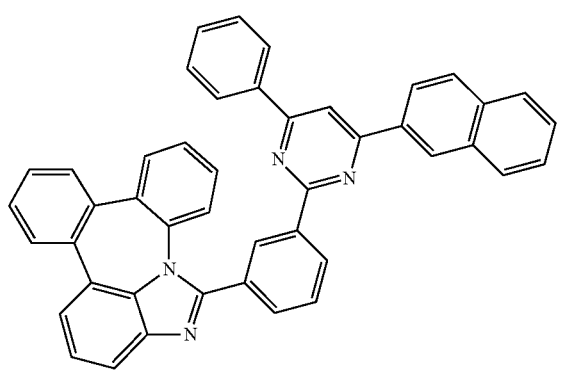
C-17
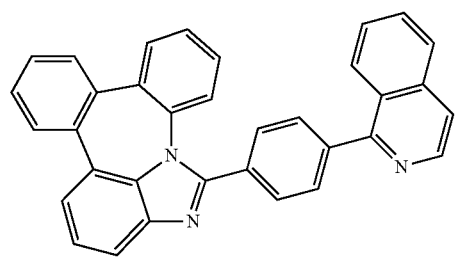
C-18
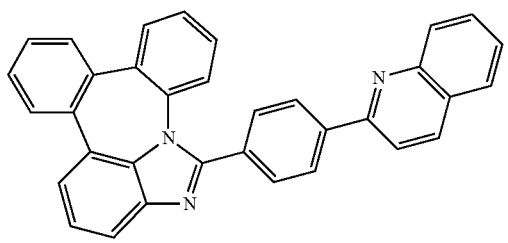
C-13
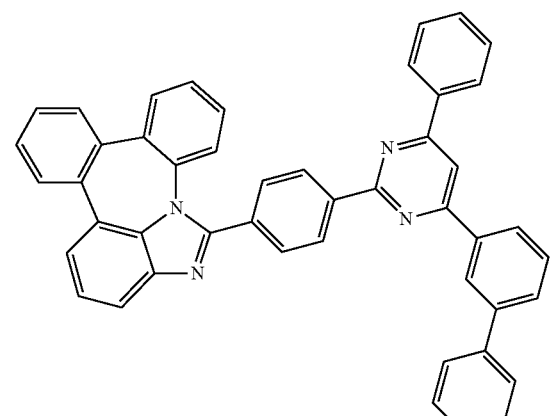
C-19
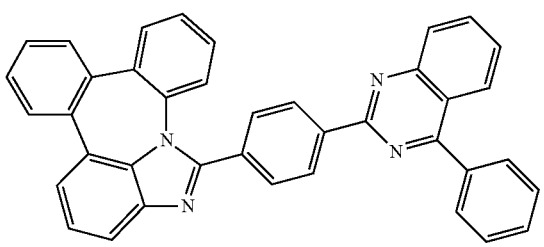
C-14
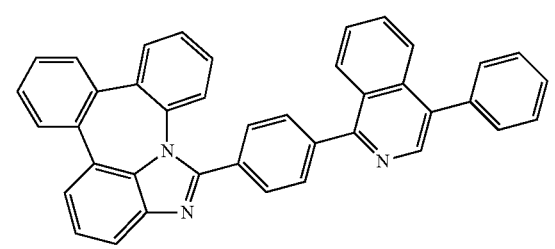
C-20
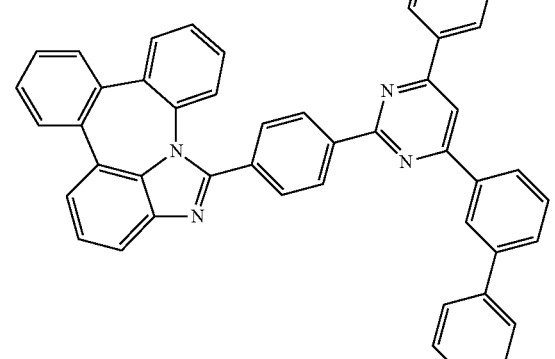

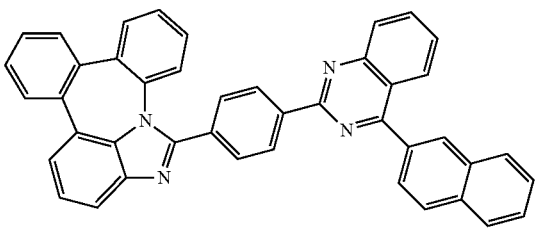
C-21
C-22
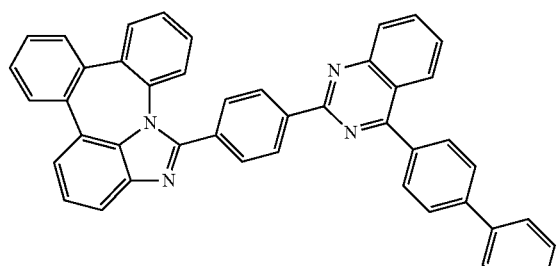
C-23
C-24
C-25
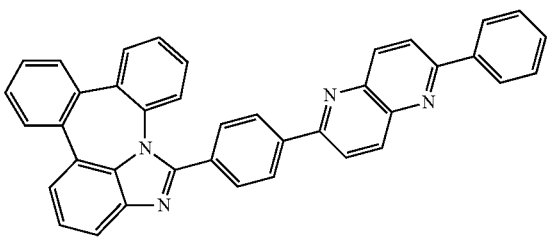
C-26
C-27
C-28
C-29

C-30
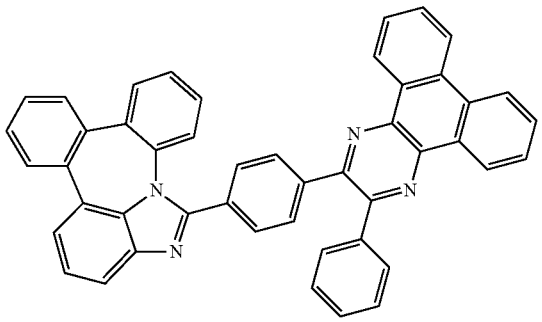
C-34
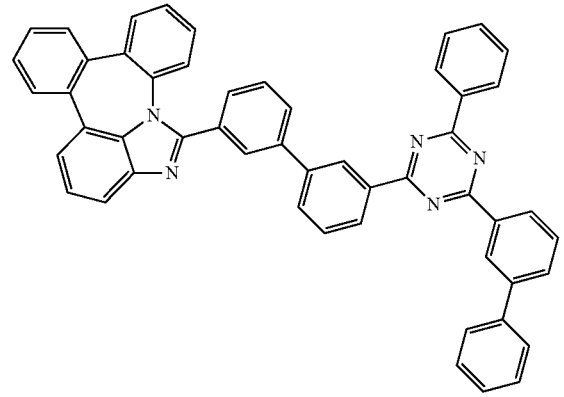
C-31
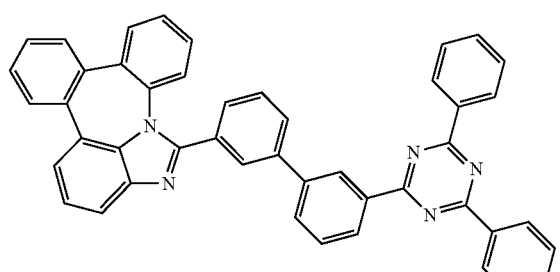
C-35
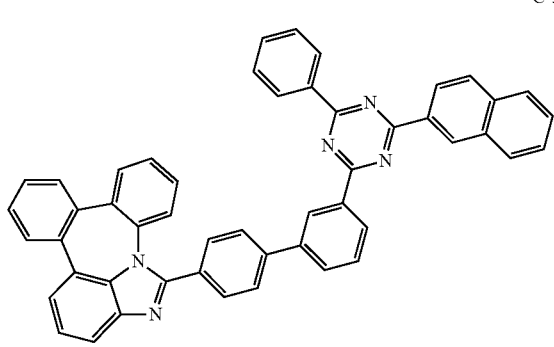
C-32
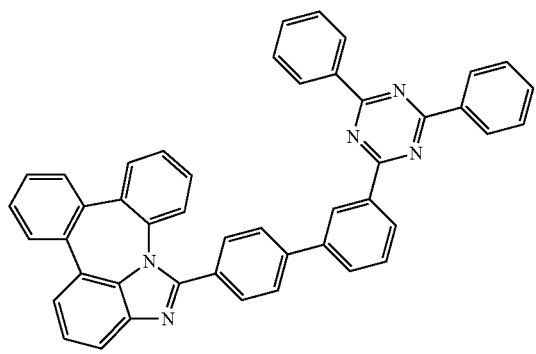
C-36
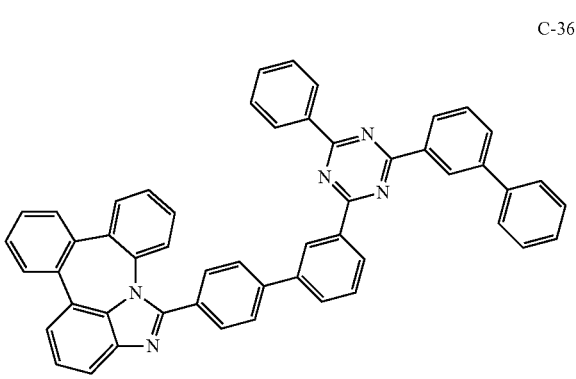
C-33
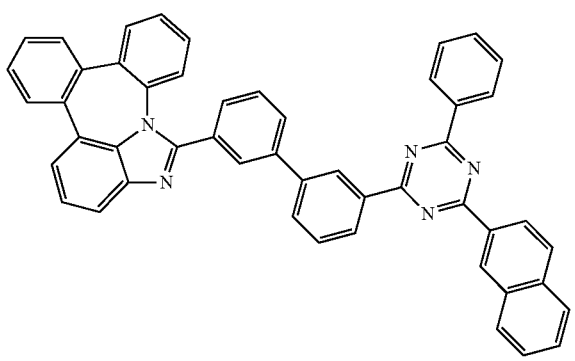
C-37
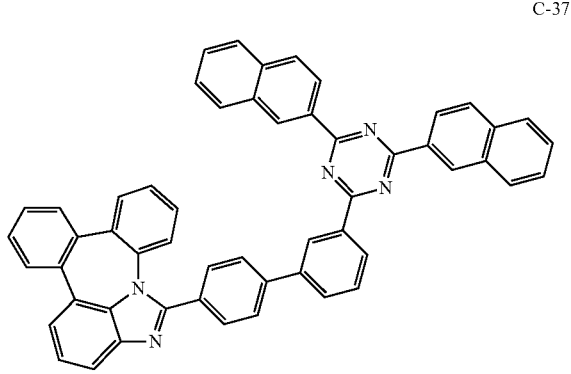

C-38
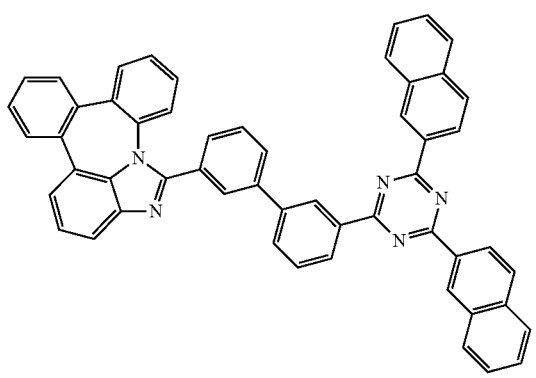
C-39
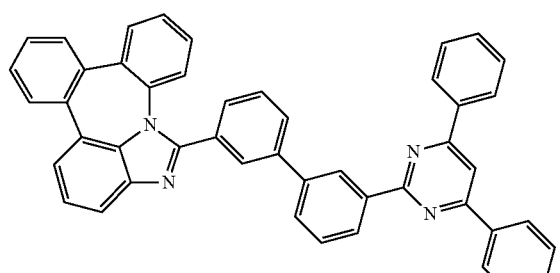
C-40
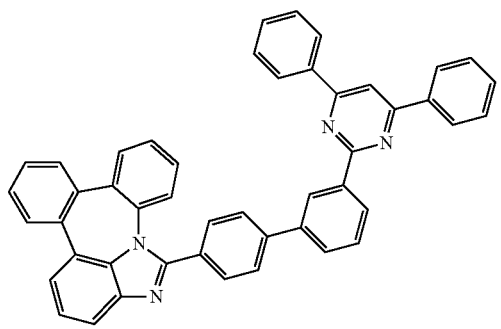
C-41
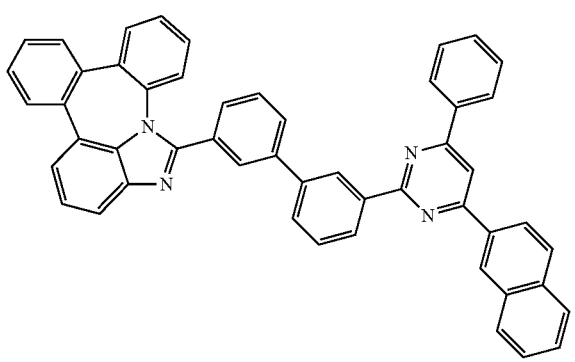
C-42
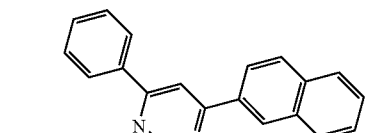
C-43
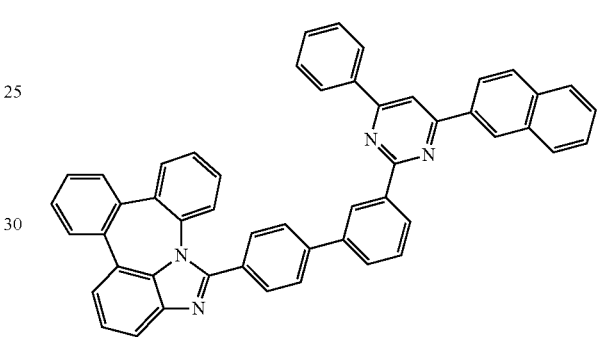
C-44
C-45
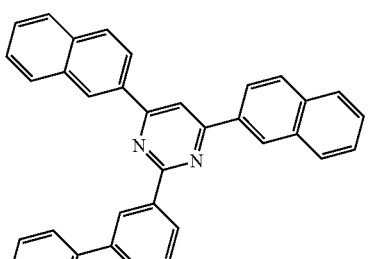

C-46
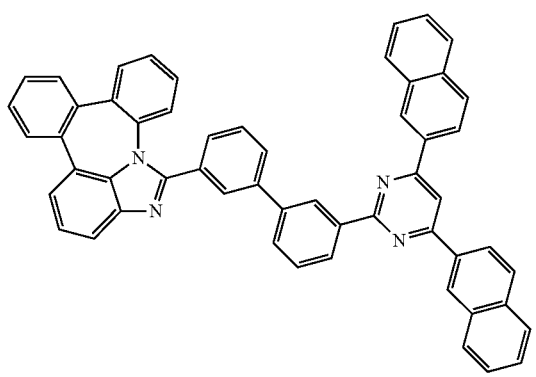
C-47
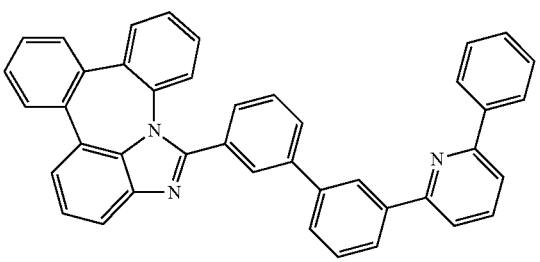
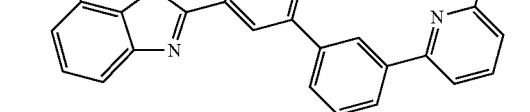
C-48
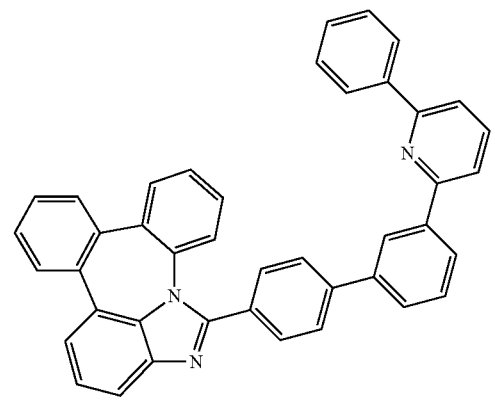
C-49
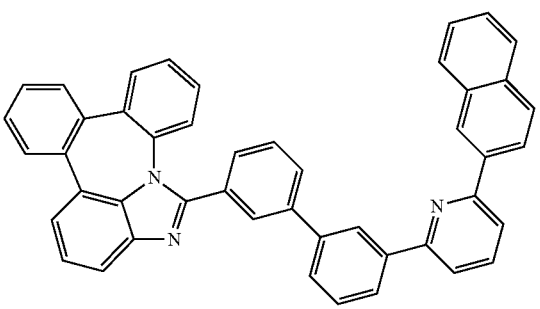
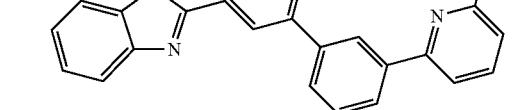
C-50
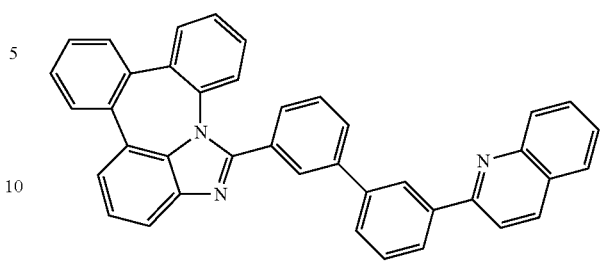
C-51
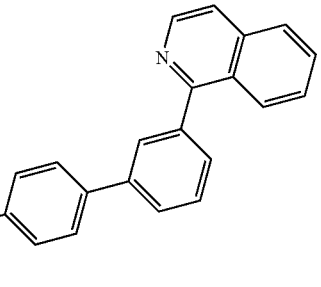
C-52
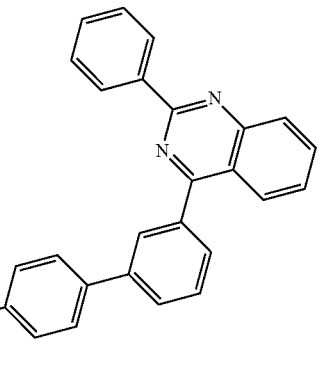
C-53
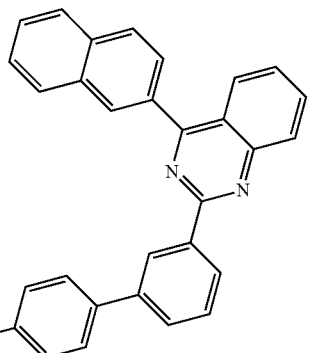

-continued
C-54
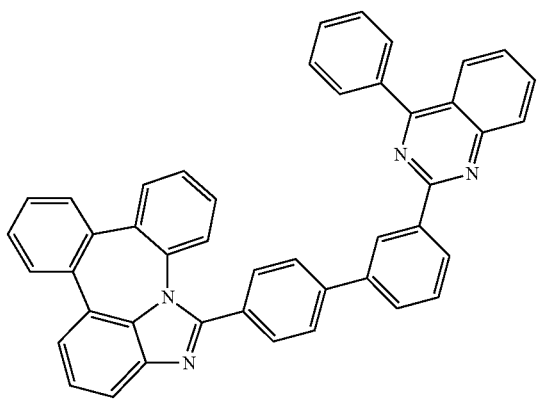
C-55
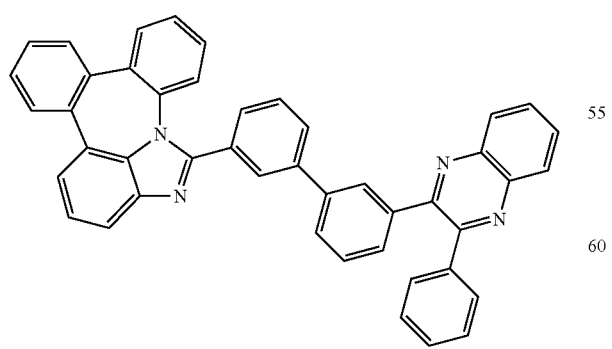
C-56
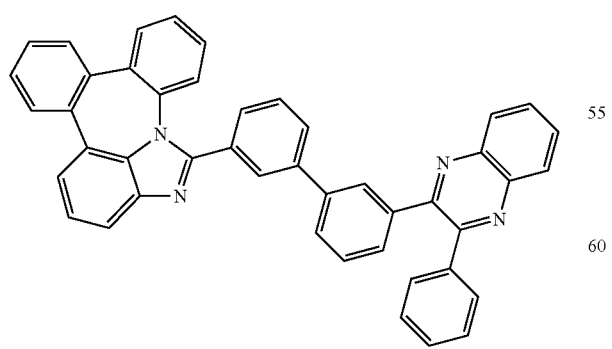
-continued
C-57
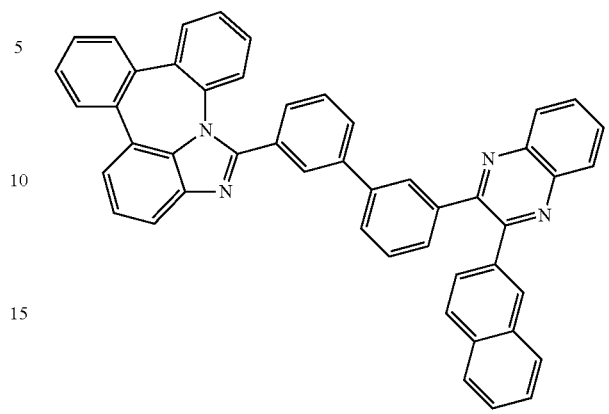
C-58
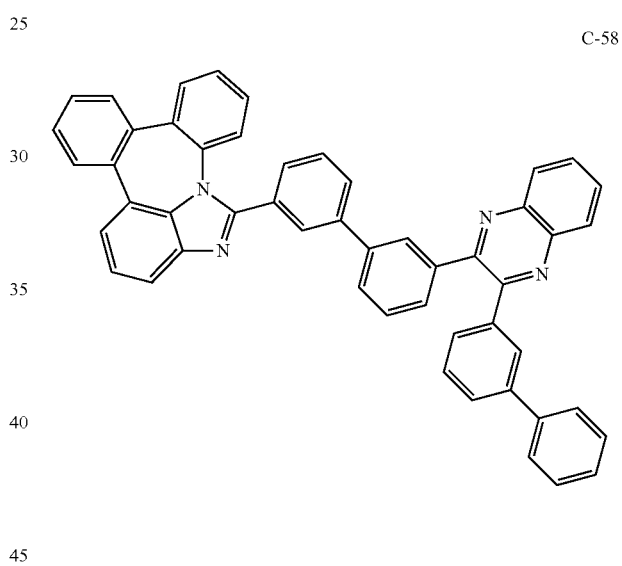
C-59
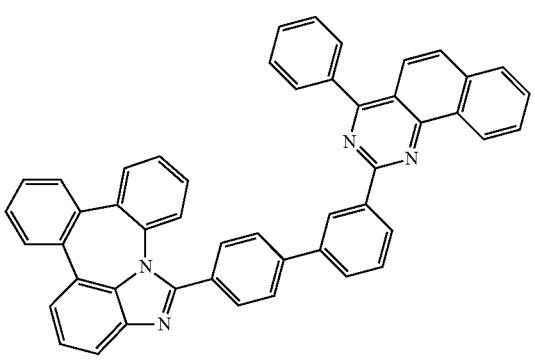

C-60
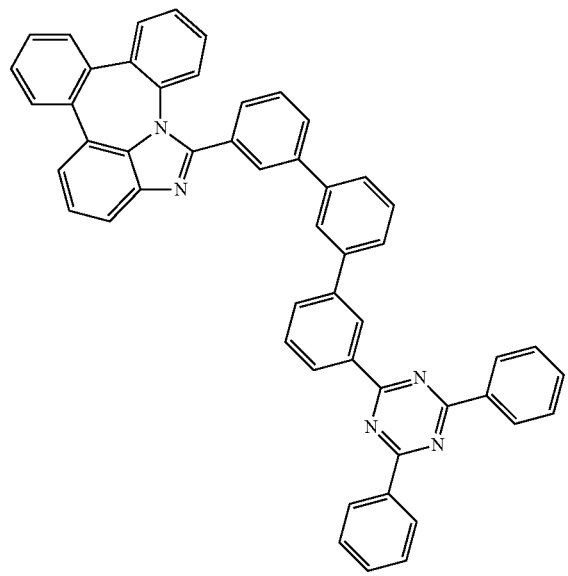
C-61
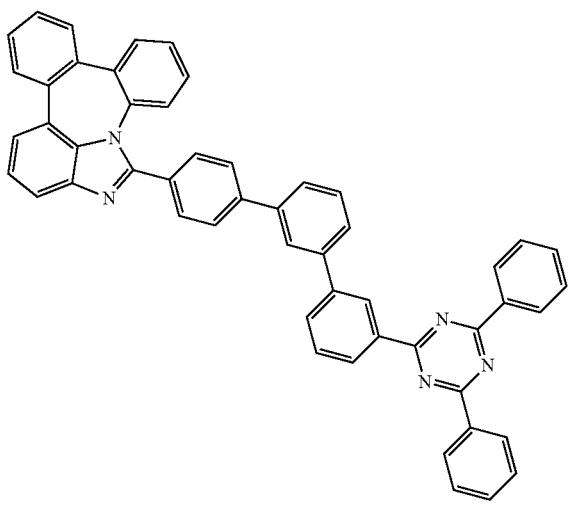
C-62
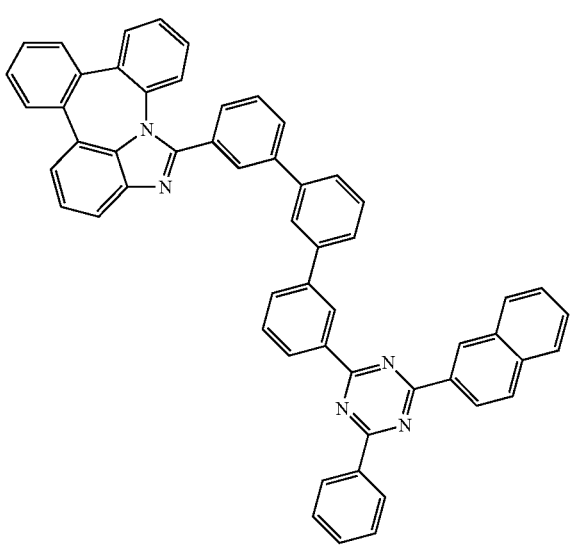
C-63
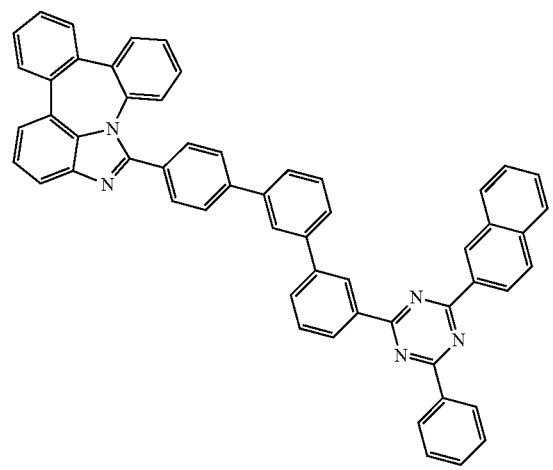
C-64
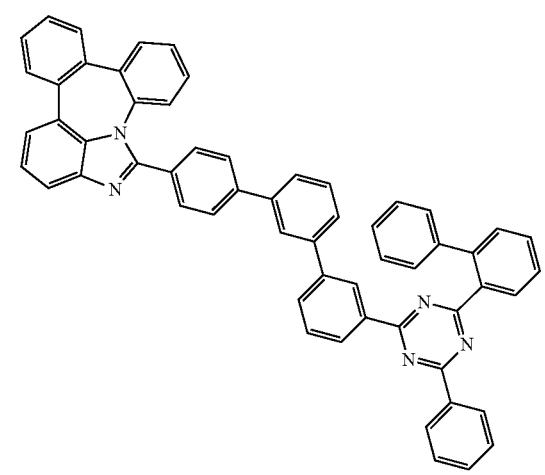
C-65
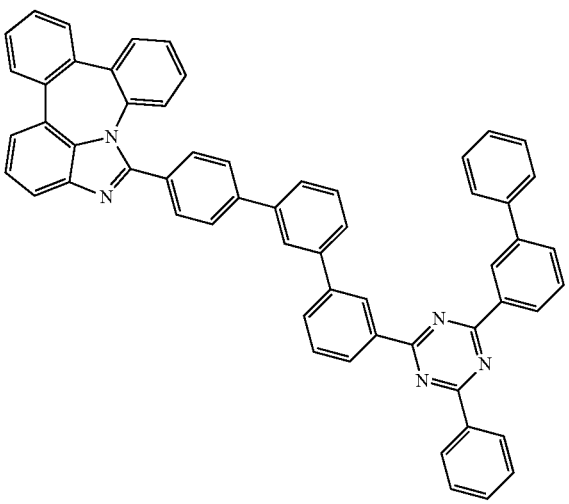

-continued
C-66
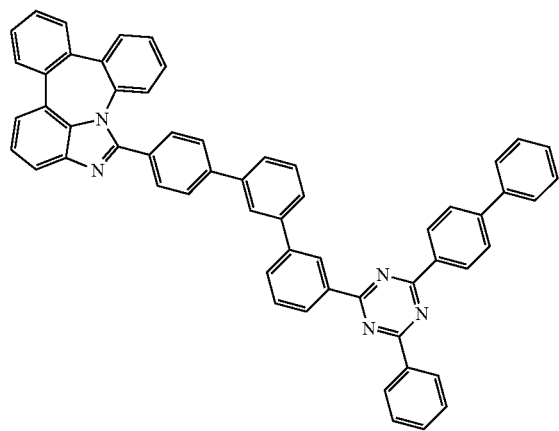
C-67
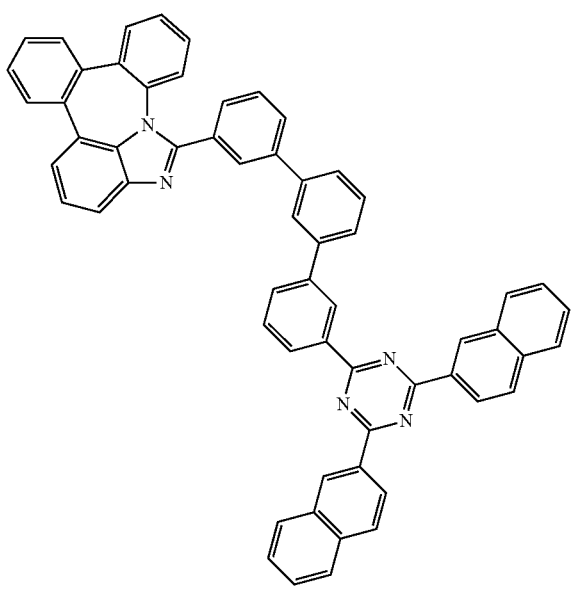
C-68
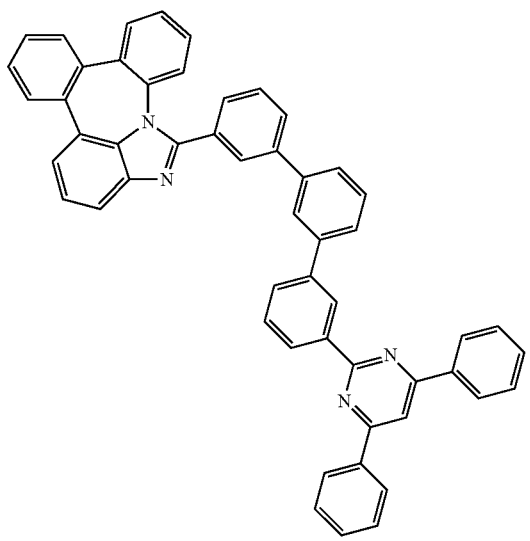
-continued
C-69
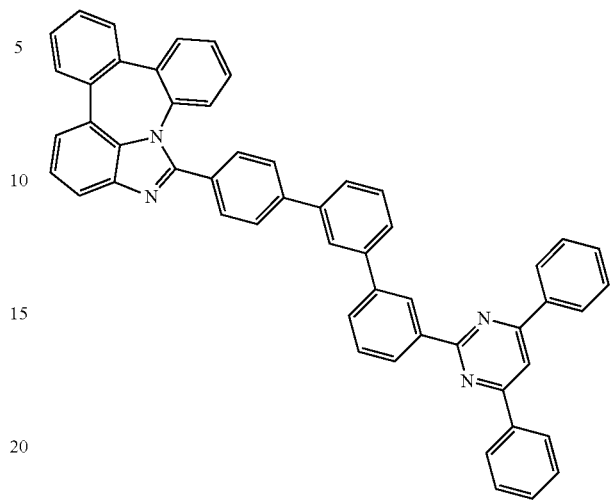
C-70
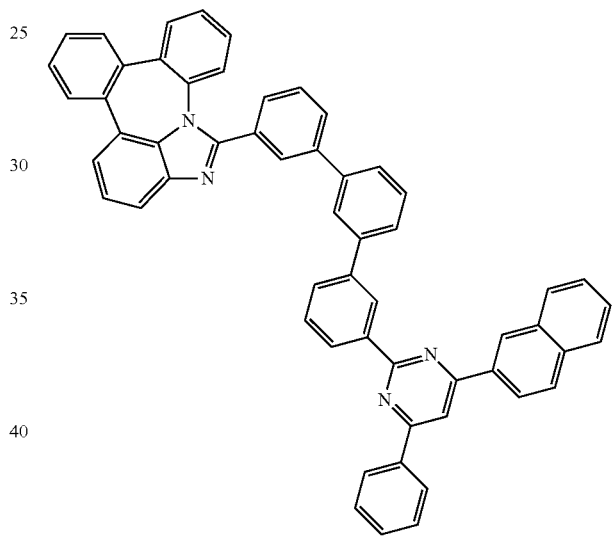
C-71
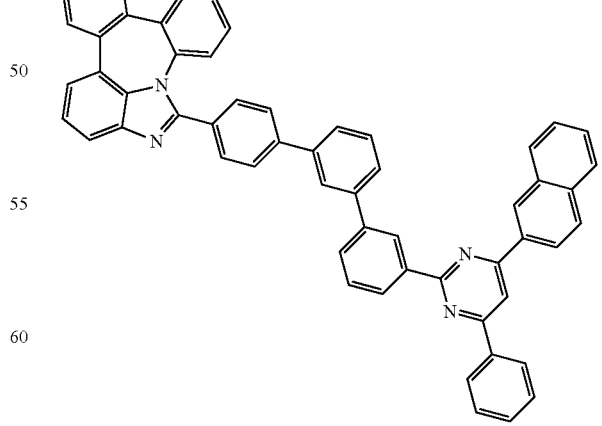

C-72
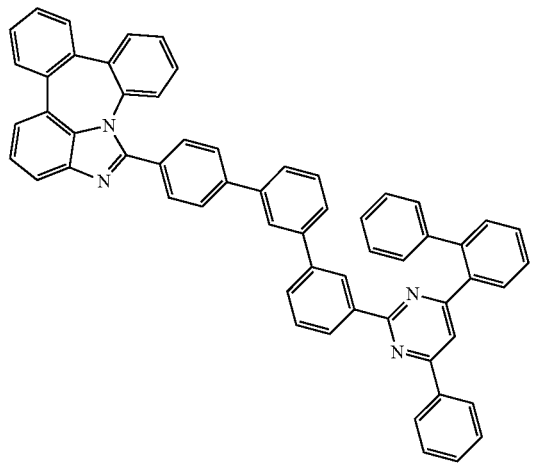
C-73
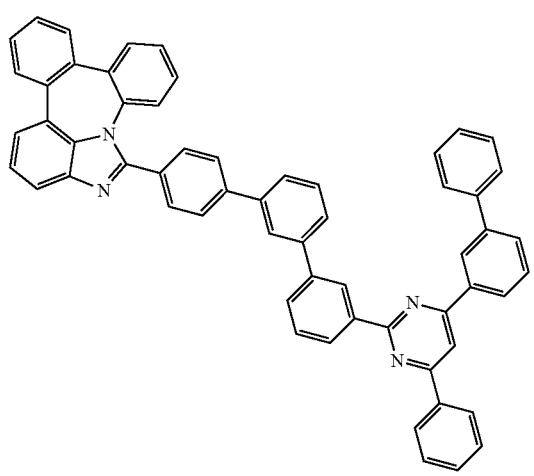
C-74
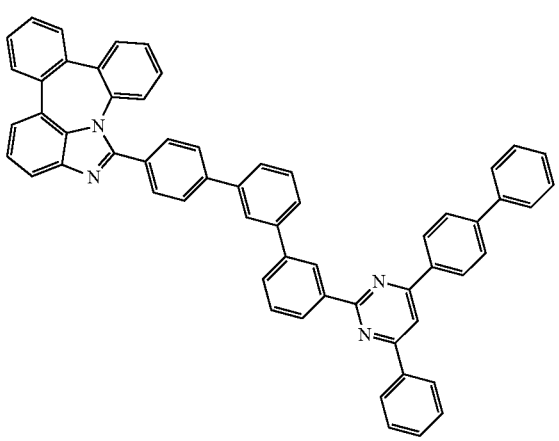
C-75
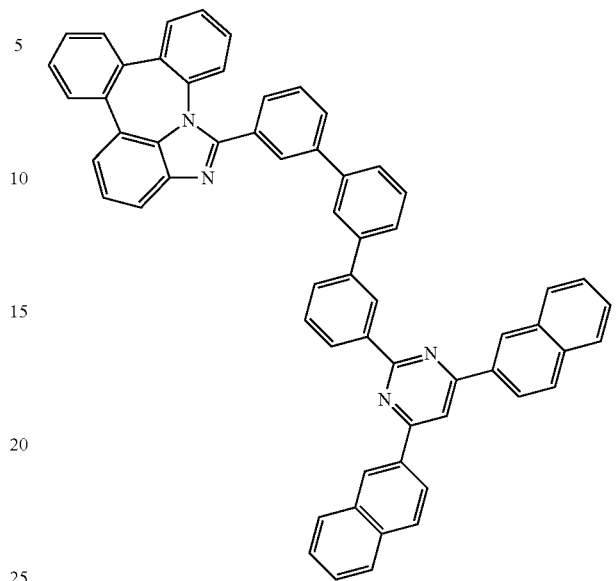
C-76
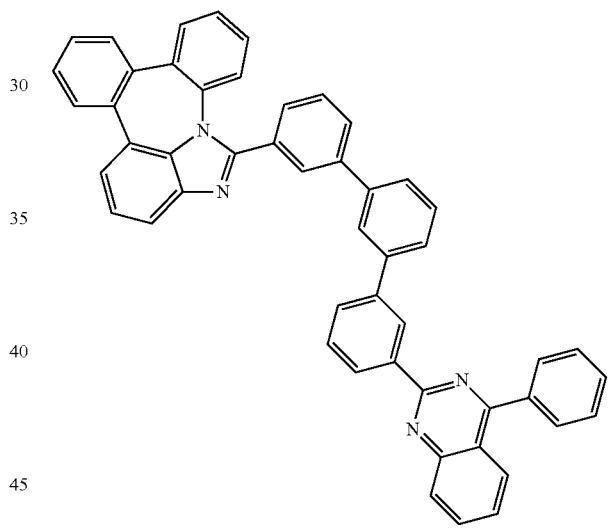
C-77
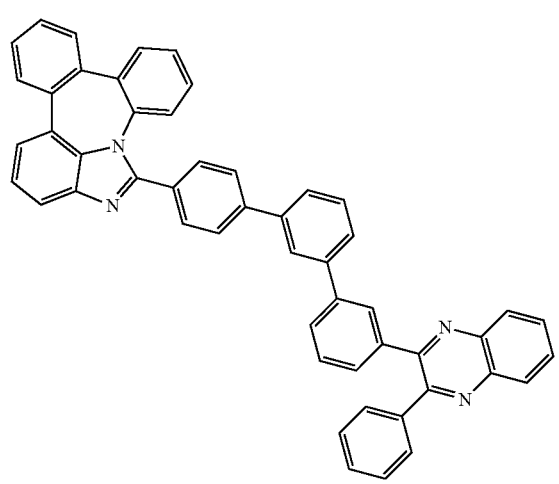

-continued
C-78
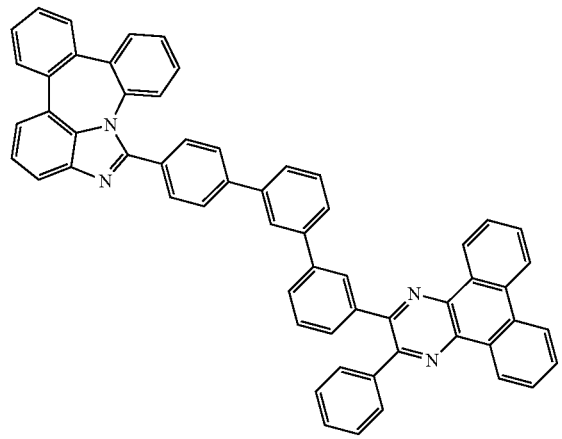
C-79
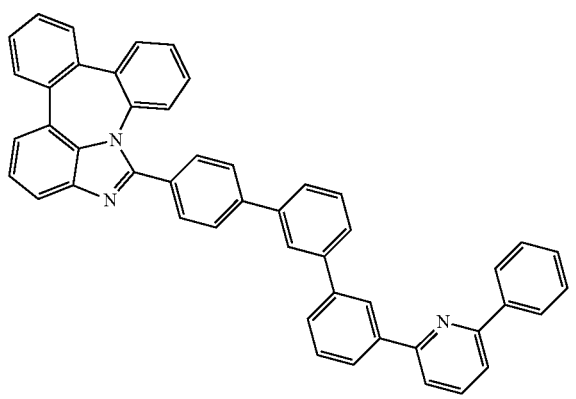
C-80
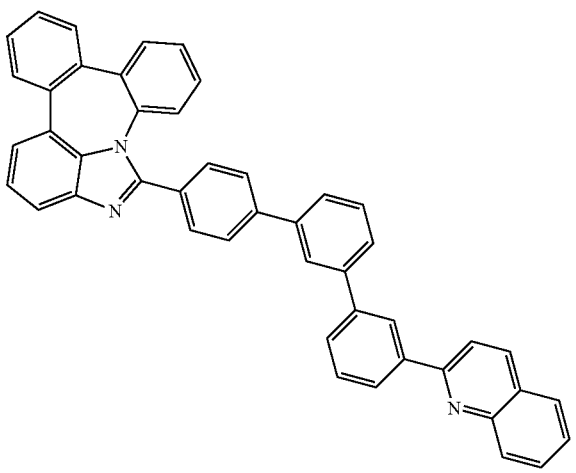
-continued
C-81
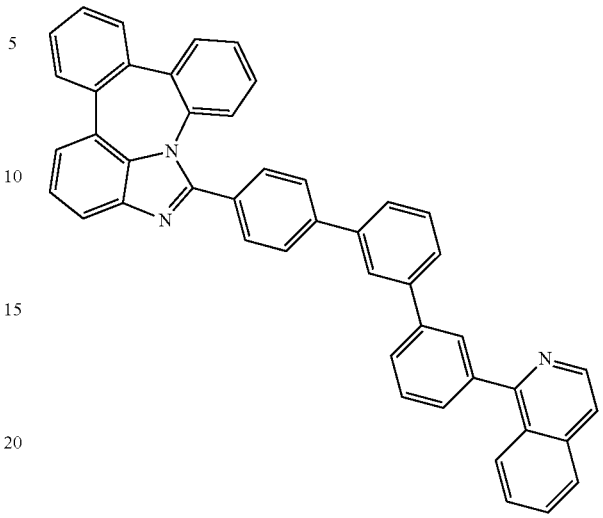
C-82
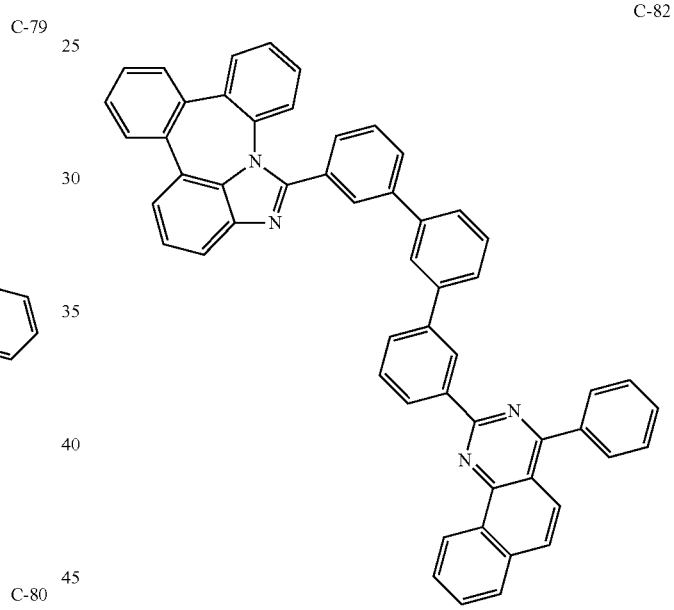
C-83
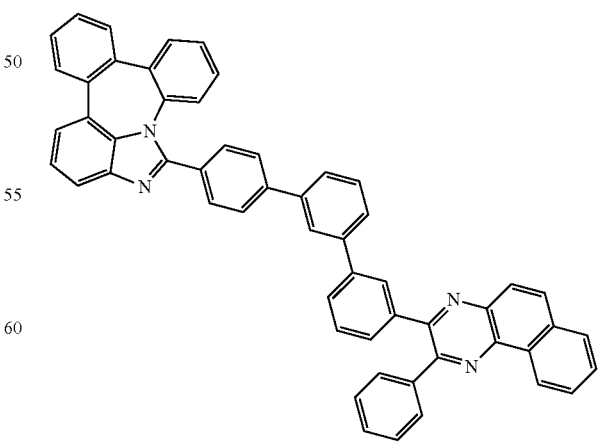

-continued
C-84
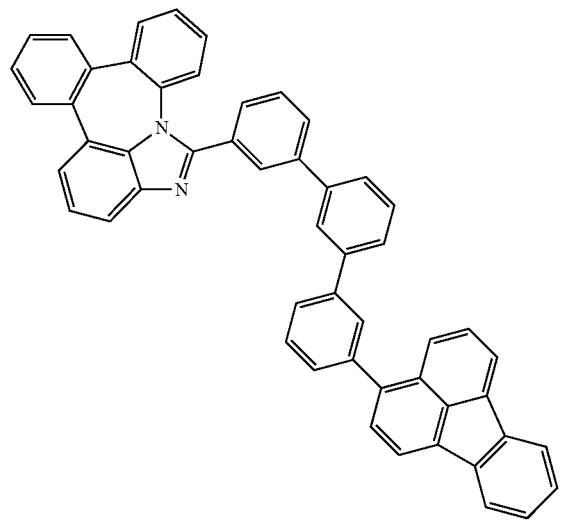
C-85
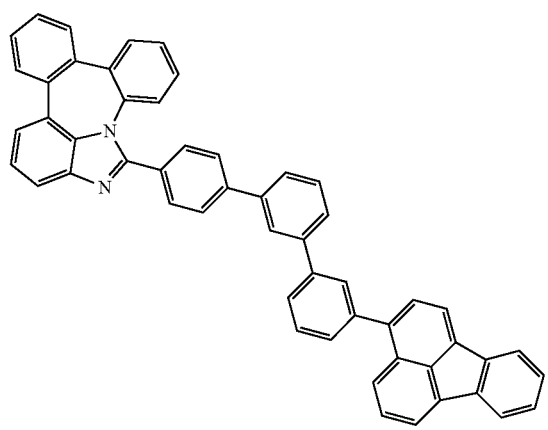
C-86
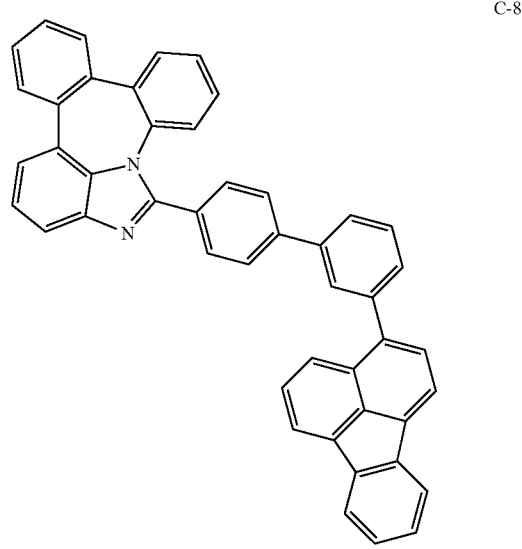
-continued
C-87
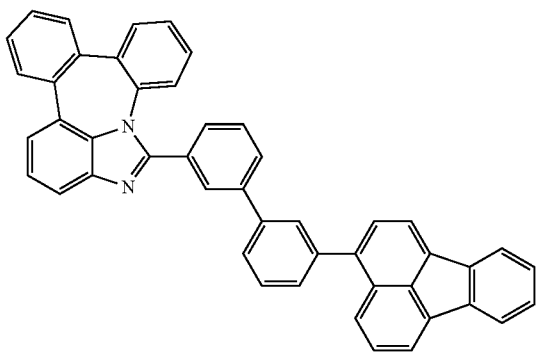
C-88
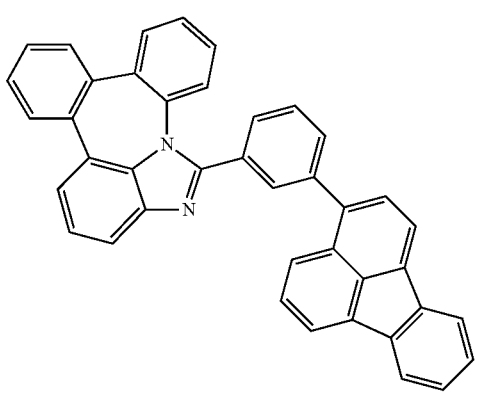
C-89
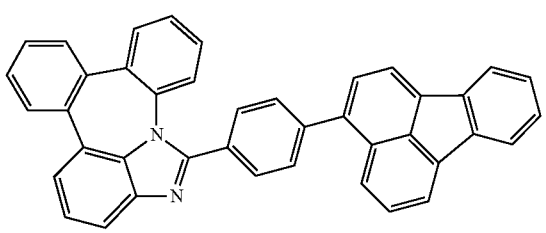
C-90
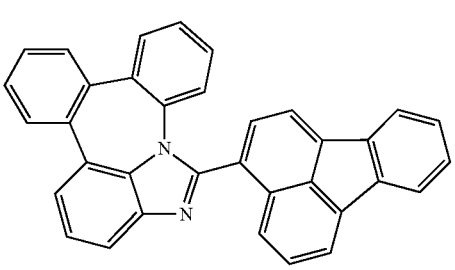

-continued
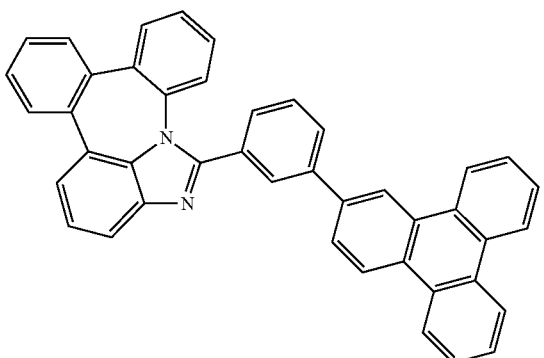
C-91
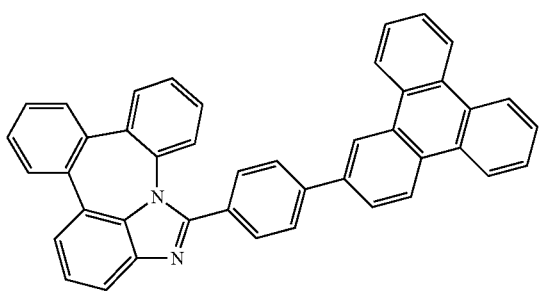
C-92
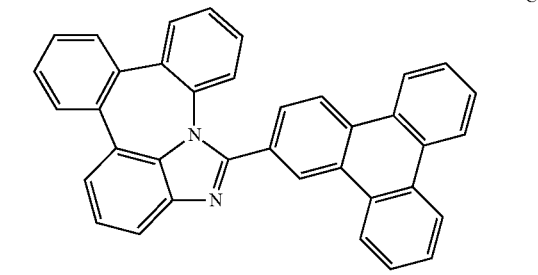
C-93
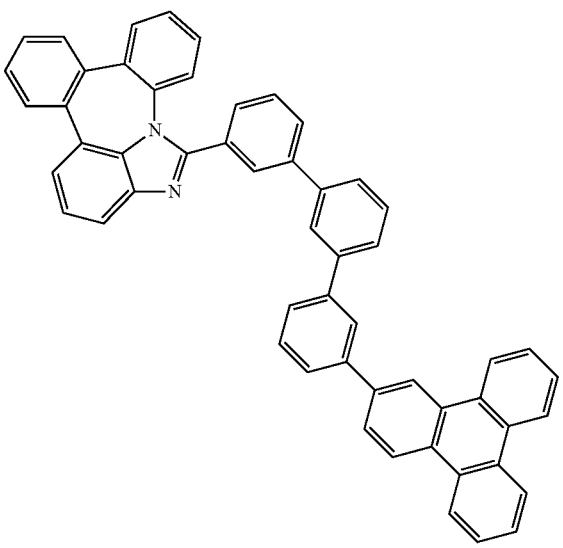
C-94
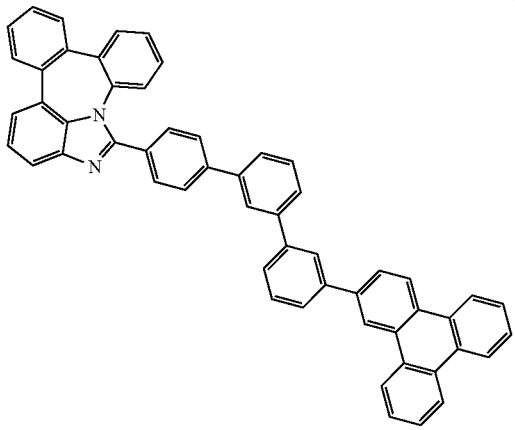
C-95
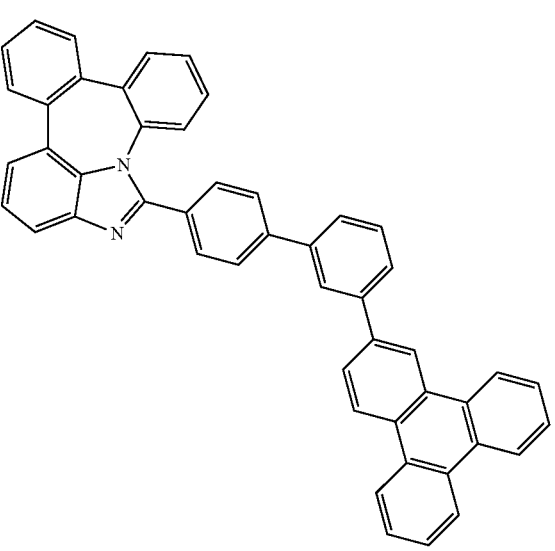
C-96
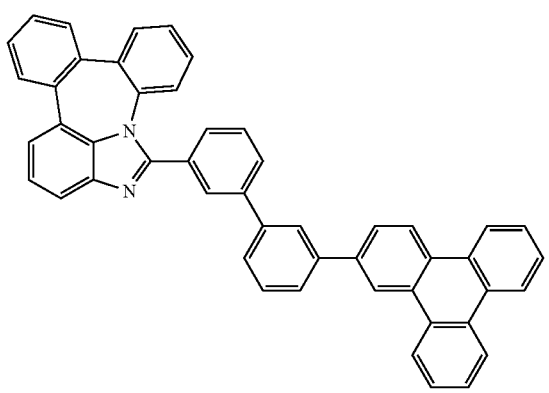
C-97

C-98
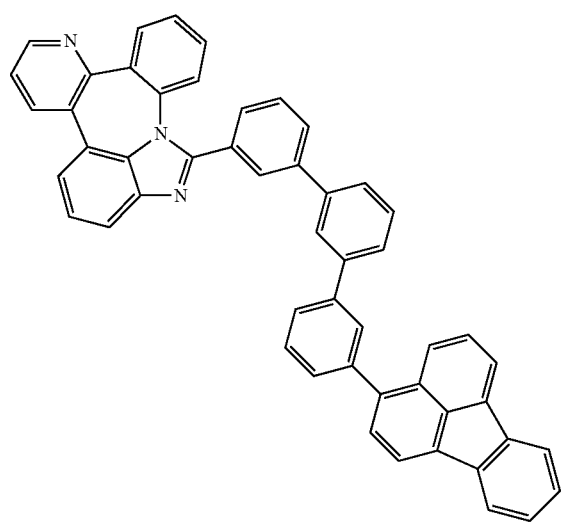
C-99
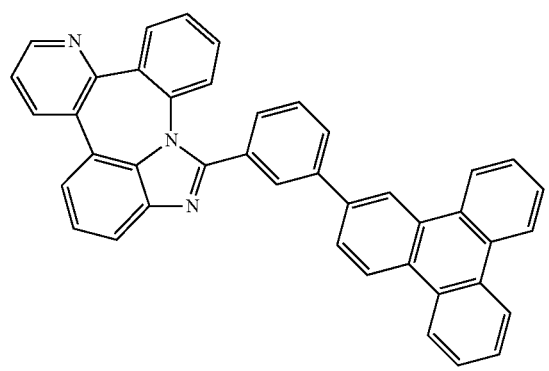
C-100
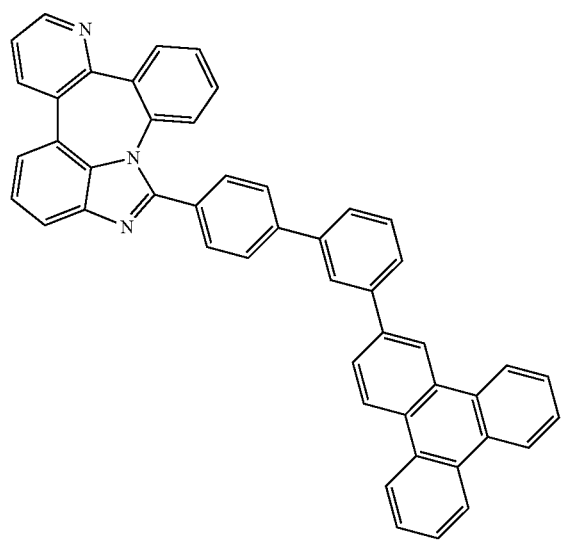
C-101
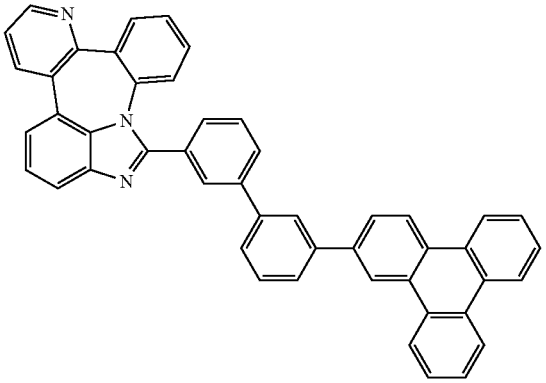
C-102
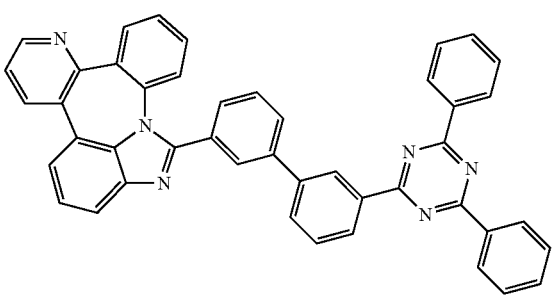
C-103
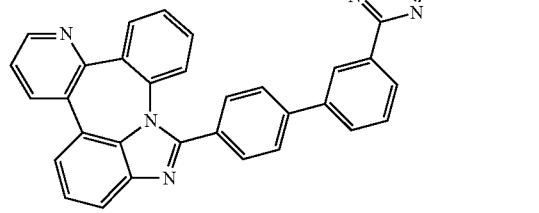
C-104
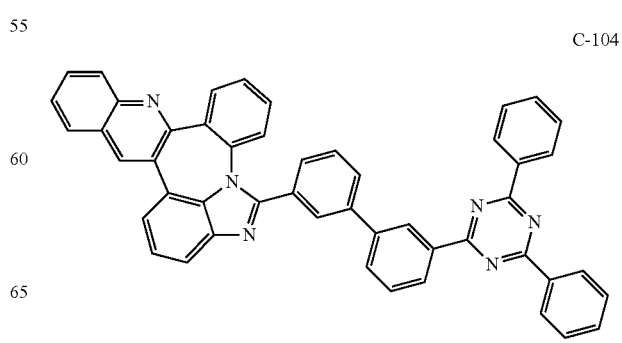

C-105
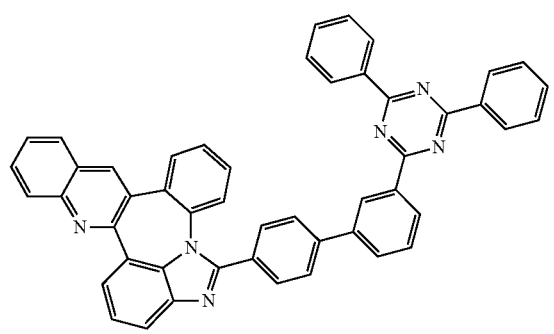
C-108
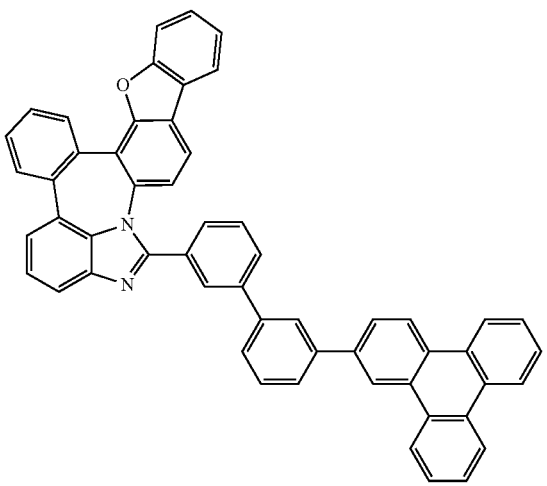
C-106
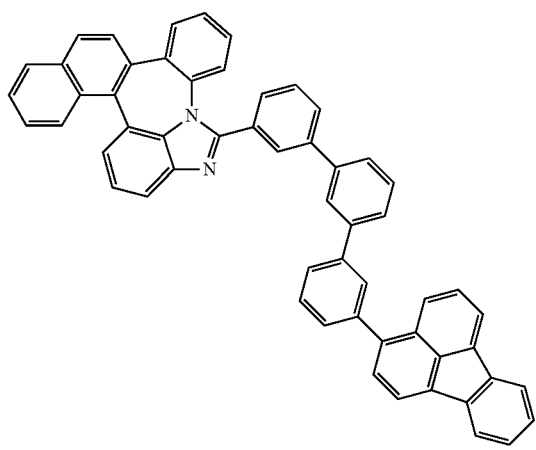
C-109
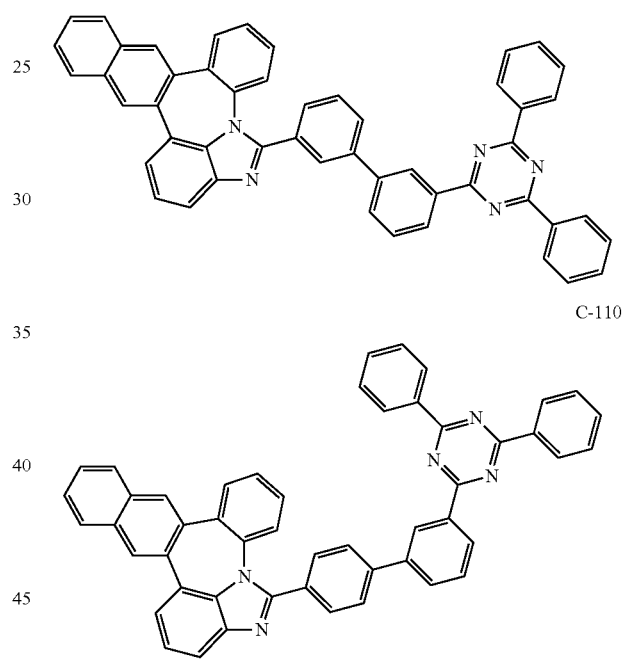
C-110
C-107
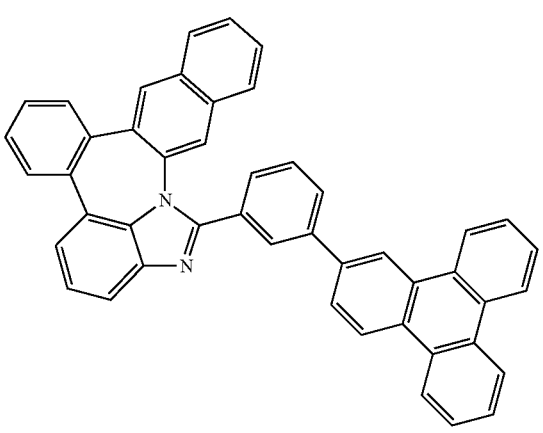
C-111
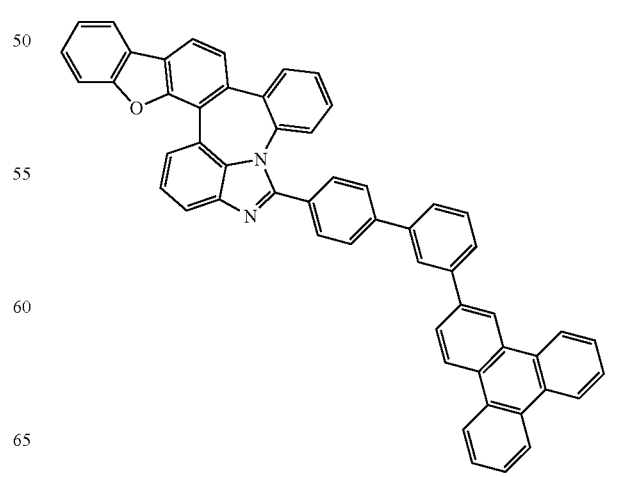

-continued
C-112
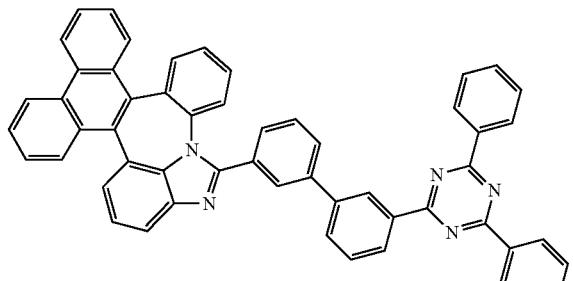
C-113
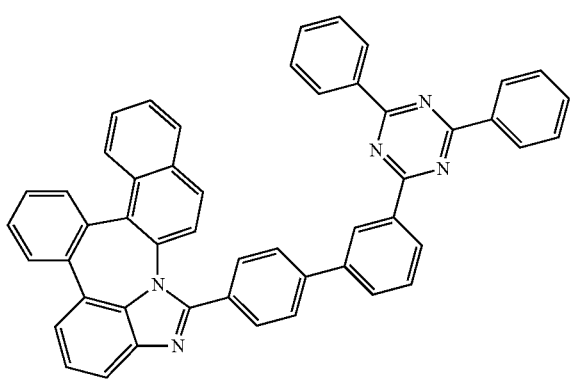
C-114
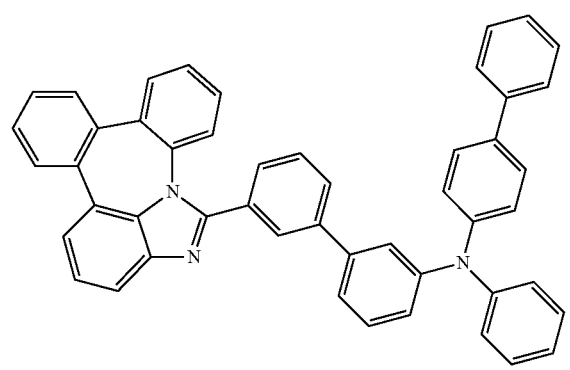
C-115
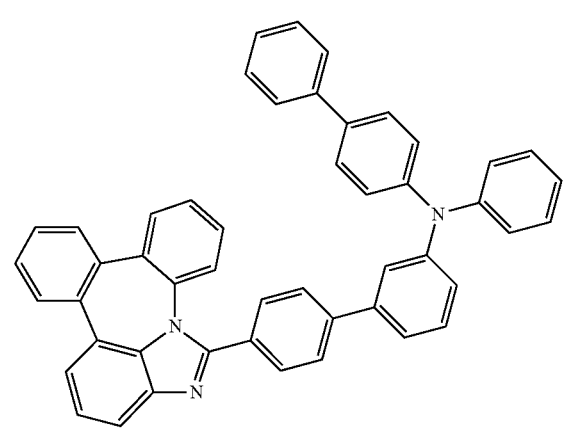
C-116
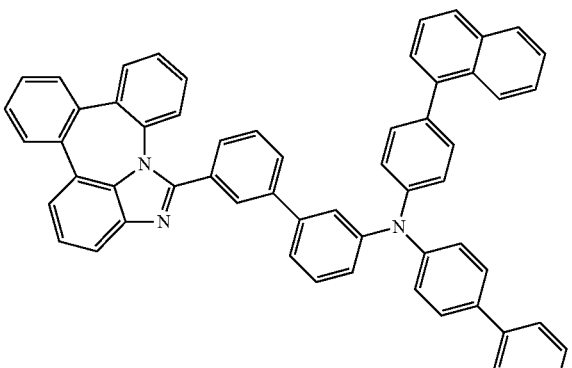
C-117
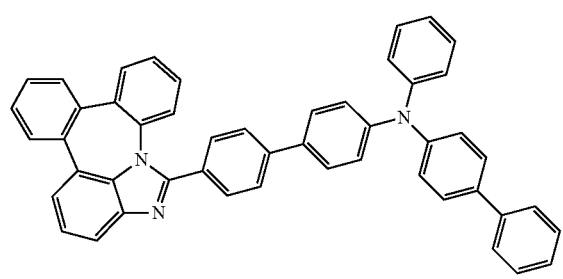
C-118
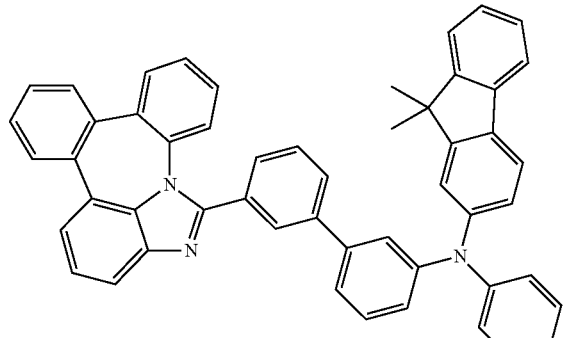
C-119
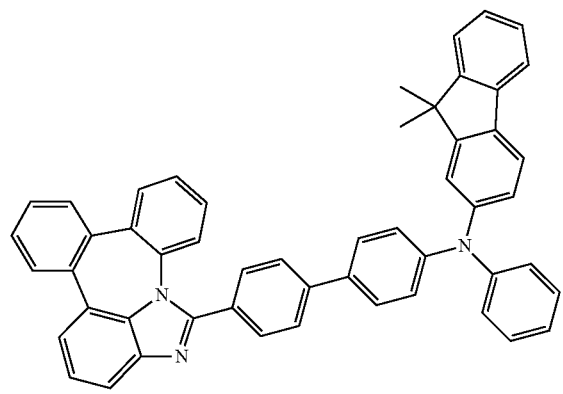

C-120
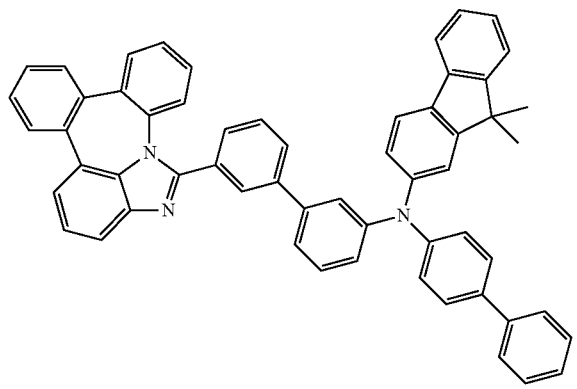
C-121
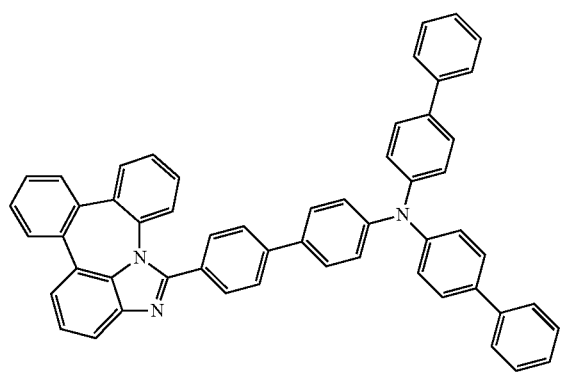
C-122
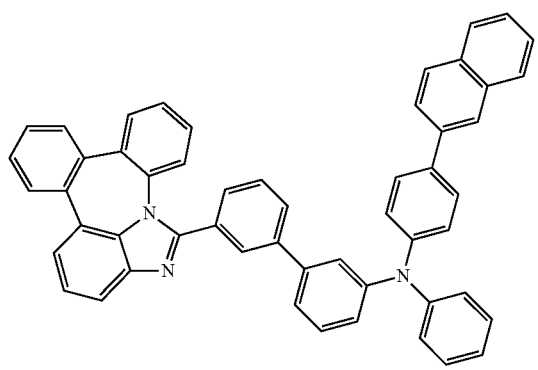
C-123
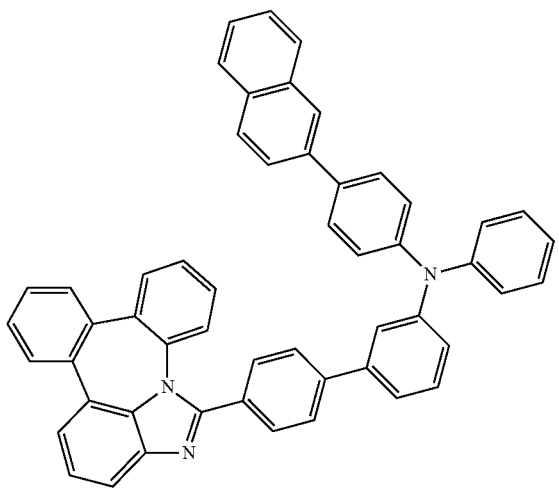
C-124
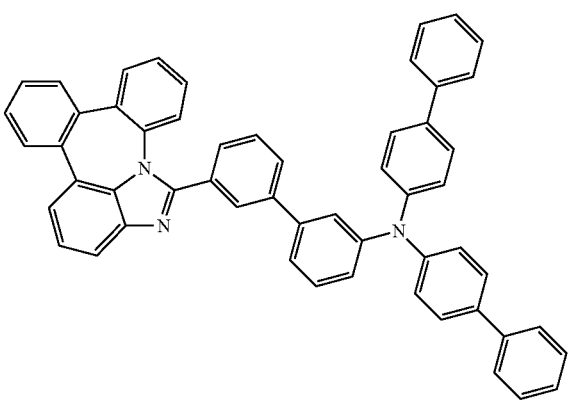
C-125
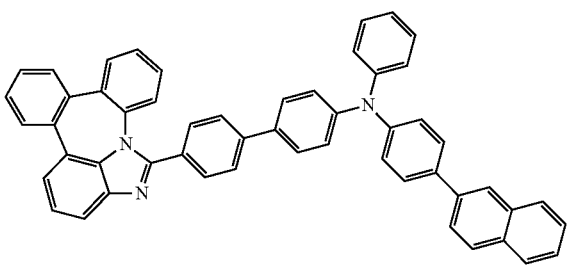
C-126
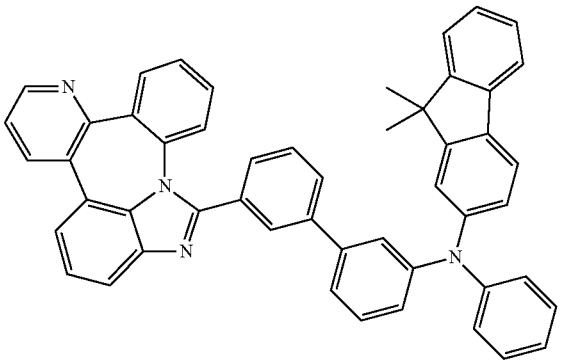

C-127
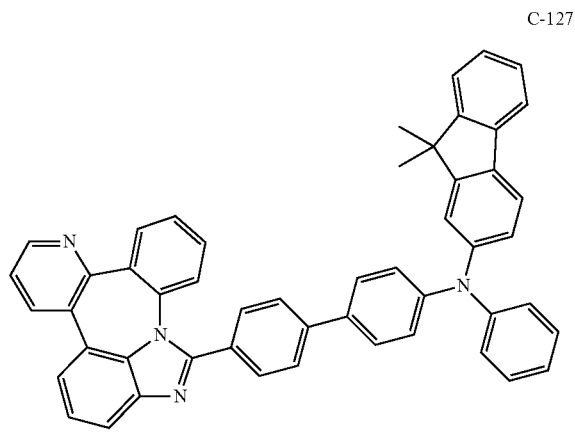
C-128
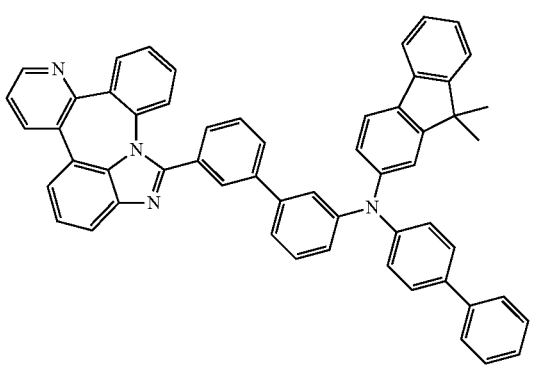
C-129
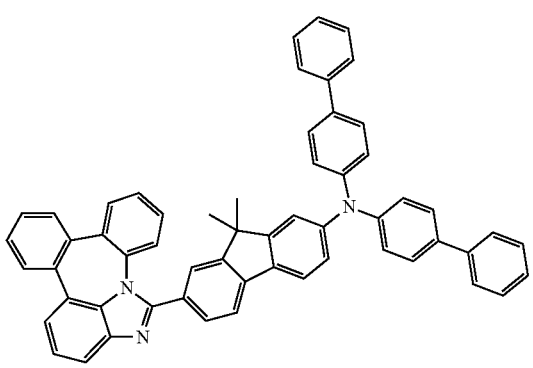
C-130
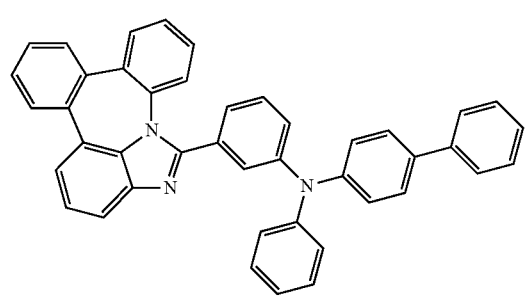
C-131
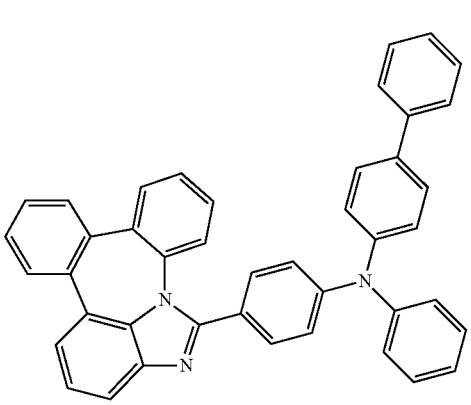
C-132
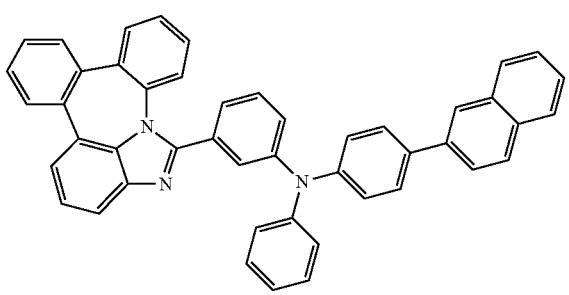
C-133
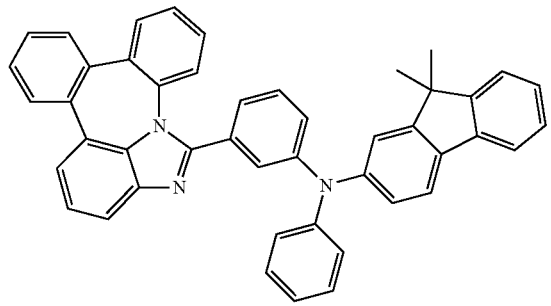
C-134
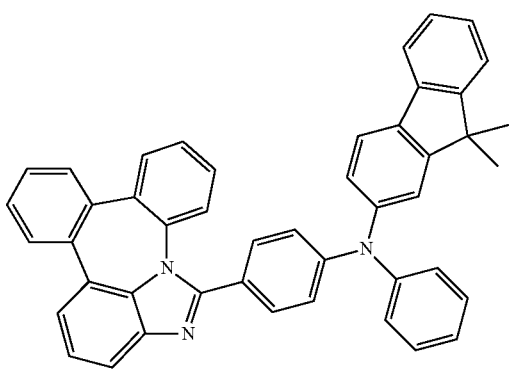

C-135

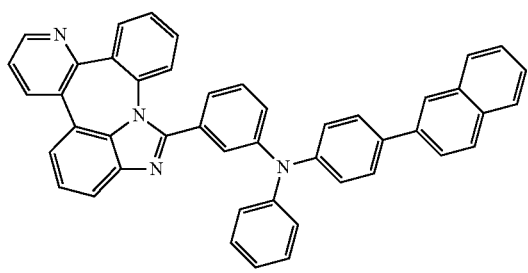

C-136

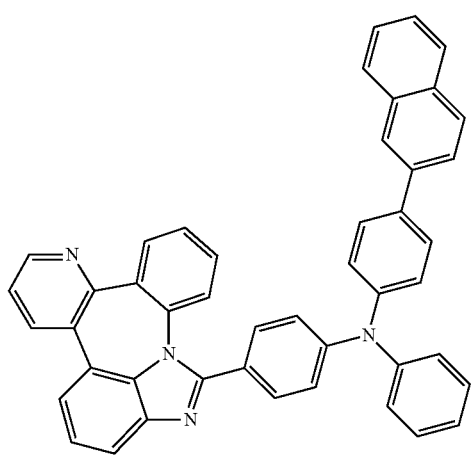

C-137

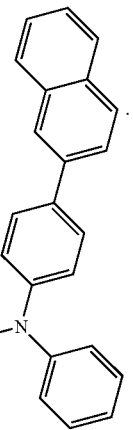

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is comprised in at least one layer of an electron buffer material and an electron transport layer.

9. A display device comprising the organic electroluminescent compound according to claim 1.

* * * * *